(12) United States Patent
Ziv et al.

(10) Patent No.: US 8,911,345 B2
(45) Date of Patent: Dec. 16, 2014

(54) APPARATUSES FOR THE AMELIORATION OF URINARY INCONTINENCE IN FEMALES

(71) Applicant: Kimberly-Clark Worldwide, Inc., Neenah, WI (US)

(72) Inventors: Elan Ziv, Ramat-Gan (IL); Jacob Gilan, Binyamina (IL); Nir Sinai, Alon HaGalil (IL); Idan Bauder, Carmiel (IL); Michal Tune, Herzlia (IL); Eliahu Eliachar, Haifa (IL); Alex Grinberg, Yokneam (IL); Roni Shabat, Kibbutz Yizrael (IL)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 13/772,410

(22) Filed: Feb. 21, 2013

(65) Prior Publication Data
US 2013/0165743 A1 Jun. 27, 2013

Related U.S. Application Data

(63) Continuation of application No. 12/373,937, filed as application No. PCT/IL2007/000893 on Jul. 16, 2007, now Pat. No. 8,435,168.

(30) Foreign Application Priority Data
Jul. 16, 2006 (IL) .......................................... 176883

(51) Int. Cl.
*A61F 2/00* (2006.01)
(52) U.S. Cl.
CPC .............. *A61F 2/0045* (2013.01); *A61F 2/005* (2013.01); *A61F 2250/0071* (2013.01)
USPC ........................................................... 600/30

(58) Field of Classification Search
CPC  A61F 2/005; A61F 2250/0071; A61F 5/4553
USPC ................ 600/1–7, 29, 30, 31; 128/830–841; 606/151; 604/96.01
See application file for complete search history.

(56) References Cited

U.S. PATENT DOCUMENTS

| 2,141,040 | A | 12/1938 | Holt |
| 2,146,574 | A | 2/1939 | Hay |
| 2,432,768 | A | 12/1947 | Kurkjian |
| 2,938,519 | A | 5/1960 | Marco |

(Continued)

FOREIGN PATENT DOCUMENTS

| DE | 271657 | 3/1914 |
| DE | 19816349 | 10/1999 |

(Continued)

OTHER PUBLICATIONS http://www.straightdope.com/columns/read/2330/whats-the-story-with-vaginal-foreign-bodies—Dec. 21, 2001 Cecil Adams Accessed Mar. 24, 2014.*

(Continued)

*Primary Examiner* — Christine Matthews
*Assistant Examiner* — Joshua D Lannu
(74) *Attorney, Agent, or Firm* — Kimberly-Clark Worldwide, Inc.

(57) ABSTRACT

An apparatus for treating urinary incontinence, comprising: a node; a support section adapted for providing urethral support attached to the node; and, an anchoring section adapted for resisting movement of the apparatus attached to the node opposite the support section. Optionally, the support section is adapted to treat incontinence according to at least one of: SUTFS, colpo-elevation or colpo-distension.

11 Claims, 34 Drawing Sheets

(56) References Cited

U.S. PATENT DOCUMENTS

| | | |
|---|---|---|
| 3,138,159 A | 6/1964 | Schmidt |
| 3,333,349 A * | 8/1967 | Brumlik .................. 434/278 |
| 3,646,929 A | 3/1972 | Bonnar |
| 3,683,906 A * | 8/1972 | Robinson .................. 128/839 |
| 3,789,828 A | 2/1974 | Schulte |
| 3,797,478 A | 3/1974 | Walsh et al. |
| 3,841,304 A | 10/1974 | Jones |
| 4,019,498 A | 4/1977 | Hawtrey |
| 4,019,499 A | 4/1977 | Fitzgerald |
| 4,139,006 A | 2/1979 | Corey |
| 4,142,649 A * | 3/1979 | Forgey .................. 221/82 |
| 4,212,301 A | 7/1980 | Johnson |
| 4,307,716 A | 12/1981 | Davis |
| 4,428,365 A | 1/1984 | Hakky |
| 4,457,299 A | 7/1984 | Cornwell |
| 4,553,533 A | 11/1985 | Leighton |
| 4,726,805 A | 2/1988 | Sanders |
| 4,823,814 A | 4/1989 | Drogendijk et al. |
| 4,846,784 A | 7/1989 | Haber |
| 4,850,963 A | 7/1989 | Sparks et al. |
| 4,920,986 A | 5/1990 | Biswas |
| 5,007,894 A | 4/1991 | Enhorning |
| 5,014,722 A | 5/1991 | Bauer |
| 5,036,867 A | 8/1991 | Biswas |
| 5,041,077 A | 8/1991 | Kulick |
| 5,090,424 A | 2/1992 | Simon et al. |
| 5,224,493 A * | 7/1993 | Sawan et al. .................. 128/832 |
| 5,224,494 A | 7/1993 | Enhorning |
| 5,336,208 A | 8/1994 | Rosenbluth et al. |
| 5,352,182 A | 10/1994 | Kalb et al. |
| 5,370,657 A | 12/1994 | Irie |
| 5,386,836 A | 2/1995 | Biswas |
| 5,417,226 A | 5/1995 | Juma |
| 5,483,976 A | 1/1996 | McLaughlin et al. |
| 5,603,685 A | 2/1997 | Tutrone, Jr. |
| 5,609,586 A | 3/1997 | Zadini et al. |
| 5,618,256 A | 4/1997 | Reimer |
| 5,659,934 A | 8/1997 | Jessup et al. |
| 5,671,755 A | 9/1997 | Simon et al. |
| 5,724,994 A | 3/1998 | Simon et al. |
| 5,755,906 A | 5/1998 | Achter et al. |
| 5,771,899 A | 6/1998 | Martelly et al. |
| 5,782,745 A | 7/1998 | Benderev |
| 5,785,640 A | 7/1998 | Kresch et al. |
| 5,788,664 A | 8/1998 | Scalise |
| 5,795,346 A | 8/1998 | Achter et al. |
| 5,894,842 A | 4/1999 | Rabin et al. |
| 6,013,023 A | 1/2000 | Klingenstein |
| 6,090,038 A | 7/2000 | Zunker et al. |
| 6,090,098 A | 7/2000 | Zunker et al. |
| 6,142,928 A | 11/2000 | Zunker et al. |
| 6,158,435 A | 12/2000 | Dorsey |
| 6,189,535 B1 | 2/2001 | Enhorning |
| 6,216,698 B1 | 4/2001 | Regula |
| 6,251,122 B1 | 6/2001 | Tsukernik |
| 6,413,206 B2 | 7/2002 | Biswas |
| 6,415,484 B1 | 7/2002 | Moser |
| 6,418,930 B1 | 7/2002 | Fowler |
| 6,428,467 B1 | 8/2002 | Benderev |
| 6,458,072 B1 | 10/2002 | Zunker |
| 6,460,542 B1 | 10/2002 | James |
| 6,461,215 B1 * | 10/2002 | Kunz et al. .................. 446/107 |
| 6,478,726 B1 | 11/2002 | Zunker |
| 6,503,190 B1 | 1/2003 | Ulmsten et al. |
| 6,558,370 B2 | 5/2003 | Moser |
| 6,645,136 B1 | 11/2003 | Zunker et al. |
| 6,676,594 B1 | 1/2004 | Zunker et al. |
| 6,679,831 B1 | 1/2004 | Zunker et al. |
| 6,739,340 B1 | 5/2004 | Jensen et al. |
| 6,770,025 B2 | 8/2004 | Zunker |
| 6,808,485 B2 | 10/2004 | Zunker |
| 7,036,511 B2 | 5/2006 | Nissenkorn |
| 7,717,892 B2 | 5/2010 | Bartning et al. |
| 7,931,671 B2 | 4/2011 | Tenerz |
| 2002/0068023 A1 | 6/2002 | Davis |
| 2002/0083949 A1 | 7/2002 | James |
| 2002/0115906 A1 | 8/2002 | Miller |
| 2002/0120243 A1 | 8/2002 | Kraemer et al. |
| 2002/0138035 A1 | 9/2002 | Hull, Jr. |
| 2002/0156341 A1 | 10/2002 | Zunker |
| 2002/0156343 A1 | 10/2002 | Zunker |
| 2002/0183711 A1 | 12/2002 | Moser |
| 2003/0149334 A1 | 8/2003 | Ulmsten et al. |
| 2003/0149392 A1 | 8/2003 | Arnould |
| 2004/0054252 A1 | 3/2004 | Zunker |
| 2004/0078013 A1 | 4/2004 | Zunker et al. |
| 2004/0084054 A1 | 5/2004 | Kaseki et al. |
| 2004/0122285 A1 | 6/2004 | Zunker |
| 2004/0158122 A1 | 8/2004 | Guerquin |
| 2004/0199100 A1 | 10/2004 | LeMay et al. |
| 2005/0016545 A1 | 1/2005 | Nissenkorn |
| 2006/0100475 A1 * | 5/2006 | White et al. .................. 600/3 |
| 2007/0088189 A1 | 4/2007 | Levy |
| 2007/0203429 A1 | 8/2007 | Ziv |
| 2007/0244352 A1 | 10/2007 | Ziv |
| 2008/0149109 A1 | 6/2008 | Ziv |
| 2008/0281149 A1 | 11/2008 | Sinai et al. |
| 2009/0266367 A1 | 10/2009 | Ziv et al. |
| 2009/0283099 A1 | 11/2009 | Harmanli |
| 2011/0065980 A1 | 3/2011 | Ziv et al. |
| 2012/0271098 A1 | 10/2012 | Ziv et al. |

FOREIGN PATENT DOCUMENTS

| | | |
|---|---|---|
| EP | 0264258 | 4/1988 |
| EP | 0274762 | 7/1988 |
| EP | 0933069 | 8/1988 |
| EP | 0700669 | 3/1996 |
| EP | 0921778 | 6/1999 |
| EP | 0955024 | 11/1999 |
| EP | 1139963 | 10/2001 |
| EP | 1139962 | 5/2005 |
| EP | 1727491 | 12/2006 |
| FR | 2843700 | 2/2004 |
| GB | 1115727 | 5/1968 |
| GB | 2352181 | 1/2001 |
| GB | 2384436 | 7/2003 |
| JP | 63-177852 | 7/1988 |
| JP | 03-500489 | 2/1991 |
| JP | 06-133996 | 5/1994 |
| JP | 06-503982 | 5/1994 |
| JP | 61-33996 | 5/1994 |
| JP | 09-501595 | 2/1997 |
| JP | 2001-502929 | 3/2001 |
| JP | 2002-532198 | 2/2002 |
| JP | 2002-5332199 | 10/2002 |
| WO | WO 88/10106 | 0/1988 |
| WO | WO 89/09582 | 10/1989 |
| WO | WO 95/05790 | 3/1995 |
| WO | WO 96/01084 | 1/1996 |
| WO | WO 97/34550 | 9/1997 |
| WO | WO 98/49980 | 11/1998 |
| WO | WO 00/03659 | 1/2000 |
| WO | WO 00/36996 | 6/2000 |
| WO | WO 00/67662 | 11/2000 |
| WO | WO 02/26160 | 4/2002 |
| WO | WO 02/089704 | 11/2002 |
| WO | WO 03/047476 | 6/2003 |
| WO | WO 04/000433 | 12/2003 |
| WO | WO 2004/103213 | 12/2004 |
| WO | WO 2005/087153 | 9/2005 |
| WO | WO 2005/087154 | 9/2005 |
| WO | WO 2006/097935 | 9/2006 |
| WO | WO 2008/010214 | 1/2008 |
| WO | WO 2008/079271 | 7/2008 |
| WO | WO 2008/152628 | 12/2008 |
| WO | WO 2009/044394 | 4/2009 |
| WO | WO 2009/130702 | 10/2009 |

OTHER PUBLICATIONS

Official Action Dated May 6, 2013 From the US Patent and Trademark Office Re. U.S. Appl. No. 11/886,248.

(56) References Cited

OTHER PUBLICATIONS

Official Action Dated Mar. 12, 2013 From the US Patent and Trademark Office Re. U.S. Appl. No. 12/680,575.
Supplemental Notice of Allowability Dated Apr. 2, 2013 From the US Patent and Trademark Office Re. U.S. Appl. No. 12/373,937.
Translation of Office Action Dated Mar. 5, 2013 From the State Intellectual Property Office of the People's Republic of China Re. Application No. 200980123856.5.
Translation of Reasons for Rejection Dated Mar. 18, 2013 From the Japanese Patent Office Re. Application No. 2011-223943.
Request for Examination Dated Apr. 4, 2013 From the Federal Service for Intellectual Property, Federal State Budgetary Institution, Federal Institute of Industrial Property of the Russian Federation Re. Application No. 2010146714 and Its Summary in English.
Requisition by the Examiner Dated May 28, 2013 From the Canadian Intellectual Property Office Re. Application No. 2,600,988.
Communication Pursuant to Article 94(3) EPC Dated Nov. 3, 2011 From the European Patent Office Re. Application No. 07789949.0.
Communication Pursuant to Article 94(3) EPC Dated Feb. 4, 2011 From the European Patent Office Re. Application No. 04734069.0.
Communication Pursuant to Article 94(3) EPC Dated Apr. 16, 2009 From the European Patent Office Re.: Application No. 05718876.5.
Communication Pursuant to Article 94(3) EPC Dated Mar. 23, 2010 From the European Patent Office Re.: Application No. 05718876.5.
Communication Relating to the Results of the Partial International Search Dated Mar. 3, 2011 From the International Searching Authority Re. Application No. PCT/IL2010/000985.
Communication Relating to the Results of the Partial International Search Dated Dec. 7, 2007 From the International Searching Authority Re.: Application No. PCT/IL2007/000893.
Communication Relating to the Results of the Partial International Search Dated Jan. 12, 2009 From the International Searching Authority Re.: Application No. PCT/IL2007/000893.
Communication Relating to the Results of the Partial International Search Dated Jan. 12, 2009 From the International Searching Authority Re.: Application No. PCT/IL2008/001292.
Communication Relating to the Results of the Partial International Search Dated Aug. 18, 2009 From the International Searching Authority Re.: Application No. PCT/IL2009/000443.
Communication Under Rule 112 EPC Dated Oct. 22, 2007 From the European Patent Office Re.: Application No. 05718876.5.
Communiction Pursuant to Article 94(3) EPC Dated Jul. 2, 2010 From the European Patent Office Re.: Application No. 05718877.3.
Communiction Pursuant to Article 94(3) EPC Dated Apr. 16, 2009 From the European Patent Office Re.: Application No. 05718877.3.
Decision to Refuse A European Patent Application Dated Feb. 25, 2013 From the European Patent Office Re. Application No. 04734069.0.
European Search Report Under Rule 112 EPC Dated Dec. 27, 2007 From the European Patent Office Re.: Application No. 05718876.5.
Examination Report Dated Oct. 13, 2010 From the Instituto Mexicano de la Propicdad Industrial Re. Application No. MX/a/2007/011339 and Its Summary in English.
Examination Report Dated Oct. 13, 2011 From the Instituto Mexicano de la Propicdad Industrial Re. Application No. MX/a/2007/011339 and Its translation Into English.
Examination Report Dated Feb. 16, 2012 From the Government of India, Patent Office, Intellectual Property Building Re. Application No. 3837/CHENP/2006.
Examination Report Dated Jan. 16, 2012 From the Instituto Mexicano de la Propriedad Industrial Re. Application No. PA/a/2006/010653 and Its Summary in English.
Examination Report Dated May 30, 2012 From the Instituto Mexicano de la Propiedad Industrial Re. Application No. MX/a/2007/011339 and Its Translation Into English.
Examination Report Dated Mar. 31, 2011 From the Instituto Mexicano de la Propiedad Industrial Re. Application No. MX/a/2007/011339.
Examiner-Initiated Interview Summary Dated Oct. 10, 2012 From the US Patent and Trademark Office Re. U.S. Appl. No. 12/680,575.
Examiner's Report Dated Dec. 9, 2009 From the Australian Government, IP Australia Re.: Application No. 2005221424.
Examiner's Report Dated Dec. 15, 2010 From the Australian Government, IP Australia Re.: Application No. 2005221424.
Examiner's Report Dated Nov. 29, 2010 From the Australian Government, IP Australia Re. Application No. 2006224158.
International Preliminary Report on Patentability Dated Jul. 6, 2006 From the International Preliminary Examining Authority Re.: Application No. PCT/IL2005/000304.
International Preliminary Report on Patentability Dated Jun. 7, 2012 From the International Bureau of WIPO Re. Application No. PCT/IL2010/000985.
International Preliminary Report on Patentability Dated Dec. 8, 2009 From the International Preliminary Examining Authority Re.: Application No. PCT/IL2008/001292.
International Preliminary Report on Patentability Dated Oct. 14, 2008 From the International Preliminary Examining Authority Re.: Application No. PCT/IL06/00346.
International Preliminary Report on Patentability Dated Jul. 15, 2010 From the International Preliminary Examining Authority Re.: Application No. PCT/IL2009/000443.
International Preliminary Report on Patentability Dated Dec. 23, 2009 From the International Bureau of WIPO Re.: Application No. PCT/IL2008/000786.
International Preliminary Report on Patentability Dated Jul. 24, 2006 From the International Preliminary Examining Authority Re.: Application No. PCT/IL2005/000303.
International Preliminary Report on Patentability Dated Jan. 29, 2009 From the International Bureau of WIPO Re.: Application No. PCT/IL2007/000893.
International Search Report and the Written Opinion Dated May 9, 2011 From the International Searching Authority Re. Application No. PCT/IL2010/000985.
International Search Report and the Written Opinion Dated Oct. 26, 2005 From the International Searching Authority Re.: Application No. PCT/IL2005/000303.
International Search Report and the Written Opinion Dated Oct. 28, 2009 From the International Searching Authority Re.: Application No. PCT/IL2009/000443.
International Search Report Dated Dec. 11, 2006 From the International Searching Authority Re.: Application No. PCT/IL06/00346.
International Search Report Dated Apr. 14, 2008 From the international Searching Authority Re.: Application No. PCT/IL2007/000893.
International Search Report Dated Sep. 23, 2005 From the International Searching Authority Re.: Application No. PCT/IL2005/000304.
International Search Report Dated Oct. 24, 2008 From the International Searching Authority Re.: Application No. PCT/IL2008/000786.
International Search Report Dated Mar. 25, 2009 From the International Searching Authority Re.: Application No. PCT/IL2008/001292.
Interview Summary Dated Feb. 9, 2011 From the US Patent and Trademark Office Re.: U.S. Appl. No. 10/593,367.
Letter After Telephone Conference Dated Jul. 5, 2010 From the International Searching Authority Re. Application No. PCT/IL2009/000443.
Notice of Acceptance Dated Feb. 2, 2011 From the Australian Government, IP Australia Re.: Application No. 2005221424.
Notice of Allowance Dated Jan. 7, 2013 From the US Patent and Trademark Office Re. U.S. Appl. No. 12/373,937.
Notice of Allowance Dated Nov. 14, 2011 From the US Patent and Trademark Office Re.: U.S. Appl. No. 10/593,367.
Notice of Allowance Dated Mar. 31, 2010 From the US Patent and Trademark Office Re.: U.S. Appl. No. 10/557,865.
Notification Dated Dec. 17, 2008 From the Patent Office of the Russian Federation Re.: Application No. 2006136791 and Its Translation Into English.
Notification of Reasons for Rejection Dated Feb. 18, 2011 From the Japanese Patent Office Re. Application No. 2007-503494 and Its Translation into English.

(56) References Cited

OTHER PUBLICATIONS

Office Action Dated Sep. 1, 2008 From the Israeli Patent Office Re.: Application No. 156070 and Its Translation Into English.
Office Action Dated Sep. 1, 2008 From the Israeli Patent Office Re.: Application No. 157117 and Its Translation Into English.
Office Action Dated Apr. 5, 2011 From the Israel Patent Office Re.: Application No. 156070 and Its Translation Into English.
Office Action Dated Dec. 5, 2012 From the Israel Patent Office Re. Application No. 176883 and Its Translation Into English.
Office Action Dated Jan. 9, 2009 From the State Intellectual Property Office of the People's Republic of China Re.: Application No. 200580016245.2 and Its Translation Into English.
Office Action Dated Jan. 18, 2010 From the Israel Patent Office Re.: Application No. 156070 and Its Translation Into English.
Office Action Dated Jul. 24, 2011 From the Israel Patent Office Re. Application No. 176883 and Its Translation Into English.
Official Action Dated Aug. 4, 2010 From the US Patent and Trademark Office Re.: U.S. Appl. No. 10/598,872.
Official Action Dated Sep. 5, 2008 From the US Patent and Trademark Office Re.: U.S. Appl. No. 10/557,865.
Official Action Dated Mar. 6, 2009 From the US Patent and Trademark Office Re.: U.S. Appl. No. 10/557,865.
Official Action Dated Apr. 9, 2012 From the US Patent and Trademark Office Re. U.S. Appl. No. 12/417,011.
Official Action Dated Oct. 12, 2010 From the US Patent and Trademark Office Re.: U.S. Appl. No. 10/598,872.
Official Action Dated Feb. 14, 2011 From the US Patent and Trademark Office Re.: U.S. Appl. No. 10/598,872.
Official Action Dated Oct. 14, 2011 From the US Patent and Trademark Office Re. U.S. Appl. No. 12/417,011.
Official Action Dated Feb. 15, 2012 From the US Patent and Trademark Office Re. U.S. Appl. No. 12/373,937.
Official Action Dated Oct. 15, 2009 From the US Patent and Trademark Office Re.: U.S. Appl. No. 10/557,865.
Official Action Dated Apr. 17, 2009 From the Patent Office of the Russian Federation Re.: Application No. 2006136791 and Its Translation Into English.
Official Action Dated Feb. 19, 2010 From the US Patent and Trademark Office Re.: U.S. Appl. No. 10/593,367.
Official Action Dated Jun. 21, 2011 From the US Patent and Trademark Office Re.: U.S. Appl. No. 10/593,367.
Official Action Dated Jul. 23, 2012 From the US Patent and Trademark Office Re. U.S. Appl. No. 12/373,937.
Official Action Dated Jun. 23, 2010 From the US Patent and Trademark Office Re.: U.S. Appl. No. 10/593,367.
Official Action Dated Aug. 24, 2012 From the US Patent and Trademark Office Re. U.S. Appl. No. 11/886,248.
Official Action Dated Oct. 27, 2009 From the Federal Institute of Industrial and Intellectual Property, Patents and Trademarks, ROSPATENT, of the Russian Federation Re.: Application No. 2007138489 and Its Translation Into English.
Official Action Dated Dec. 28, 2010 From the US Patent and Trademark Office Re.: U.S. Appl. No. 10/593,367.
Official Action Dated Apr. 29, 2010 From the US Patent and Trademark Office Re.: U.S. Appl. No. 10/598,872.
Official Action Dated May 31, 2011 From the US Patent and Trademark Office Re. U.S. Appl. No. 12/417,011.
Patent Examination Report Dated Aug. 9, 2012 From the Australian Government, IP Australia Re. Application No. 2007274574.
Request for Examination Dated Jun. 11, 2010 From the Federal Institute of Industrial and Intellectual Property, Patents and Trademarks, ROSPATENT, of the Russian Federation Re.: Application No. 2010100368 and Its Summary in English.
Request for Examination Dated Mar. 29, 2012 From the Federal Institute of Industrial and Intellectual Property, Patents and Trademarks, ROSPATENT, of the Russian Federation Re.: Application No. 2010100368 and Its Summary in English.
Request for Formal Examination Dated Feb. 24, 2011 From the ROSPATENT, Federal Government Institution, Federal Institute of Industrial Property of the Federal Service for Intellectual Property, Patents and Trademarks of the Russian Federation Re. Application No. 2010146714.
Requisition by the Examiner Dated Feb. 19, 2013 From the Canadian Intellectual Property Office Re. Application No. 2,560,877.
Requisition by the Examiner Dated Aug. 22, 2012 From the Canadian Intellectual Property Office Re. Application No. 2,600,988.
Requisition by the Examiner Dated May 22, 2012 From the Canadian Intellectual Property Office Re. Application No. 2,560,877.
Requisition by the Examiner Dated Aug. 29, 2011 From the Canadian Intellectual Property Office Re. Application No. 2,560,877.
Restriction Official Action Dated Nov. 1, 2012 From the US Patent and Trademark Office Re. U.S. Appl. No. 12/680,575.
Restriction Official Action Dated Feb. 6, 2013 From the US Patent and Trademark Office Re. U.S. Appl. No. 12/663,714.
Restriction Official Action Dated Feb. 28, 2012 From the US Patent and Trademark Office Re. U.S. Appl. No. 11/886,248.
Second Supplemental Notice of Allowability Dated Jun. 3, 2010 From the US Patent and Trademark Office Re.: U.S. Appl. No. 10/557,865.
Supplemental Notice of Allowability Dated Apr. 27, 2010 From the US Patent and Trademark Office Re.: U.S. Appl. No. 10/557,865.
Translation of Decision for Rejection Dated Jun. 9, 2011 From the Japanese Patent Office Re. Application No. 2007-503495.
Translation of Notification of Reasons for Rejection Dated Jun. 1, 2010 From the Japanese Patent Office Re. Application No. 2006-531002.
Translation of Notification of Reasons for Rejection Dated Mar. 18, 2011 From the Japanese Patent Office Re. Application No. 2006-531002.
Translation of Notification of Reasons for Rejection Dated Dec. 24, 2010 From the Japanese Patent Office Re. Application No. 2007-503495.
Translation of Notification of Reasons of Rejection Dated Apr. 8, 2010 From the Japanese Patent Office Re.: Application No. 2007-503494.
Translation of Office Action Dated Sep. 17, 2010 From the State Intellectual Property Office of the People's Republic of China Re.: Application No. 200680017262.2.
Translation of Office Action Dated Dec. 21, 2010 From the State Intellectual Property Office of the People's Republic of China Re. Application No. 200780033622.2.
Translation of Office Action Dated Feb. 22, 2012 From the State Intellectual Property Office of the People's Republic of China Re. Application No. 200780033622.2.
Translation of Office Action Dated Nov. 22, 2012 From the State Intellectual Property Office of the People's Republic of China Re. Application No. 200780033622.2.
Translation of Office Action Dated Apr. 29, 2011 From the State Intellectual Property Office of the People's Republic of China Re.: Application No. 200680017262.2.
Translation of Office Action Dated Jan. 29, 2010 From the State Intellectual Property Office of the People's Republic of China Re.: Application No. 200680017262.2.
Translation of Search Report Dated Nov. 22, 2012 From the State Intellectual Property Office of the People's Republic of China Re. Application No. 200780033622.2.
Written Opinion Dated Dec. 11, 2006 From the International Searching Authority Re.: Application No. PCT/IL06/00346.
Written Opinion Dated Apr. 14, 2008 From the International Searching Authority Re.: Application No. PCT/IL2007/000893.
Written Opinion Dated Nov. 22, 2005 From the International Searching Authority Re.: Application No. PCT/IL2004/000433.
Written Opinion Dated May 23, 2006 From the International Preliminary Examining Authority Re.: Application No. PCT/IL2005/000303.
Written Opinion Dated Sep. 23, 2005 From the International Searching Authority Re.: Application No. PCT/IL2005/000304.
Written Opinion Dated Oct. 24, 2008 From the International Searching Authority Re.: Application No. PCT/IL2008/000786.
Written Opinion Dated Mar. 25, 2009 From the International Searching Authority Re.: Application No. PCT/IL2008/001292.

(56) References Cited

OTHER PUBLICATIONS

Translation of Office Action Dated May 6, 2013 From the State Intellectual Property Office of the People's Republic of China Re. Application No. 200780033622.2.
Translation of Office Action Dated Aug. 22, 2013 From the State Intellectual Property Office of the People's Republic of China Re. Application No. 200780033622.2.
Notice of Allowance Dated Oct. 2, 2013 From the US Patent and Trademark Office Re. U.S. Appl. No. 12/417,011.
Notification of Reasons for Rejection Dated Oct. 4, 2013 From the Japanese Patent Office Re. Application No. 2011-223943 and Its Translation Into English.
Supplementary European Search Report and the European Search Opinion Dated Oct. 21, 2013 From the European Patent Office Re. Application No. 06711327.4.
Communication Pursuant to Rules 70(2) and 70a(2) EPC Dated Nov. 8, 2013 From the European Patent Office Re. Application No. 06711327.4.
Supplemental Notice of Allowability Dated Sep. 24, 2013 From the US Patent and Trademark Office Re. U.S. Appl. No. 11/886,248.
Communication Pursuant to Article 94(3) EPC Dated Nov. 29, 2013 From the European Patent Office Re. Application No. 08808093.2.
Office Action Dated Nov. 12, 2013 From the State Intellectual Property Office of the People's Republic of China Re. Application No. 200980123856.5 and Its Translation Into English.
European Search Report and the European Search Opinion Dated Nov. 14, 2013 From the European Patent Office Re. Application No. 11188150.4.
Applicant-Initiated Interview Summary Dated Aug. 9, 2013 From the US Patent and Trademark Office Re. U.S. Appl. No. 12/680,575.
Applicant-Initiated Interview Summary Dated Jun. 28, 2013 From the US Patent and Trademark Office Re. U.S. Appl. No. 12/680,575.
Invitation Pursuant to Rule 62a(1) EPC Dated Aug. 8, 2013 From the European Patent Office Re. Application No. 06711327.4.
Notice of Allowance Dated Aug. 6, 2013 From the US Patent and Trademark Office Re. U.S. Appl. No. 11/886,248.
Official Action Dated Jul. 1, 2013 From the US Patent and Trademark Office Re. U.S. Appl. No. 12/663,714.
Official Action Dated Jul. 23, 2013 From the US Patent and Trademark Office Re. U.S. Appl. No. 10/598,872.

\* cited by examiner

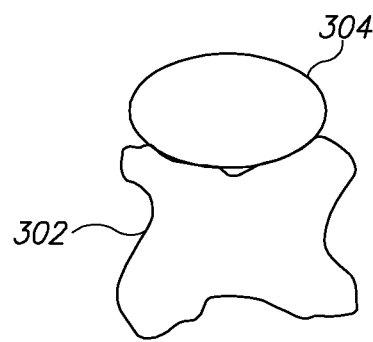
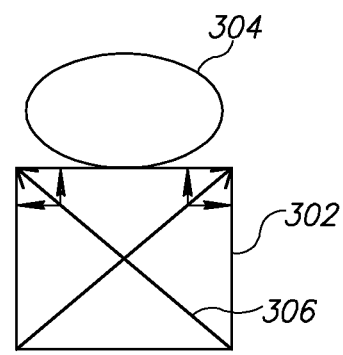
FIG.3A    FIG.3B
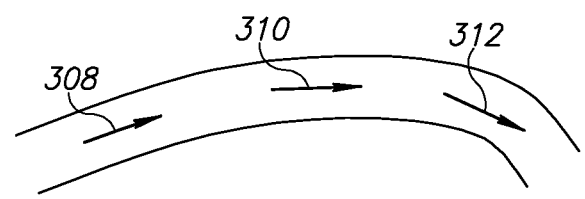
FIG.3C
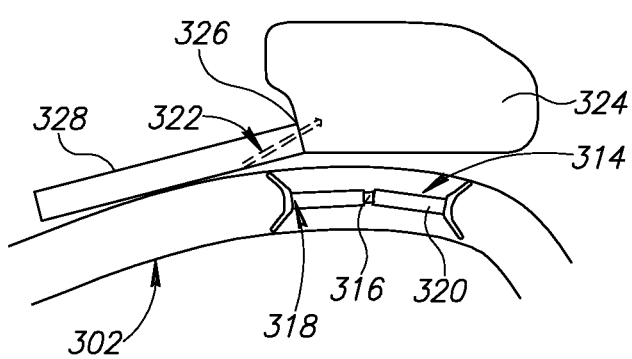
FIG.3D

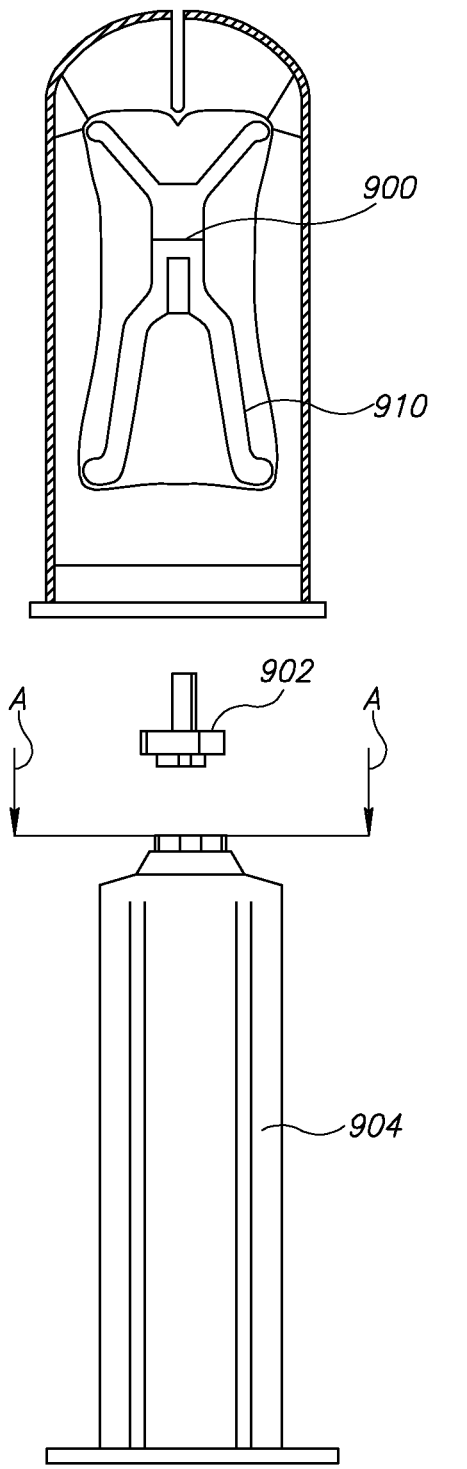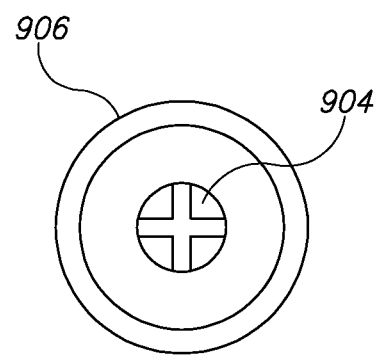
FIG.9B
VIEW A-A
FIG.9A

VIEW A—A

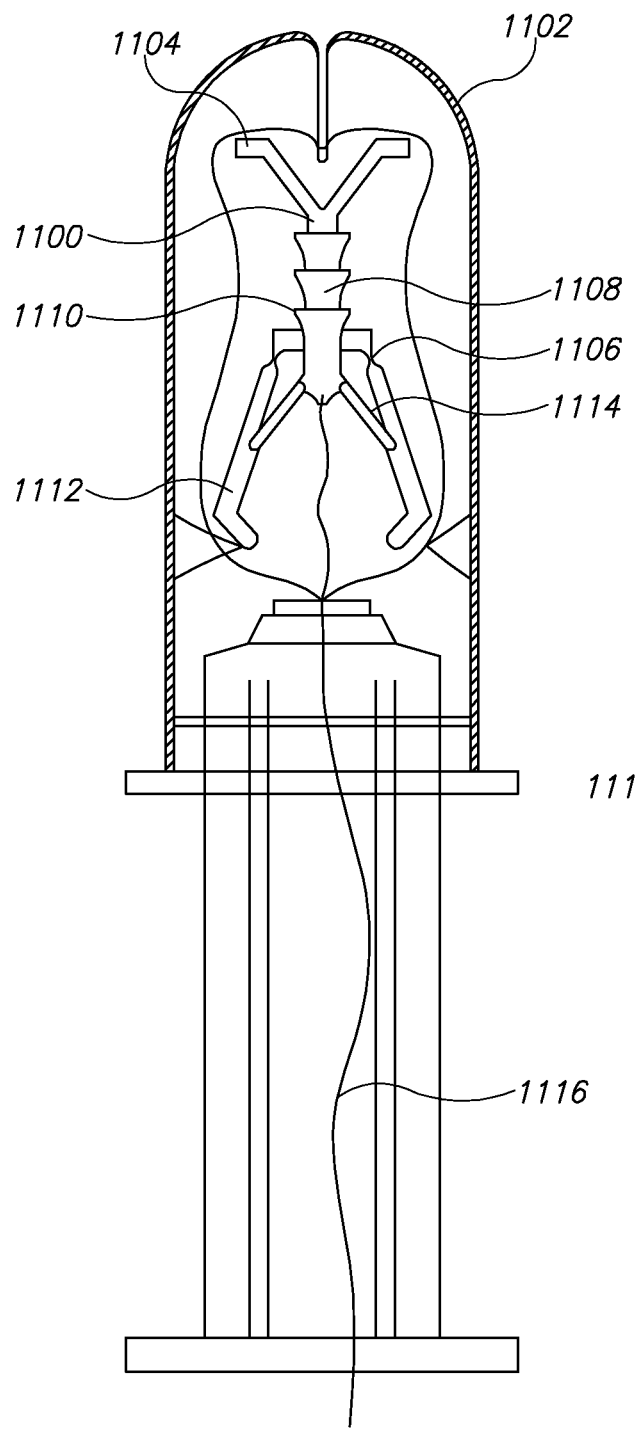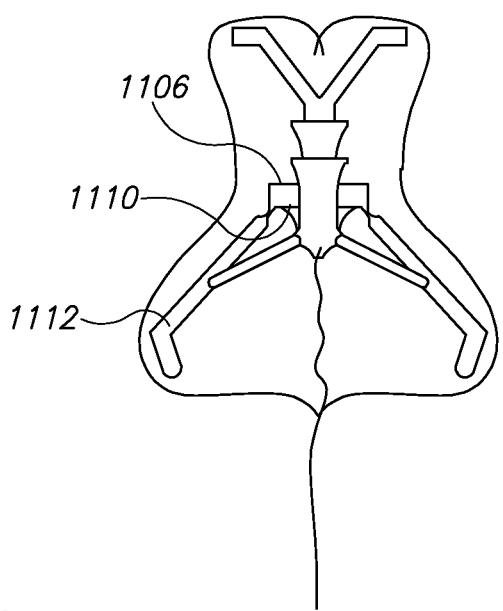
FIG.11A
FIG.11B

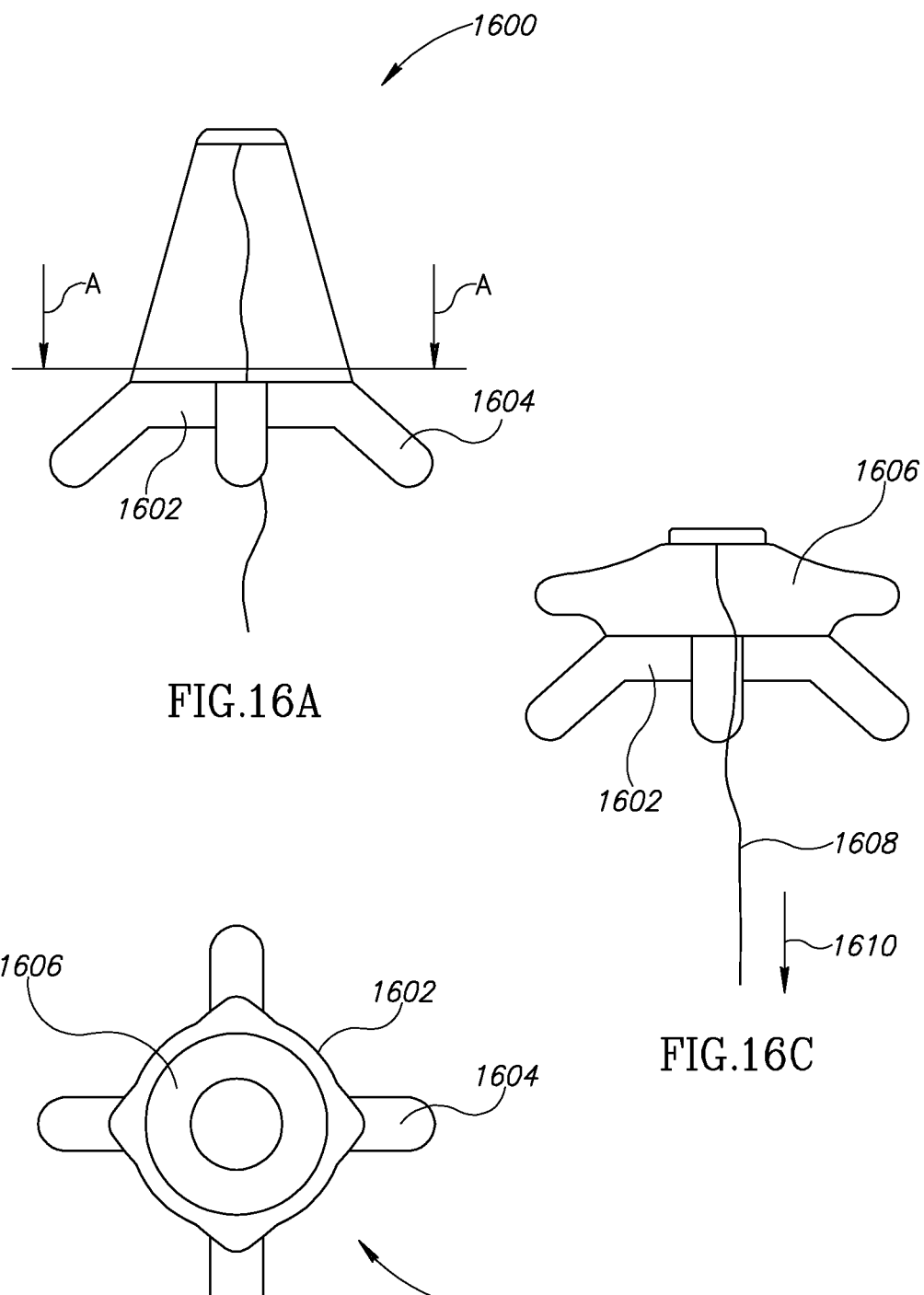

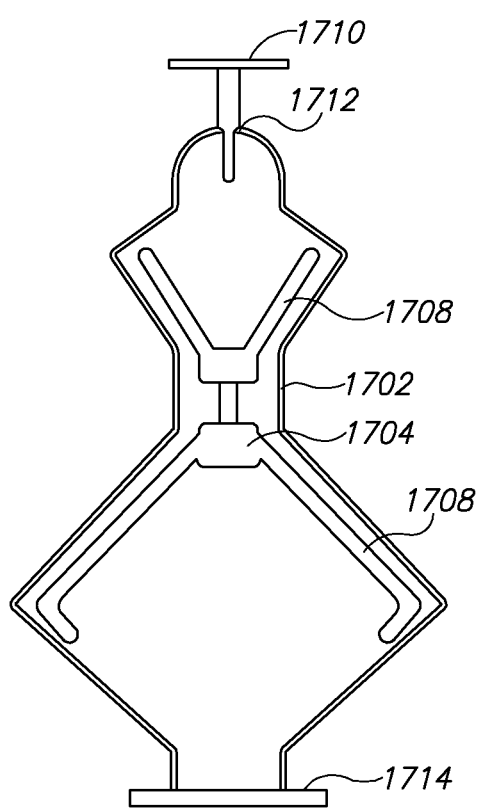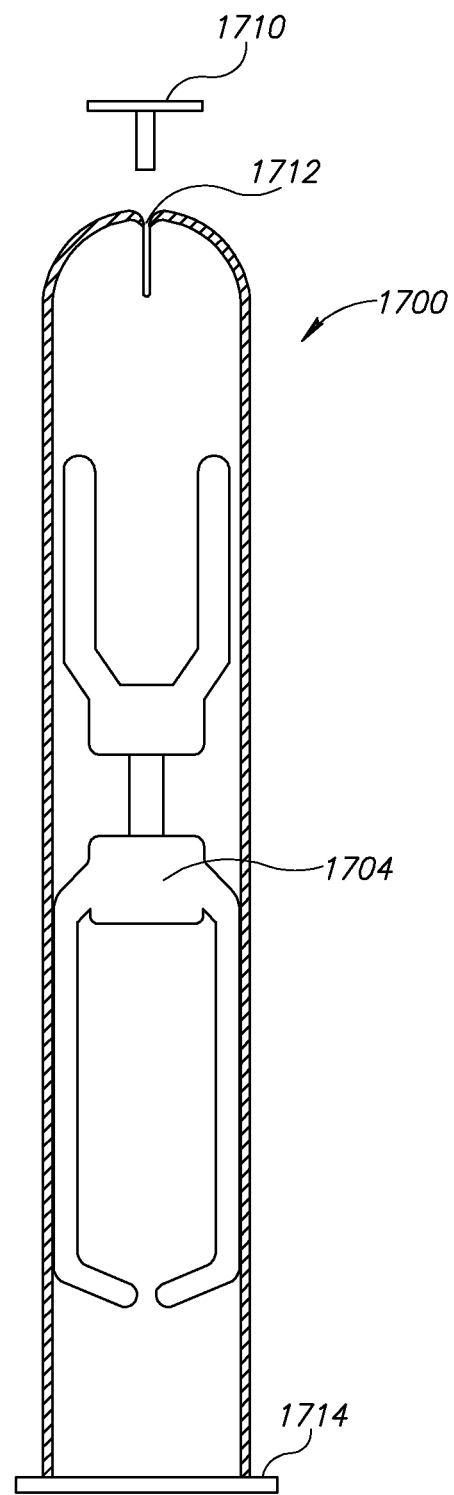
FIG.17A
FIG.17B

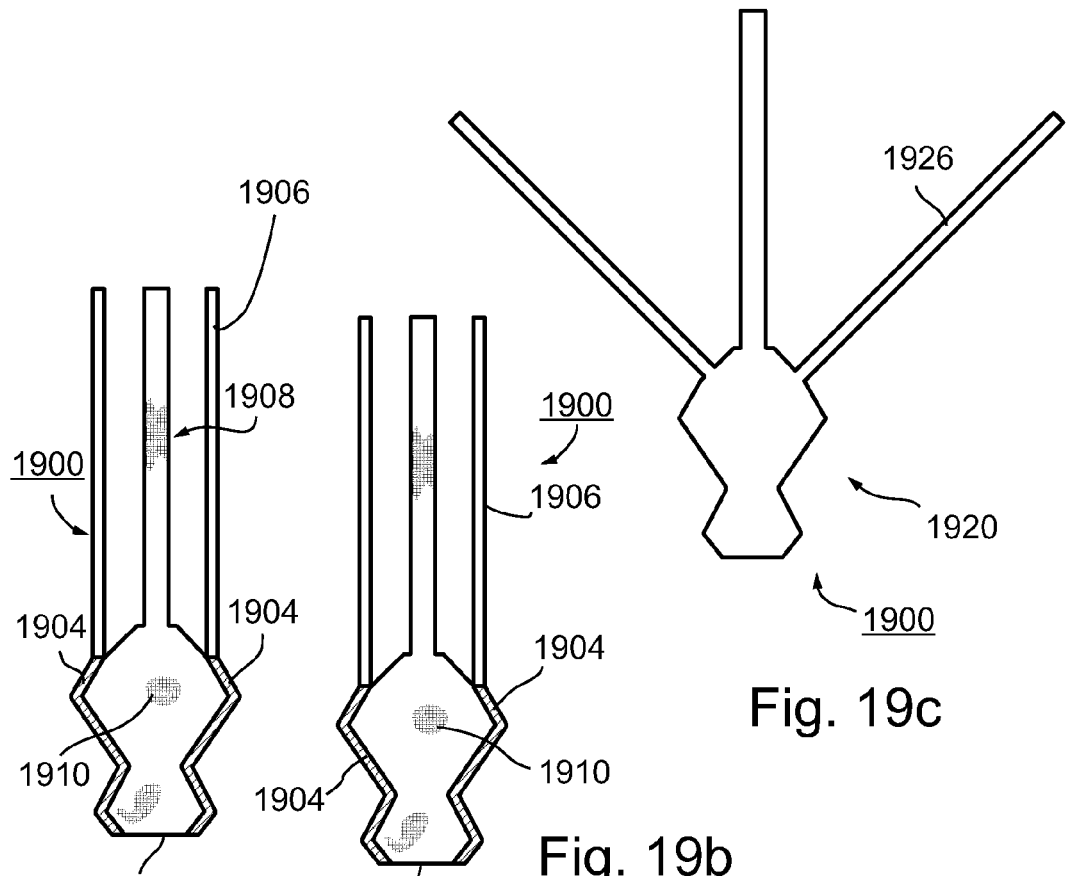
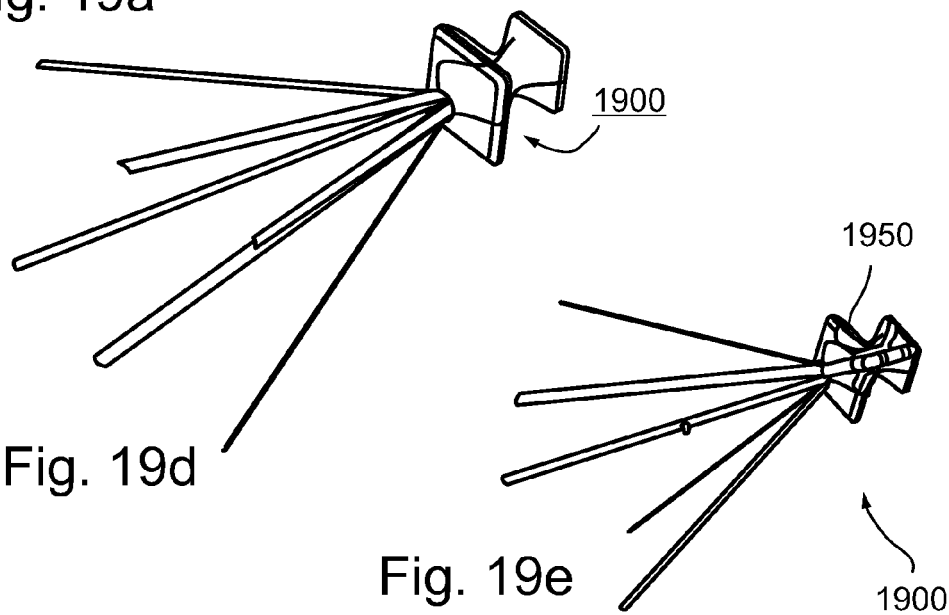
Fig. 19a
Fig. 19b
Fig. 19c
Fig. 19d
Fig. 19e

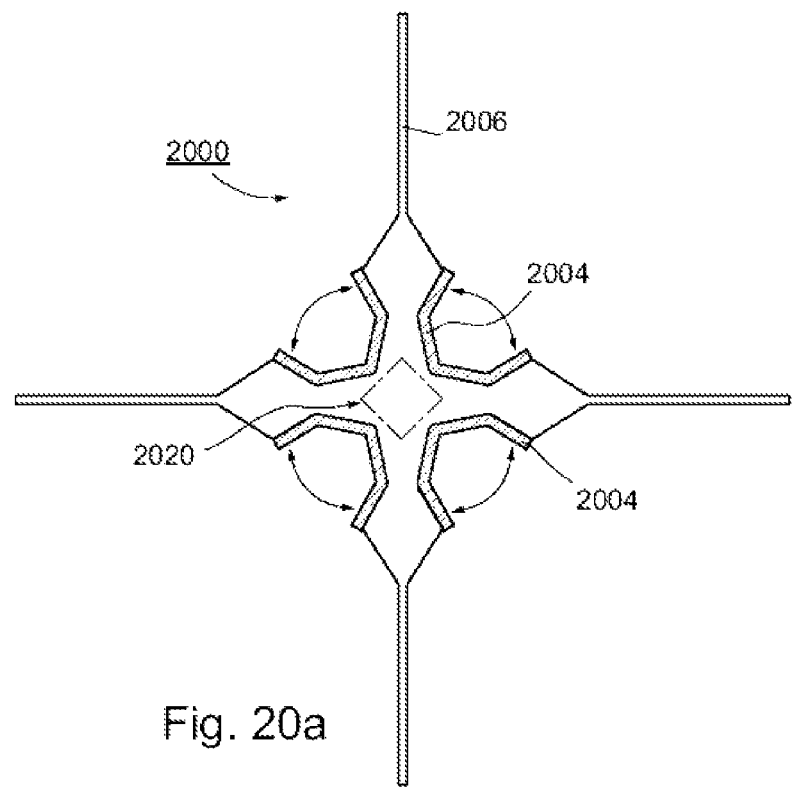
Fig. 20a
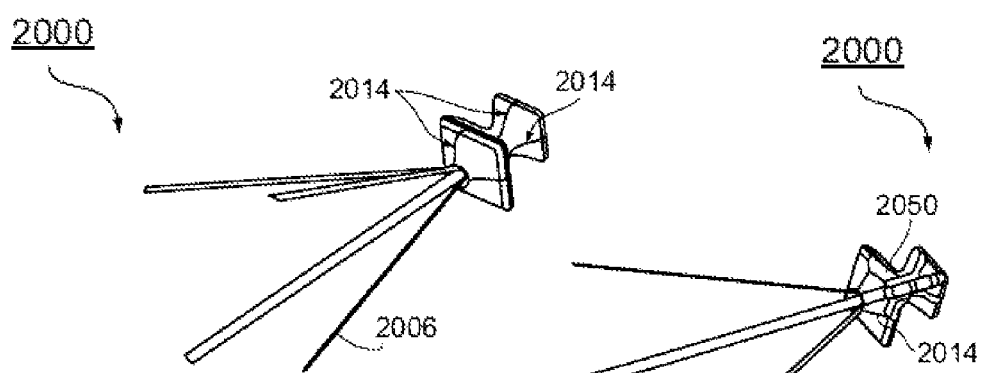
Fig. 20b
Fig. 20c

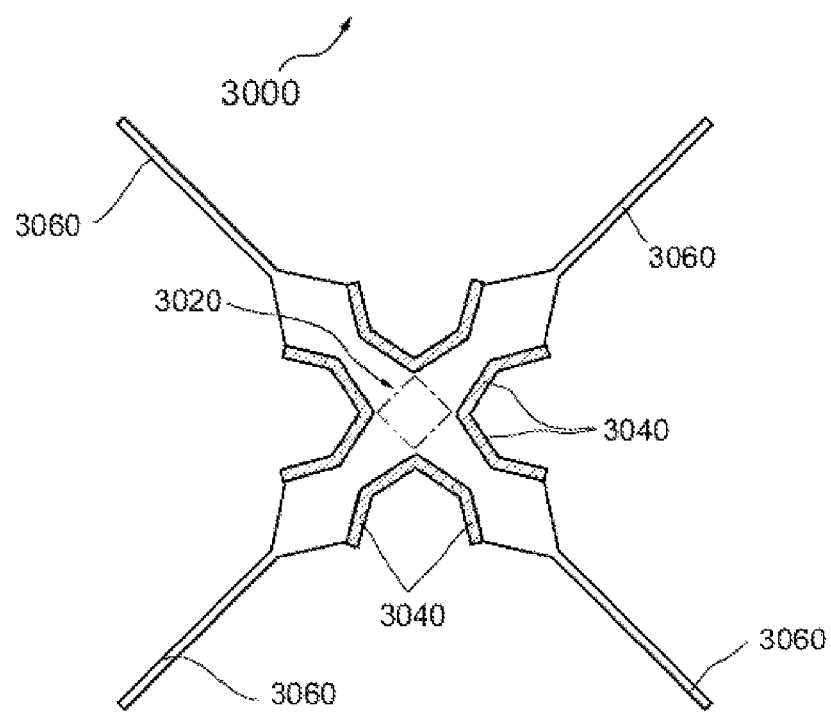
Fig. 21a
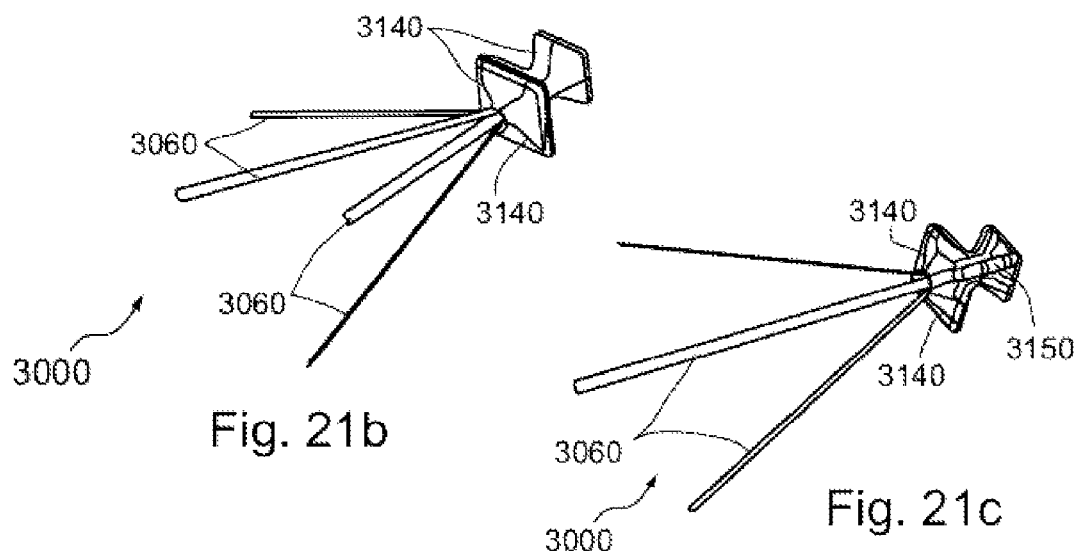
Fig. 21b
Fig. 21c ial No. 12/373,937 filed on Jan. 15, 2009, which is a National Phase of PCT Patent Application No. PCT/IL2007/000893 having International filing date of Jul. 16, 2007, which claims the benefit of priority of Israel Patent Application No. 176883 filed on Jul. 16, 2006. The contents of the above applications are all incorporated herein by reference.

APPARATUSES FOR THE AMELIORATION OF URINARY INCONTINENCE IN FEMALES

RELATED APPLICATIONS

This application is a continuation of U.S. patent application Ser. No. 12/373,937 filed on Jan. 15, 2009, which is a National Phase of PCT Patent Application No. PCT/IL2007/000893 having International filing date of Jul. 16, 2007, which claims the benefit of priority of Israel Patent Application No. 176883 filed on Jul. 16, 2006. The contents of the above applications are all incorporated herein by reference.

FIELD OF INVENTION

The present invention relates generally to treating feminine medical conditions, for example by providing devices for the prevention of female incontinence and/or pelvic organ prolapse.

BACKGROUND OF THE INVENTION

Urinary incontinence is a widespread problem among females. It is estimated that up to 50% of women occasionally leak urine involuntarily, and that approximately 25% of women will seek medical advice at some point in order to deal with the problem. Stress incontinence, the most common type of urinary incontinence, refers to the involuntary loss of urine resulting from abdominal pressure rise occurring during exercise, coughing, sneezing, laughing, etc. While many different factors may contribute to the development of stress incontinence, it is most prevalent among women ages 35-65 and those who have had multiple vaginal deliveries. Stress incontinence is both aggravating and unpleasant for women, and it can also be embarrassing. Many women wear sanitary pads or diapers in order to deal with incontinence, though this is not a real solution to the problem and it can be very inconvenient and unreliable. Surgical treatment may involve, among others, elevation of the anterior vaginal wall (Anterior Colporrhaphy), securing the paraurethal tissues to the periosteum of the pubic bone (Marshall-Marchetti-Krantz operation), or elevation of the paracervical vaginal anterior wall to the Coopers ligament (Burch Colpo suspension) in order to elevate the bladder neck above the level of the pelvic floor and thereby distribute pressure equally to the bladder, the bladder neck, and the mid-urethra. Recently, a procedure known as "TVT" ("Tension Free Vaginal Tape") was developed, in which a mesh tape is implanted underneath the urethra (usually mid-urethra), creating a hammock on which the urethra may kink during a rise in intra-abdominal pressure. However, surgery is only suitable for severe cases, and the majority of women experiencing incontinence do not need, and certainly would rather avoid, surgical solutions.

One modality of non-surgical treatment involves the use of devices that are inserted into the vagina, either by a medical practitioner or by the woman herself. Most devices are designed to apply pressure against the bladder neck so as to inhibit or completely block the flow of urine through the urethra. A variety of such devices are known in the art. For example, refer to U.S. Publication No. 2002/0183711 to Moser, entitled, "Urinary Incontinence Device"; U.S. Pat. No. 6,739,340 to Jensen, et al., entitled, "Device for prevention of involuntary urination"; U.S. Pat. No. 6,679,831 to Zunker, et al., entitled, "Resilient incontinence insert and a method of making the same"; U.S. Pat. No. 6,460,542 to James, entitled, "Female incontinence control device"; U.S. Pat. No. 6,413,206 to Biswas, entitled, "Intra-vaginal device"; U.S. Pat. No. 5,785,640 to Kresch, entitled "Method for Treating Female Incontinence"; U.S. Pat. No. 5,771,899 to Martelly, et al., entitled, "Pessary"; U.S. Pat. No. 5,618,256 to Reimer, entitled, "Device for Arrangement in the Vagina for Prevention of Involuntary Urination with Females and an Applicator for use in Insertion of the Device"; U.S. Pat. No. 5,417,226 to Juma, entitled, "Female Anti-Incontinence Device"; U.S. Pat. No. 5,386,836 to Biswas, entitled, "Urinary Incontinence Device"; U.S. Pat. No. 5,007,894 to Enhorning, entitled, "Female Incontinence Device"; and U.S. Pat. No. 4,920,986 to Biswas, entitled, "Urinary Incontinence Device", the disclosures of all of which are herein incorporated by reference.

One problem with many of the above listed devices is that they completely block the urethra and thus they need to be removed or collapsed in order to allow the woman to urinate. To overcome this drawback, vaginal devices have been developed having specialized shapes that do not completely block the urethra but these devices tend to be large, uncomfortable, and intrusive. They also tend to cause irritation or soreness to the vagina.

Another common shortcoming is that most devices known in the art also tend to be difficult or painful or uncomfortable to insert and/or remove. In order to correctly inhibit urine flow, the device needs to be properly positioned in the vaginal canal. As a result, a doctor may be required to properly position the device. In most cases, the device is adapted for remaining in the vagina for a prolonged period of time (due to the time and expense of requiring a trained medical professional to insert the device). However, when positioned in the vagina for an extended period of the time, the device may cause vaginal infections, pressure ulcer, and/or bleeding.

SUMMARY OF THE INVENTION

An aspect of some exemplary embodiments of the invention relates to providing an incontinence device designed to provide suburethral support using a principle of operation including at least one of sub-urethral tension free vaginal support (SUTFS), colpo-elevation or colpo-distension. In some embodiments of the invention, more than one of the above principles of operation are used in combination by the device to treat incontinence.

An aspect of some exemplary embodiments of the invention relates to providing a device designed to treat feminine incontinence which are pre-tensioned immediately prior to deployment. In an embodiment of the invention, the devices are stored un-tensioned to improve shelf-life and/or device performance, for example. In some embodiments of the invention, only a support section of the devices is pre-tensioned. The amount of pre-tensioning is adjustable in order to modify the degree of support rendered by the device, in an embodiment of the invention.

An aspect of some exemplary embodiments of the invention relates to providing a device designed to treat feminine incontinence which exhibits a bi-polar configuration, bi-polar for example meaning the device is divided into two operative poles. In some embodiments of the invention, one pole performs a support function and/or one pole performs an anchoring function. In some embodiments of the invention, each pole performs both support and/or anchoring functions. Optionally, a bi-polar device is capable of being inserted either pole first to achieve the same incontinence treating effect. In some embodiments of the invention, each pole is provided with at least one band with at least one anchoring and/or supporting feature. Optionally, the anchoring and/or supporting features are flexible. In some embodiments of the invention, the at least one band is replaceable and/or interchangeable. Optionally, more than one band is provided to at least one pole.

An aspect of some exemplary embodiments of the invention relates to providing a device designed to treat feminine incontinence which is orientationally neutral. In an embodiment of the invention, an orientationally neutral device for treating incontinence can be inserted in any orientation with respect to the vagina and still provide treatment for incontinence. In an embodiment of the invention, an orientationally neutral device is comprised of a core and a plurality of radiating anchoring and/or support features. In some embodiments of the invention, the orientationally neutral device is used to treat prolapse. In some embodiments of the invention, the orientationally neutral device is used as a menstrual tampon. Optionally, the menstrual tampon embodiment of the device has at least an absorbent core. Optionally, the menstrual tampon embodiment of the device has at least absorbent anchoring and/or support features. In some embodiments of the invention, the device is comprised of a solid absorbent material.

An aspect of some exemplary embodiments of the invention relates to providing a device designed to treat feminine incontinence which provides increased support at a supporting section as a result of a stressful event in the vicinity of an anchoring section. In an embodiment of the invention, the supporting and anchoring sections are connected and/or counterbalanced lever elements with a common pivot point between them, forming a lever unit. In some embodiments of the invention, the device is comprised of a plurality of lever units. Optionally, the plurality of lever units is arranged symmetrically around a central axis of the device. Optionally, the plurality of lever units is arranged asymmetrically around a central axis of the device. In some embodiments of the invention, the supporting and/or anchoring sections are flexible.

An aspect of some exemplary embodiments of the invention relates to providing a device designed to treat feminine incontinence without a separate anchoring section. In an embodiment of the invention, anchoring and/or supporting functions are performed by a single component. In an embodiment of the invention, the component is non-planar. Optionally, the component is provided with a plurality of protrusions adapted to assist with anchoring and/or supporting. In some embodiments of the invention, the component is flexible. A flexible membrane is provided to an interior portion of the component in accordance with an embodiment of the invention.

An aspect of some exemplary embodiments of the invention relates to providing a device for treating incontinence wherein at least a portion of the device changes a material property upon deployment into a user's vagina. In some embodiments of the invention, a device comprised of a material selected for its ability to alter material properties is stored and inserted exhibiting a first material property and transitions to a second material property when in situ. For example, the first material property could exhibit sufficient flexibility for easy storage and insertion while the second material property could be more rigid, to provide support. Optionally, the material is viscose or a similar material such as used to make menstrual tampons. Optionally, the material is a solid absorbent, such as a "Super Absorbent Polymer" (e.g. polyacrylamide). Optionally, the material is a laminate.

In an embodiment of the invention, fluids, such as the natural vaginal secretions of the user, or fluids stored in a small sack next to the material, cause a change in the material property of at least the portion of the device. In some embodiments of the invention, heat, such as the body heat of the user, causes a change in the material property of at least the portion of the device. In some embodiments of the invention, the material is treated so that upon the transition to the second material property the device assumes a pre-designed shape effective for rendering incontinence treatment. Optionally, treating includes stitching. Optionally, treating includes ultrasonic welding.

An aspect of some exemplary embodiments of the invention relates to providing an applicator designed to transition the shape of the applicator (and therefore an enclosure within the applicator) from a storage configuration to a deployment configuration. In some embodiments of the invention when in the storage configuration, the applicator is designed to accommodate a non-tensioned device for treating incontinence. Optionally, the applicator assumes a storage configuration adapted to accommodate a non-tensioned support section of an incontinence treating device. In some embodiments of the invention, the applicator transitions to a deployment configuration wherein at least the support section of the device is tensioned. Optionally, the transition of the applicator from a storage configuration to a deployment configuration actuates the tensioning of at least the support section of the device.

An aspect of some exemplary embodiments of the invention relates to providing a device for treating incontinence which also provides pharmaceutical treatment to the user. In an embodiment of the invention, the device is coated with a polymer including a pharmaceutical which elutes from the polymer upon deployment into a user's vagina. Optionally, only a portion of the device is adapted to elute pharmaceuticals, for example those portions of the device which are designed to contact the vaginal wall directly.

An aspect of some embodiments of the invention relates to assembly of an intravaginal device for amelioration of incontinence from a plurality of rods and at least one base adapted to connect the rods in a desired configuration. In an exemplary embodiment of the invention, the rods are constructed of a flexible material (e.g. silicon) and the base(s) are rigid. Optionally, assembly of rods and bases contributes to a reduction in production cost.

There is thus provided in accordance with an exemplary embodiment of the invention, an apparatus for treating urinary incontinence, comprising: a node; a support section adapted for providing urethral support attached to the node; and, an anchoring section adapted for resisting movement of the apparatus attached to the node opposite the support section; wherein the support section is adapted to treat incontinence according to at least one of: SUTFS, colpo-elevation or colpo-distension. Optionally, the support section is provided with at least 2 supporting arms. Optionally, the anchoring section is provided with at least 2 anchoring arms. Optionally, the at least two supporting arms are angled inwards towards a central axis of the apparatus. Optionally, the at least one arm is short than another arm. In an embodiment of the invention, the apparatus further comprises a cover. Optionally, the cover substantially encapsulates the node, support section and the anchoring section. Optionally, the at least the support section and the anchoring section are flexible. Optionally, the at least the node is flexible. In an embodiment of the invention, the apparatus further comprises a device displacer.

Optionally, the device displacer is attached to the support section. In an embodiment of the invention, the apparatus further comprises an applicator adapted to insert the apparatus into a vagina. Optionally, the apparatus is symmetrically arranged around a central axis. Optionally, the length of the apparatus is 60 mm or less.

There is thus provided in accordance with an exemplary embodiment of the invention, an apparatus for treating urinary incontinence, comprising: a node; a support section adapted for providing urethral support attached to the node; and, an anchoring section adapted for resisting movement of the apparatus attached to the node opposite the support section; wherein at least the support section is pre-tensioned with a pre-tensioning element immediately prior to insertion of the apparatus into a vagina. Optionally, the pre-tensioning element is a flared barb. Optionally, the pre-tensioning element is a pre-tensioning spar on which a plurality of pre-tensioning flared barbs are located. In an embodiment of the invention, the apparatus further comprises an orifice adapted to permit, at least in one direction, passage of the pre-tensioning element therethrough. Optionally, the at least a portion of the apparatus is flexible.

There is thus provided in accordance with an exemplary embodiment of the invention, a method for preserving shelf life and performance characteristics of a urinary incontinence treating device, comprising: placing the device in a storage configuration within an applicator; transitioning the device from the storage configuration to a deployment configuration within the applicator just prior to deployment. Optionally, the transitioning further comprises selecting from one of a plurality of deployment configurations.

There is thus provided in accordance with an exemplary embodiment of the invention, an apparatus for treating urinary incontinence, comprising: a node; at least two poles connected by the node for providing anchoring and supporting to the apparatus during urinary incontinence treatment. Optionally, one pole supports at least one of a urethra, a bladder neck or a bladder. Optionally, one pole anchors the apparatus. Optionally, each pole is provided with at least one band with at least one anchoring or supporting feature. Optionally, the anchoring or supporting feature is a prong. Optionally, the at least one anchoring or supporting feature is flexible. Optionally, the at least one anchoring or supporting feature is provided with an end protector. Optionally, the at least one band is interchangeable with at least one other band. Optionally, the at least one band is rotatable about the pole the at least one band is provided to.

There is thus provided in accordance with an exemplary embodiment of the invention, an apparatus for treating urinary incontinence, comprising: a node; and, a plurality of anchoring and support features radiating from the node wherein the apparatus is adapted to render urinary incontinence in any orientation. Optionally, the anchoring and support features are prongs. Optionally, the anchoring and support features are flexible. Optionally, the anchoring and support features are provided with end protectors.

There is thus provided in accordance with an exemplary embodiment of the invention, an apparatus for treating urinary incontinence, comprising: a pivot point; and, a plurality of lever units connected to the apparatus at the pivot point. Optionally, the at least one of the plurality of lever units provides anchoring and support to at least one of a urethra, a bladder neck or a bladder. Optionally, the plurality of lever units are arranged symmetrically around a central axis of the apparatus. Optionally, the at least one lever unit is flexible.

There is thus provided in accordance with an exemplary embodiment of the invention, an applicator for the insertion of an apparatus for urinary incontinence treatment, comprising: an enclosure adapted to transition from a storage configuration to a deployment configuration such that in the storage configuration, at least a support section of the apparatus is substantially un-compressed; and, a plunger for pushing the apparatus out of the enclosure during deployment.

In any of the embodiments of the invention described herein, the apparatus comprised of a material which alters its material properties when inserted into a vagina. Optionally, the material is viscose. Optionally, the material is a solid absorbent. Optionally, the material is a laminate.

In any of the embodiments of the invention described herein the apparatus provides pharmaceutical treatment to a vagina.

In an exemplary embodiment of the invention, there is provided an apparatus for treating urinary incontinence, comprising:

(a) a plurality of rods, each rod characterized by a proximal section, a midsection and a distal section;

(b) an anchor base and a support base, the anchor base and the support base adapted to engage and retain each rod at the proximal section and the midsection respectively; and (c) an expansion mechanism comprising a hub and a spoke for each rod, (i) each spoke adapted at a distal end thereof to engage and retain a distal section of a rod; and (ii) the hub adapted to contact a neck of the support base.

Optionally, the apparatus is normally open so that the spokes extend the distal sections of the rods radially outwards with respect to an axis defined by the support base and the anchor base.

Optionally, the rods are formed of tubing.

Optionally, the hub engages the neck.

In any of the embodiments of the invention described herein, the apparatus comprises a cover and a removal device connected to one another so that activation of the removal device causes contraction of the cover.

In any of the embodiments of the invention described herein, the cover and removal device are constructed of the same unitary piece of material.

In any of the embodiments of the invention described herein, the cover and removal device are constructed of a non-woven material (e.g. nylon).

In any of the embodiments of the invention described herein, a portion of the cover can be fashioned into a string, the string serving as the removal device.

Optionally, the string is a braided string.

In any of the embodiments of the invention described herein, the apparatus is of a size similar to a menstrual tampon.

In any of the embodiments of the invention described herein, the support member is provided with a structure adapted to receive said urethra.

Optionally, the structure is located at a mid-urethral position.

Optionally, the support is provided substantially only for a portion of said mid-urethral region.

In any of the embodiments of the invention described herein, the apparatus is adapted to be self-aligning about a portion of a urethra regardless of the rotational angle of insertion.

In any of the embodiments of the invention described herein, the apparatus is rotationally symmetric.

In any of the embodiments of the invention described herein, the apparatus is adapted to allow substantially uninterrupted vaginal fluid flow in a vagina.

In any of the embodiments of the invention described herein, the apparatus is integrally formed.

In an exemplary embodiment of the invention, there is provided a system for inserting apparatus for treating urinary incontinence comprising:

an apparatus according to any of the embodiments of the invention described herein; and an applicator coupled to said apparatus for facilitating insertion of the device into the vagina.

Optionally, the applicator maintains the support member and an anchoring member in a first collapsed position, while removal of the device from the applicator transitions the members from said collapsed position to a second expanded position. Optionally, the applicator further comprises a plunger.

In an exemplary embodiment of the invention, there is provided a method of using apparatus for treating urinary incontinence, comprising:

inserting said apparatus into a vagina;

placing said apparatus in said vagina so that a support member located on said apparatus does not apply direct pressure to a urethra located anterior to said vagina; and, removing said apparatus when done using.

In an exemplary embodiment of the invention, there is provided a method of forming a cover for an intravaginal device, the method comprising:

(a) cutting a piece of material to a desired shape, the shape including fold lines, welding seams and braid-able tails;

(b) folding the piece of material along the fold lines and welding the welding seams to produce the cover.

Optionally, the method includes braiding the tails to form a removal apparatus for the intravaginal device.

BRIEF DESCRIPTION OF THE FIGURES

Non-limiting embodiments of the invention will be described with reference to the following description of exemplary embodiments, in conjunction with the figures. The figures are generally not shown to scale and any measurements are only meant to be exemplary and not necessarily limiting. In the figures, identical structures, elements or parts which appear in more than one figure are preferably labeled with a same or similar number in all the figures in which they appear, in which:

FIG. 3A is a schematic of a vagina in its natural state;

FIG. 3B is a schematic view of a device rendering incontinence treatment using colpo-distension bilateral flattening, in accordance with an exemplary embodiment of the invention;

FIG. 3C is a schematic view showing how the curvature of the vagina can be generalized into three planar sub-sections indicated by the three arrows;

FIG. 3D is a schematic view of a device rendering incontinence treatment using colpo-distension longitudinal flattening, in accordance with an exemplary embodiment of the invention;

FIGS. 9A-9E are cross-sectional views of (A) components of an incontinence treating device, (B) the top of a plunger, (C) the bottom of an insert, (D) the device in an applicator and (E) the device in a deployed configuration, in accordance with an embodiment of the invention;

FIGS. 11A-11B are cross-sectional views of an incontinence treatment device (A) in an applicator and (B) in a deployed configuration, in accordance with an embodiment of the invention;

FIGS. 16A-16E are side views and side cross-sectional views of a device for treating incontinence (A) in a deployment configuration, (B) a cross-sectional view as indicated in FIG. 16A, (C) during removal, (D) in a full removal configuration and (E) in semi-cross-section, in an applicator, in accordance with an embodiment of the invention;

FIGS. 17A-17B are cross-sectional views of an applicator (A) in a storage configuration and (B) in a deployment configuration, in accordance with an embodiment of the invention;

FIGS. 19A-19C are plan views of a cover for an apparatus according to an exemplary embodiment of the invention;

FIGS. 19D-19E are perspective and cutaway views respectively of a cover for an apparatus according to an exemplary embodiment of the invention;

FIG. 20A is a plan view of a cover formed from a single piece of material for an apparatus according to an exemplary embodiment of the invention;

FIGS. 20B-20C are perspective and cutaway views respectively of a cover for an apparatus applied to the apparatus according to an exemplary embodiment of the invention;

FIG. 21A is a plan view of a cover formed from a single piece of material for an apparatus according to an exemplary embodiment of the invention;

FIGS. 21B-21C are perspective and cutaway views respectively of a cover for an apparatus applied to the apparatus according to an exemplary embodiment of the invention;

DETAILED DESCRIPTION OF EXEMPLARY EMBODIMENTS

Introduction

Multiple aspects of treating feminine incontinence are described in this application, examples of which include: 1) principles of operation (FIGS. 1A-3D); 2) exemplary device embodiments (FIGS. 4A-16E); 3) material and manufacturing considerations; 4) an exemplary applicator (FIGS. 17A-B); and 5) exemplary methods of use. Section headings are used throughout in order to orient the reader to the general subject matter of the section; however it should be understood that the headings are not intended to limit the description thereunder.

Exemplary Principles of Operation

In some embodiments of the invention, treatment of incontinence is effectuated by deploying a device which utilizes at least one of SUTFS, colpo-elevation or colpo-distension, described in more detail below. In some embodiments of the invention, more than one of these principles of operation are used in combination by a device in order to treat incontinence.

A first exemplary principle of operation is by providing SUTFS, for example Mid-Urethral Tension Free Support (MUTFS), which is the fundamental principle of operation of a TVT ("Tension Free Vaginal Tape") operation, described above in the Background section. It should be understood that MUTFS is a subset of SUTFS and that incontinence treatment can possibly be performed by supporting the urethra anywhere along its length. SUTFS treatment is not new per se, however, the apparatus and method for providing such treatment, as described below, is new.

Figure 1A:
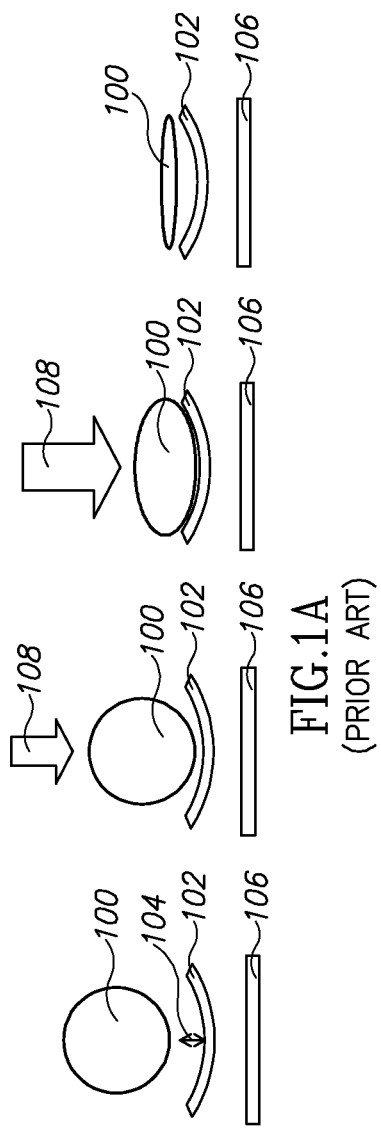
FIG. 1A is a schematic progressive frame view of a prior art TVT operation.

Referring to FIG. 1A, a progressive (left to right), segmented schematic of the operation of the TVT operation is shown, according to the prior art. The first segment shows a urethra 100 prior to a stressful event. An implanted mesh tape 102 of the TVT operation is positioned some distance 104 below urethra 100. The vaginal wall 106 of the patient is located below mesh tape 102. The second segment, moving left to right, shows the initiation of a stressful event, such as coughing or sneezing. Pressure 108 begins to compress urethra 100 pushing urethra 100 down towards to mesh tape 102. The third segment shows what happens as the stressful event intensifies, wherein pressure 108 builds, compressing urethra 100 against mesh tape 102 and causing a constriction of urethra 100. The fourth segment shows a constricted urethra 100 as a result of increased and sustained pressure exerted on it caused by the stressful event. Typically, after the stressful event is over, urethra 100 returns to the condition depicted in FIG. 1A. After a successful TVT operation, the constriction of urethra 100 is sufficient to reduce or prevent involuntary leakage.

Figure 1B:
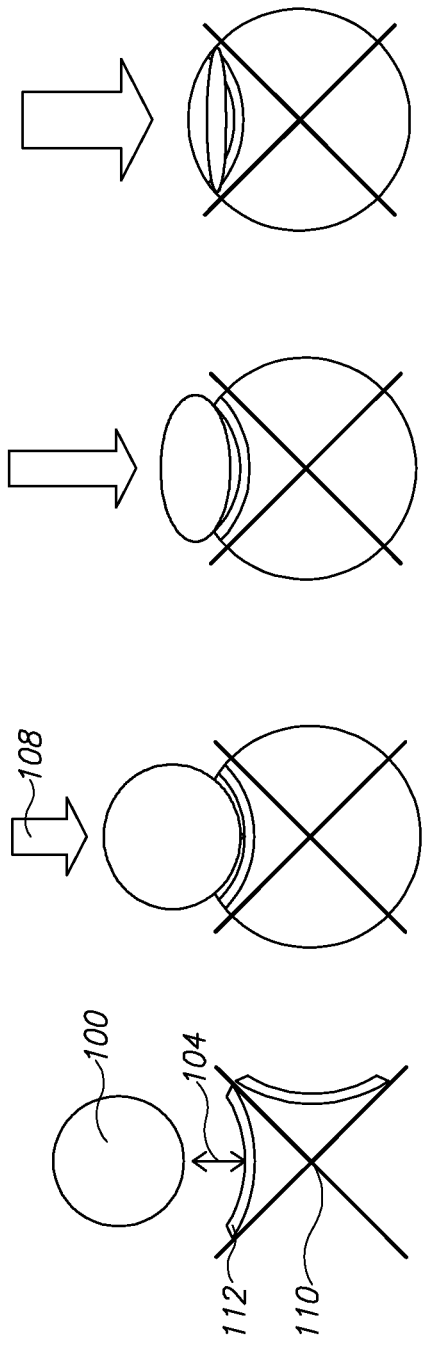
FIG. 1B is a schematic progressive frame view of a device rendering incontinence treatment using SUTFS, in accordance with an exemplary embodiment of the invention.

FIG. 1B shows a progressive, segmented schematic of the SUTFS operation of an exemplary incontinence device 110, in accordance with an embodiment of the invention. One difference in this series from the one depicted in FIG. 1A is the replacement of the embedded mesh tape 102 with an incontinence device 110 and a cover 112 located in the vagina. It can be seen that as pressure 108 is exerted on urethra 100 as a result of a stressful event, urethra 100 becomes compressed by device 110 and cover 112: cover 112 functioning like a hammock suspended from the structure of device 110. In an embodiment of the invention, incontinence is treated by providing enough support to urethra 100 such that it can be constricted enough to reduce or prevent involuntary leakage during the stressful event.

Figure 2A:
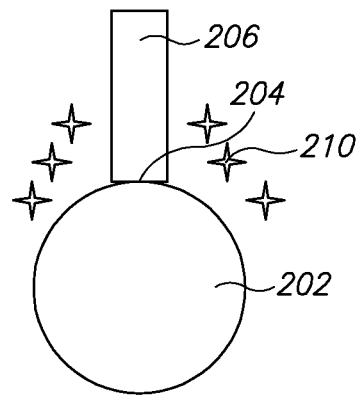
FIGS. 2A-2C are schematic views of a device rendering incontinence treatment using colpo-elevation, in accordance with an exemplary embodiment of the invention.
Figure 2B:
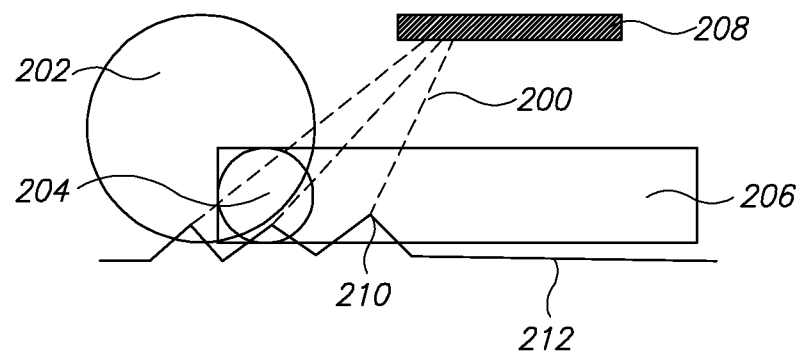

A second possible principle of operation, in accordance with an embodiment of the invention, is known as colpo-elevation, similar to the action done when performing the Burch Colposuspension operation. In this operation, details of which, according to the prior art, are depicted in FIGS. 2A-B, a vagina is grasped with 2-3 sutures 200, shown in FIG. 2B, on either side of a bladder neck 204, which are then tied to the Cooper's ligament 208, hence elevating the vaginal wall 212 upwards. An upper portion of the vagina (colpos) 212 serves as hammock to a bladder 202, the bladder neck 204 and/or a urethra 206, hence the name colposuspension. FIG. 2A shows a top view of bladder 202, bladder neck 204 and urethra 206. Elevated tissue locations 210 are shown on either side of bladder neck 204. FIG. 2B shows a lateral view of the same anatomy, but including the Cooper's ligament 208 and schematically showing sutures 200 which are used to create elevated tissue locations 210 around bladder neck 204 and provide the tissue hammock which is akin to mesh tape 102 of the TVT operation. In practice, the elevated vagina supports bladder 202, bladder neck 204 and/or urethra 206 during a stressful event, causing constriction of bladder 202, bladder neck 204 and/or urethra 206 and therefore, reducing or preventing incontinence.

Figure 2C:
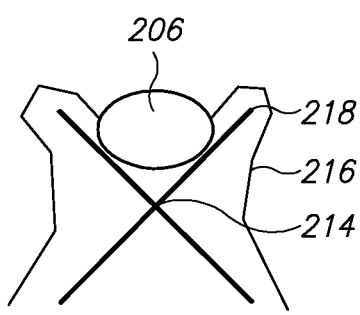

Referring to FIG. 2C, an incontinence device 214 utilizing the colpo-elevation principle of operation is shown, in accordance with an exemplary embodiment of the invention. Upon deployment of device 214 inside a vagina 216, at least the support section 218 of device 214 operates to elevate the tissue of vagina 216 adjacent to urethra 206 to provide support similar to the Burch Colposuspension operation. In an embodiment of the invention support section 218 abuts vagina 216 on either side of urethra 206 and exerts pressure upwards causing colpo-elevation.

A third possible principle of operation, in accordance with an embodiment of the invention, involves stretching the vaginal wall, called colpo-distension. Examples of how this principle can be affected include performing anterior vaginal colporrhaphy, described in the Background section above, and/or inserting a flat pessary. In an Anterior Colporrhaphy operation, loose vaginal tissue underneath the bladder and urethra is tightened by removing portions of the mucosa, hence shortening and flattening the wall. This results in better support to the bladder, bladder neck and urethra, and therefore some reduction in incontinence. FIG. 3A generally shows a vaginal wall 302 in its natural form, prior to distension by an incontinence device. A bladder 304 is shown protruding into the vagina, partially as a result of the inability of the non-stretched vaginal wall to support the weight of bladder 304. FIG. 3B shows how the vaginal wall 302 can be distended bi-laterally by an incontinence treating device 306, without surgically removing vaginal tissue, thus providing enough tension on vaginal wall 302 to prevent bladder 304 from lapsing into the vagina, in accordance with an exemplary embodiment of the invention.

Referring to FIG. 3C, an alternative method of distending the vaginal wall is shown, in accordance with an exemplary embodiment of the invention. This method takes advantage of a special longitudinal feature of the vagina, its being generally curved. It can be said that the nominal curvature of the vagina at least vaguely corresponds to three planar sub-sections 308, 310 and 312, shown in FIG. 3C. In an exemplary embodiment of the invention, device 314 for treating incontinence is inserted into the vagina which is provided with sufficient flexibility to allow device 314 to extend into at least two of the planar subsections 308, 310, 312, as shown in FIG. 3D. Optionally, flexibility is provided to device 314 via a flexible node 316. Optionally, flexibility is provided to device via a flexible support section 318 and/or an anchoring section 320. In some embodiments of the invention, the curved nature of the vagina and this device 314 causes the anterior portion of support section 318 to produce an elevated tension on an anterior section of vaginal wall 302. That tension will be directed backwards and upwards (dotted arrow 322), in some embodiments of the invention, producing longitudinal distension (as opposed to the bilateral distension described in the FIG. 3B). Longitudinal distension of vaginal wall 302 provides support for at least one of a bladder 324, a bladder neck 326 or a urethra 328. In an embodiment of the invention, anchoring section 320 operates similarly to other anchoring sections described herein and/or in related applications such as PCT/IL2006/000346.

Exemplary Incontinence Treating Device

Some of the various embodiments of apparatus according to the present invention provides devices for the treatment of urinary incontinence in females. These devices are adapted to be disposable, worn only for a short period of time and then discarded and replaced with a new device (if needed). Alternatively, the device is recycled for use by sterilizing it in between uses. The devices of the present invention are simple and easy to use, and are optionally inserted effortlessly in the same user-friendly and familiar manner that a tampon is inserted into the vagina during menstruation. As opposed to large and intrusive devices of the prior art, the devices of the present invention are comfortable, and, once inserted, the woman need not think about it again until it is to be removed.

These devices optionally utilize at least one of the principles of operation described above in order to perform this function. While not necessarily true for every embodiment, these devices generally: 1) are at least partially flexible; 2) provide intravaginal anchoring and/or urethral support, optionally independent of one another, to the user; 3) are insertable by the user using an applicator; 4) are removed by the user with a removal device, such as a string; 5) are rotationally symmetric; 6) are variable in dimension and/or shape depending on storage, insertion, treatment and/or removal considerations; 7) do not interrupt nominal (i.e. healthy) activities of the body, such as voluntary urination, bowel movements, vaginal secretion and/or body movements; 8) are comfortable to use and reduce the likelihood of necrosis or pressure ulcers over other incontinence device designs; 9) are relatively small in comparison to other incontinence device designs; and 10) are inexpensive to mass produce. In addition, although certain nomenclature is used (e.g. "anchoring" and "support") it should be understood that these are for ease of reference only, and in some embodiments of the invention an "anchoring" section could be used for providing support and/or vice versa.

Figure 4A:
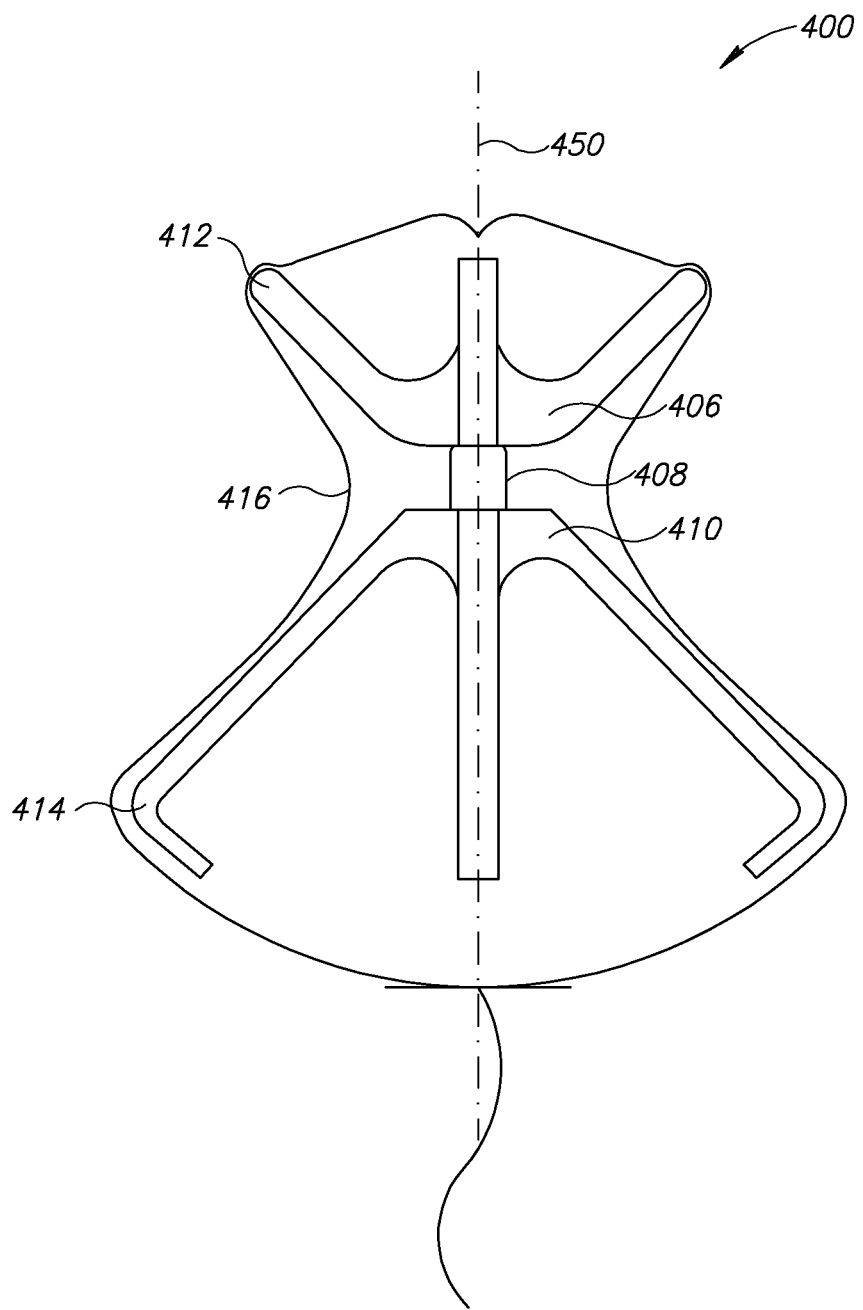
FIGS. 4A-4C are cross-sectional views of (A) an incontinence treatment device, (B) the device in an applicator and (C) the device being removed from the vagina, in accordance with an exemplary embodiment of the invention.

Referring to FIG. 4A, a profile view of an exemplary embodiment of an incontinence device 400 is shown. Device 400 is arranged around a central axis 450 and generally divided into three parts. Optionally, device 400 is symmetrically arranged around central axis 450. A top section 406 is provided which serves as the "anchoring" section, for stabilizing the device 400 within the vagina. There are two types of anchoring, axial anchoring which acts to reduce motion in the direction along the central axis of the vagina, and radial anchoring which acts to reduce rotational motion around the central axis of the vagina, and radial anchoring which acts to reduce side-to-side motion or motion substantially perpendicular to the central axis of the vagina. A bottom section 410 is provided which serves as the "supporting" section, for generating urethral, bladder and/or bladder neck support. In some embodiments of the invention, support is generated at a mid-urethral location. In some embodiments of the invention, the bottom supporting section 410 provides at least one form of anchoring to help anchor device 400 in position. In some embodiments of the invention, the entire length of device 400 is between 30 mm and 60 mm long. Optionally, device 400 is larger or smaller depending on the individual needs of the patient. In an embodiment of the invention, anchoring section 406 has a radius of up to 40 mm. In some embodiments of the invention, the support section 410 has a radius of up 40 mm or less. Optionally, a smaller radius of the support section contributes to a reduction in undesirable sideffects without making a substantial difference in efficacy of the apparatus.

An intermediate section 408 is generally provided which acts as a "node" and which connects anchoring 406 and supporting 410 sections. The node 408 in this embodiment has a length which is only a small portion of the overall length of device 400; however in other embodiments it may be longer, even up to the full overall length of the device. In some embodiments of the invention, the length of the node is less than 15% of the entire length of the device. In some embodiments of the invention, the length of the node is less than 20% of the entire length of the device. In other embodiments of the invention, the length of the node is less than 30% the entire length of the device. In some embodiments of the invention, a node which is short relative to the entire length of the device allows for more flexibility in varying the stiffness, the comfort, and the size of device 400. Optionally, the node is not provided with one axis longer than the other, for example, its overall dimensions are similar in three dimensional space (e.g. a sphere or a cube). In an exemplary embodiment of the invention, a small node in relation to the overall length of the device allows for greater control over the behavior of the anchoring and support arms, described below. Optionally, the center of the node 408 is located on and/or is inline with the central axis 450. Optionally, node 408 is at least partially flexible. Optionally, node 408 is rigid. In some embodiments of the invention, node 408 does not directly support any of the pelvic organs and/or apply pressure to the vaginal wall, due to it being suspended in the vagina between support and anchoring sections of device 400. In some exemplary embodiments of the invention, the intermediate section (e.g. 316 in FIG. 3D) allows for flexibility of the device in all aspects and axes. Optionally, this flexibility contributes to separation between the two poles so that each pole may function separately and/or so that each pole poles can act in a different plane.

The elements of the device 400 function as an internal support structure for a cover 416, described in more detail below, in some embodiments of the invention. It should also be noted that for certain women, the described devices herein can also be used as a treatment for prolapse. For example, arms which are expanded to a certain diameter for incontinence treatment can optionally expand to a larger diameter for prolapse treatment. For example, prolapse treating configurations optionally exhibit a diameter when the device is in place of up to 100 mm.

In an exemplary embodiment, the anchoring section 406 and the supporting section 410 each have four (4) arms 412 and 414, respectively. In an exemplary embodiment of the invention, four arms are provided to each section in which two generally exert pressure towards the interior vaginal wall, adjacent to the bladder and urethra, and two generally exert pressure towards the vaginal posterior wall adjacent to the rectum. The two support arms which exert pressure towards the bladder may fit within natural slots on either side of the urethra, in some embodiments of the invention. Optionally, the anchoring and supporting sections are provided with more or fewer arms. For example, the anchoring section could have more arms if there is concern about unwanted movement of device 400. In an embodiment of the invention, the ends of the arms 414 of at least the supporting section are biased inwards towards the central axis 450. In other embodiments of the invention, the arms are provided at varied angles with respect to the node 408 and/or each other. Optionally the arms 412 and 414 are flexible or rigid and are constructed of a biocompatible material. Optionally, the flexibility of arms 412, 414 varies along the length of the arms, for example exhibiting more flexibility towards the ends than near node 408 (which would provide more comfort for the wearer). In some embodiments of the invention, the cross-section of arms 412, 414 varied along the length of the arm, for example an arm may have a larger cross-section closer to node 408, or may be shaped differently. As another example, the cross-section of arms 412, 414 could be designed so that they collapse in a particular manner upon the application of force by a removal device, described in more detail below. In some embodiments of the invention, arms 412, 414 are comprised of at least one of silicone, nylon, polyurethane, foam polystyrene, metal, or an over molding of two materials. In an exemplary embodiment of the invention, the anchoring element does not apply significant pressure to the wearer's vagina and/or urethra, thereby enhancing comfort. In some embodiments of the invention, other structure is provided instead of arms which is capable of supporting the urethra, in the case of the support section, or preventing the device from unintentionally moving, in the case of the anchor section. For example, at least one cone, protrusions, and/or extensions attached to the node could be used for anchoring and/or support.

In an embodiment of the invention, device 400 can be inserted into the vagina without the need for a specific orientation about its central axis 450. Irrespective of any rotation of an applicator, when inserted intra-vaginally, device 400 will position itself properly in the vagina so that edges of two of its support arms will rest on both sides of at least the urethra, bladder neck and/or bladder. In an embodiment of the invention, this occurs because of the tendency of device 400 to locate its arms in places of least pressure. Since the urethra somewhat bulges into the vagina at its anterior wall, in the event one support arm is inserted underneath the urethra, device 400 would become unstable and rotate so that two arms would be situated in the vaginal recesses adjacent to both sides of the urethra.

The anchoring arms of the device prevent the device from moving unintentionally out of position. In an exemplary embodiment of the invention, the arms are flexible. This flexibility enhances the anchoring arms' 412 ability to prevent motion of the device 400 further into the vagina. As force strives to exert itself on device 400, and move it into the vagina, flexible anchoring arms 412 tend to spread apart. This spreading action of anchoring arms 412 increases the friction between device 400 and the vaginal wall, prevent movement. While arms 412 are flexible, it should be noted that they are rigid enough to prevent unwanted motion of device 400 towards the entrance of the vagina. Optionally, the arms are rigid but node 408 is flexible, the node thus providing flexible anchoring and support. Optionally, both arms 412 and node 408 are flexible. Movement towards the vaginal opening is resisted by arms 412 which position themselves close to (e.g. just on the posterior side of) the vaginal opening, at a hump located in the vagina. These features work independently from and in conjunction with the tenting behavior of the vaginal walls described above, which also helps to maintain the device in place.

In some exemplary embodiments of the invention, similar considerations concerning flexibility apply to support arms 414.

An additional feature of anchoring arms 412, an embodiment of the invention, of device 400 is that they operate substantially independently from support arms 414 (like an independent suspension in a car). This reduces the amount of pressure applied to the urethra by device 400. Alternatively or additionally, the remote position of the anchoring arms 412 in relation to the support section 410 is calculated so that the anchoring arms 412 can position themselves just on the posterior side, of the vaginal opening, while supporting arms 414 provide support to the bladder, bladder neck and/or the urethra. Optionally, support arms 414 can position themselves close to the vaginal opening and provide support to the bladder, bladder neck and/or the urethra. Such a configuration increases comfort to the wearer, prevents unnecessary damage to the tissues adjacent to device 400, increases the anchoring function of the device 400, and in some embodiments of the invention allows the wearer to void voluntarily without having to remove the device to urinate.

Arms 412 of anchoring section 406 force device 400 to remain in situ within the vagina, unable to substantially move inwards or outwards, or to rotate, in some embodiments of the invention. One reason this occurs is as a result of the special tendency of vaginal walls to collapse and form an occluded lumen. The arms of the device 400 cause "tenting" of the walls on top of them with resultant sagging of the walls around the node 408, thereby stabilizing the device 400. The arms 414 of the supporting section 410 optionally cause elevation of the tissues around the urethra, acting as a hammock. This hammock supports the urethra in a tension free manner, using the SUTFS principle of operation or with at least slight tension as with the colpo-elevation principle of operation. With respect to the SUTFS, a woman who leaks urine during a stressful event (when abdominal pressure rises during coughing, sneezing, etc.), the urethra sags down but meets the hammock in its mid part. The meeting of the urethra and the hammock causes a reduction of the diameter of the lumen of the urethra with subsequent possibility of an elevation of the intra-urethral pressure while maintaining urinary continence. In some embodiments of the invention the radiating support arms 414 of device 400 create an overall device diameter of 25 mm to 55 mm within the vaginal cavity. Optionally, the diameter is larger or smaller depending on the individual needs of the patient. In some embodiments of the invention, the support provided by arms 414 is equal. Optionally, the support provided by arms 414 is varied, for example in oppositely situated pairs.

In an exemplary embodiment of the invention, the anchor section arms 412 resist motion of the device towards the uterus because the arms increase their angle to the node 408. This effective increase in diameter operates to counteract the motion of the device further into the vagina. In some embodiments of the invention, anchor element arms 412 are provided with a large angle to the node to enhance this anchoring effect.

In some embodiments of the invention, materials which resist the stresses of storage are use to reinforce the support or anchoring arms of device 400. For example, using a material such as stainless steel, optionally in the form of springs, within the arms of the device, will help the arms maintain their effectiveness.

Figure 4B:
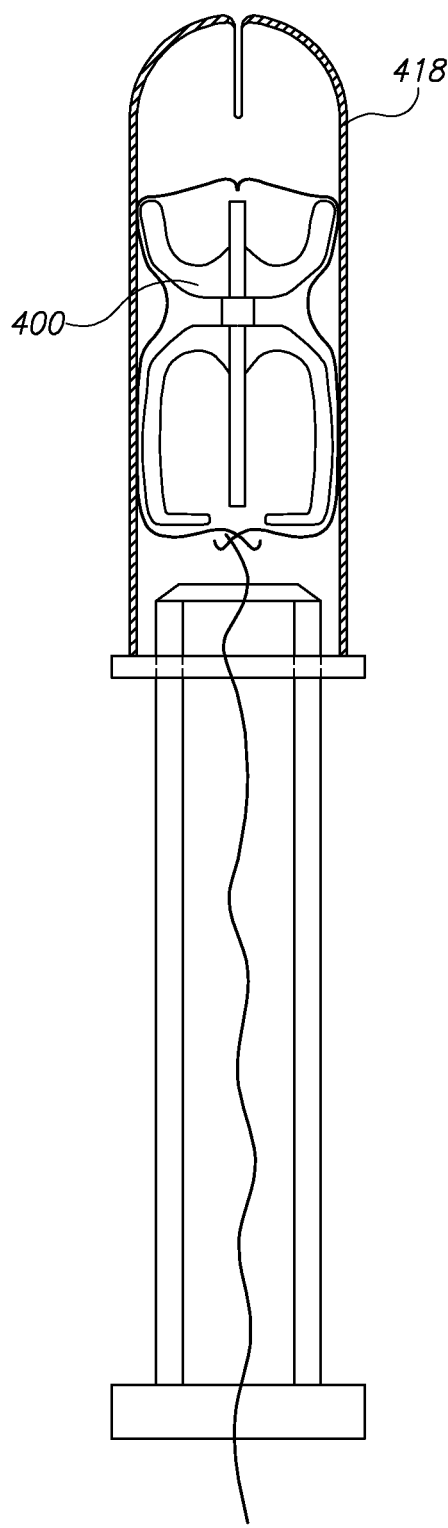

Referring to FIG. 4B, device 400 is shown within an applicator 418 prior to insertion and deployment into the vagina of a user. Optionally, applicator 418 is any of the applicators described in PCT/IL2005/000304, U.S. Application Ser. No. 60/719,422, U.S. Application Ser. No. 60/762,059 and PCT/IL2006/000346, the contents of which are herein incorporated by reference.

In an exemplary embodiment of the invention, applicator 418 is not necessary for the deployment of an incontinence device. For example, any of the incontinence devices described herein could be inserted manually by the user. In some embodiments of the invention, manual insertion of an incontinence device is assisted by providing an additional cover, between cover 416 and the incontinence device, which tightly constricts (i.e. reduces its radial profile) the incontinence device for easier insertion into the vagina. In an embodiment of the invention, the additional cover is manufactured from nylon or non-woven material or any other mesh. The additional cover is provided with a string or the like for removing the additional cover from the device, inside the vagina at the time of deployment. In an embodiment of the invention, tearable perforations are located in the additional cover such that when force is applied to the string, the perforations tear, releasing the constriction on the incontinence device and allowing for the removal of the additional cover from inside cover 416 and the vagina. It should be noted that the perforations are adapted not to tear from the force of the device wanting to radially expand, but to tear upon the application of sufficient force on the string.

In some exemplary embodiments of the invention, the device is cast from a single piece (Monoblock) and in other exemplary embodiments of the device the anchor section and support section are provided as separate pieces (bi-polar) which are attached to form the device. Optionally, each pole is additionally constructed of two or more pieces.

Figure 4C:
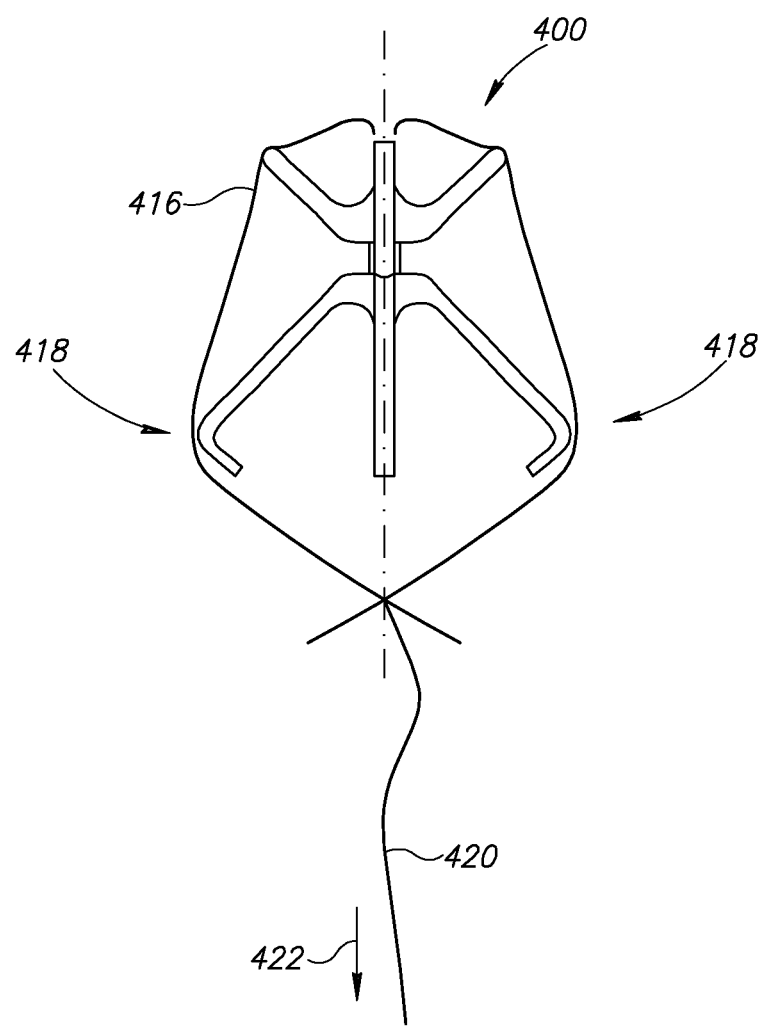

FIG. 4C shows the device during removal, wherein a removal device 420, such as a string, is pulled in a direction 422 away from the cervix and towards the introitus of the vagina. In some embodiments of the invention, cover 416 assists with removal of the device from the vagina. First, in some embodiments of the invention, cover 416 reduces friction between the incontinence device 400 and the vaginal wall. Second, cover 416 is optionally attached to removal device 420. Pulling the removal device 420 causes tensioning of cover 416 in some embodiments of the invention. Tensioning of cover 416 causes the collapse of the arms and also results in straightening of the vaginal walls. The straightening of the vaginal walls reduces the tent-like effect described above and relieves tension applied to the device, allowing for an easy and smooth removal of the device from the vagina. In addition, pulling on removal device 420 causes the arms 414 to fold slightly towards the central axis 450 as a result of force 418 applied to them by cover 416, thereby reducing the radial diameter of device 400 and allowing for an easy and smooth removal of the device 400 from the vagina. In some embodiments of the invention, possibly more than one removal device type structure is provided to device 400. For example, removal device 420 is provided and used as described, but another removal device-like structure could be provided for assisting with manipulating device 400 within the vagina and/or within applicator prior to deployment. Optionally, removal device 420 is comprised of a non-absorbent material. Optionally, removal device 420 is manufactured at the same time as and/or with node 408. Cover 416 is optionally any of the covers described in PCT/IL2005/000304, U.S. Application Ser. No. 60/719,422, U.S. Application Ser. No. 60/762,059 and PCT/IL2006/000346. In some embodiments of the invention, cover 416 is smooth. Optionally, cover 416 is non-woven. Optionally, cover 416 is comprised of nylon. Optionally, cover 416 and removal device 420 are constructed of the same unitary piece of material. In some embodiments of the invention, cover 416 is flexible. In some embodiments of the invention, cover 416 is stitched and/or sutured together. Optionally, the stitches and/or sutures are inside cover 416, opposite the vaginal wall. The removal device 420 assists with the removal of the device in a number of ways.

Figure 5:
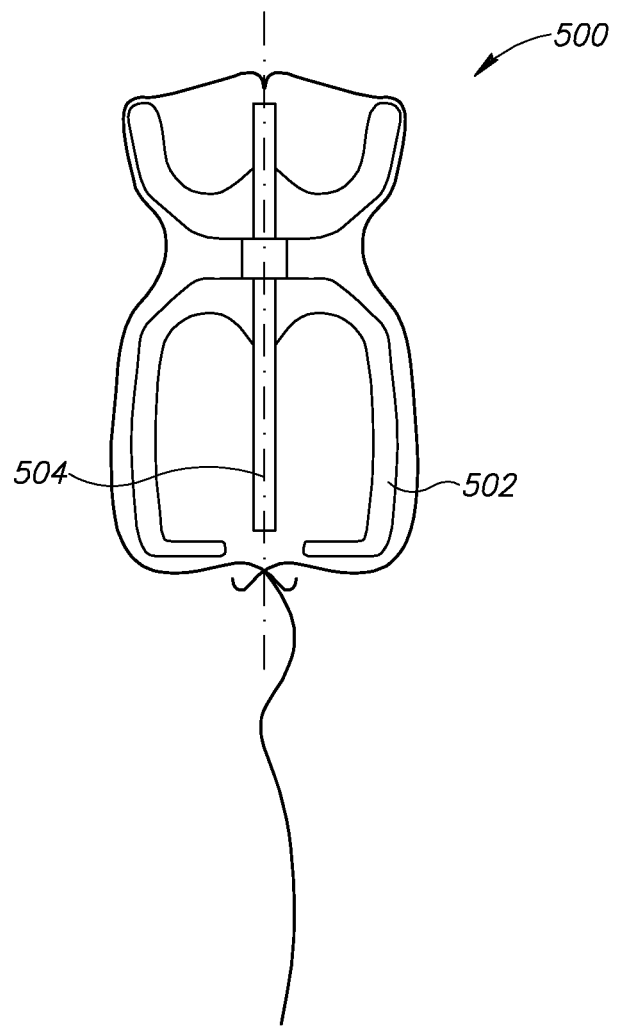
FIG. 5 is a cross-sectional view of an incontinence treating device in accordance with an exemplary embodiment of the invention.

FIG. 5 show a device 500 for treating incontinence wherein two arms 502 of a support section are longer than the other two arms 504 of the support section, in accordance with an exemplary embodiment of the invention. In an embodiment of the invention, two shorter arms 504 are provided to device 500 to reduce the radial dimension of support section 506 while inside the applicator and during removal from the vagina. In some embodiments of the invention, support arms are folded towards the central axis of the device while in the applicator and thus, when the arms are converged inward biased ends of the arms abut each other, preventing more radial contraction than could be provided with staggered arm endings. Therefore, in some embodiments of the invention two arm 504 ends are staggered so they fall behind the other two arm 502 ends, creating an overall radial diameter within the applicator and during removal from the vagina which is smaller than a non-staggered arm configuration.

Exemplary Devices with an Insert for Treating Incontinence

Various incontinence device embodiments are described herein, many of which utilize inserts to assist with radial expansion of at least the support section of the incontinence device. It should be noted that many of these inserts optionally have multiple stop positions which correspond to multiple incontinence device configurations. Specific positions are optionally selected depending on the needs of the patient.

FIGS. 6A-C, 7A-B, 8A-C, and 9A-E show different exemplary embodiments of device for treating incontinence which use inserts. Inserts are generally used to radially expand at least the support section of the device and/or to provide the support section with additional support against pressure exerted on the support section by the vaginal wall. In addition, removable inserts such as those described herein, enable the incontinence devices to render effective incontinence treatment while avoiding some of the storage stresses that would normally come with devices which render such effective treatment and/or to allow for a transition to an easier to remove configuration. In an exemplary embodiment of the invention, storage stresses are avoided because the insert is stored in a non-deployed position, the non-deployed position not exerting treatment level radial pressure on the support section. It should be understood, that the inserts and device configurations described in reference to FIGS. 6A-C, 7A-B, 8A-C, and 9A-E are exemplary only, and that different configurations are optionally used depending on the needs of the patient. For example, the insert is optionally shaped to urge the support arms to different radial expansion diameters, as measured from a central axis of the device. Optionally, the insert is provided with a plurality of removably locking positions on the device, with each locking position corresponding to a slightly different configuration, such as radial expansion diameter, of the device.

In some exemplary embodiments of the invention, at least the support section is manufactured so that it exhibits a bias towards a central axis of the device. In such an embodiment, it is expected that storage (e.g. storage in an applicator) in a contracted configuration imposes less stress on the device than if it was manufactured with the support section biased in an expanded, incontinence treating configuration. The support section is optionally placed in an expanded configuration during or after deployment, such as by using the inserts described herein. In an exemplary embodiment of the invention, it is conceived that removal of the insert causes the support section to return to the contracted state for easy removal from the user's vagina. Many of the exemplary incontinence devices described herein are optionally manufactured with anchoring and/or support sections (for example, the arms of the sections) being biased in a contracted, non-deployed configuration.

Figure 6A:
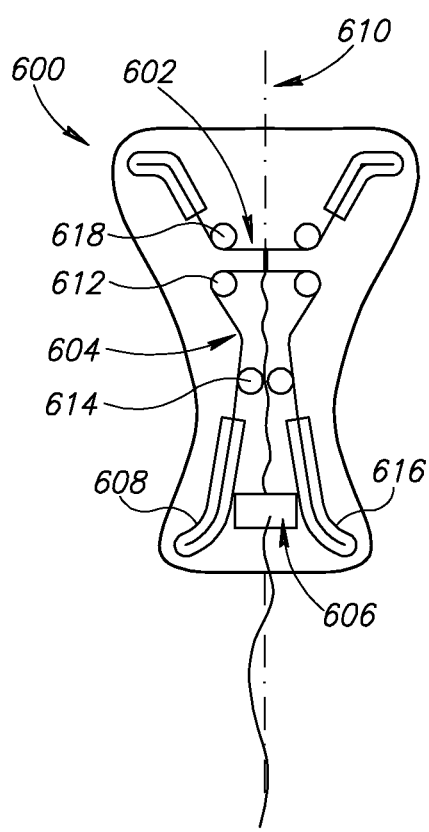
FIGS. 6A-6C are cross-sectional views of an incontinence treating device (A) in a removal configuration, (B) in a deployed configuration and (C) in an applicator, in accordance with an exemplary embodiment of the invention.

In an exemplary embodiment of the invention, the devices for treating incontinence which are depicted in FIGS. 6A-C, 7A-B, 8A-C operate in similar manner. Therefore for brevity's sake, the device depicted in FIGS. 6A-C will be described and only selected differences between the devices of FIGS. 7A-B, 8A-C and the device of FIGS. 6A-C will be described thereafter. Referring to FIG. 6A, a cross-section of an incontinence device 600 is shown which is provided with a spring biasing, in accordance with an exemplary embodiment of the invention. Device 600 is comprised of at least an anchoring section 602, a support section 604 and an insert 606, in an embodiment of the invention. Optionally, device 600 includes a central node, providing an intersection and/or bridging structure between anchoring section 602 and support section 604. In some exemplary embodiments of the invention, support section 604 is comprised of biasing spring elements 612, at least some of which bias support arms 608 towards a central axis 610 of device 600. In some embodiments of the invention, support arm spring elements 614 are provided to support arms 608 to provide an additional pivot point, shown in more detail in FIG. 6B. Optionally, support arm spring elements 614 are arranged outwardly on support arms 608 to provided easier movement of an insert 606 in device 600. In some embodiments of the invention, support arms 608 are provided with end protectors 616 to minimize damage to the vaginal tissue and to improve comfort during use. In an exemplary embodiment of the invention, anchoring section 602 is similar to the support section 604, being provided with anchor arm spring elements 618 and end protectors. Optionally, the end protectors are made from flexible and/or compressible material, such as rubber or plastic. Optionally, the end protectors are harder or softer than arms 608. In some embodiments of the invention, arms 608 and/or end protectors are angled inwards, away from the vaginal wall. In some embodiments of the invention, the anchoring section 602 and the support section 604 are provided with 4 legs each. Optionally, more or less legs are used depending on the needs of the patient and the desired effects to be achieved. Optionally, support section 604 and/or anchoring section 602 are comprised of metal. Alternatively or additionally, support section 604 and/or anchoring section 602 are comprised of plastic.

Optionally the two poles are constructed of the same materials (such as metal or plastic) or the anchoring pole may have a different configuration from the support pole (e.g. the exemplary all silicone embodiment described hereinabove; see FIGS. 4A, 4B and 4C).

Figure 6B:
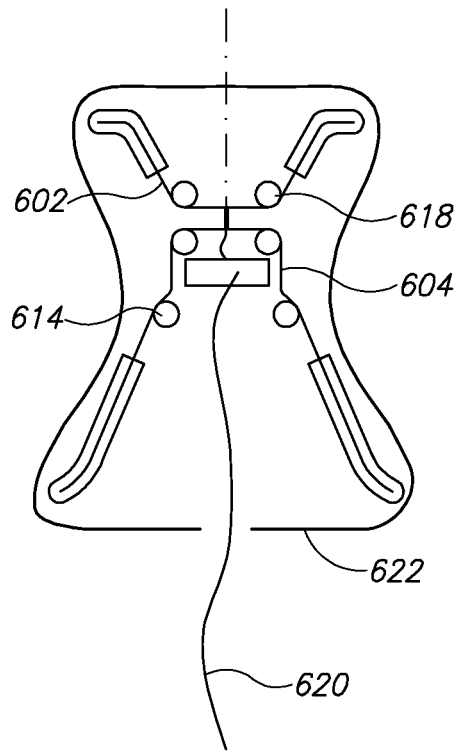

In an exemplary embodiment of the invention, support section 604 is formed such that it maintains a nominal compressed configuration (which is biased towards central axis 610 of device 600), but is flexible enough to be placed into an expanded configuration by insert 606 which abuts support section 606 (as shown in FIG. 6B). In some exemplary embodiments of the invention, support section 604 applies a modicum of support when in the compressed configuration. Optionally, support section 604 is a leaf spring which is biased towards a central axis of device 600.

When deployed, shown in FIG. 6B, insert 606 is positioned within support section 604 which counters the natural bias of the support section 604 towards central axis 610, in accordance with an embodiment of the invention. In an exemplary embodiment of the invention, insert 606 is maintained within support section 604 by the compressive force applied to it by the inwardly biased support section 604. In an embodiment of the invention, support section 604, when outwardly influenced by insert 606, provides support to at least one of the bladder neck, the bladder or the urethra in order to combat incontinence in accordance with one of the principles of operation described above. When deployed in the vagina to treat incontinence, support arm spring elements 614 and/or anchor arm spring elements 618 flex to enable device 600 to conform to the irregular and varying vaginal wall of the user, thereby enhancing comfort. In an embodiment of the invention, removal of device 600 is via downward force on a removal device 620 away from cervix and towards the vaginal opening. Insert 606 is dislodged from support section 604 by this force on removal device 620 allowing arms 608 to contract to the compressed configuration and permitting comfortable removal of device 600. In an embodiment of the invention, device 600 is provided with a cover 622 similar to those described elsewhere herein. In some embodiments of the invention, removal device 620 is attached to both insert 606 and part of device, such as the node, to effectuate removal.

Figure 6C:
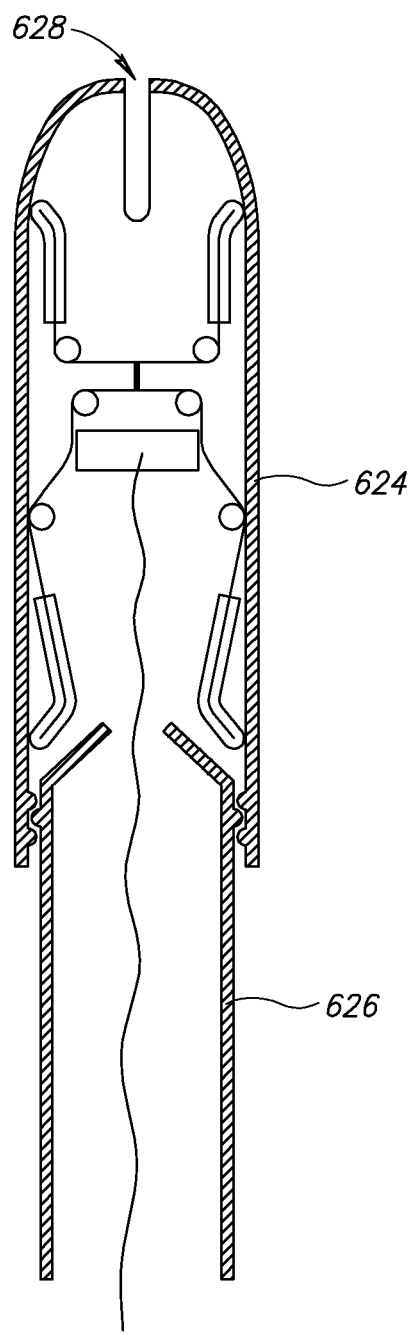

Referring to FIG. 6C, device 600 is shown in a storage configuration in an applicator 624, in accordance with an exemplary embodiment of the invention. Device 600 is stored with insert 606 already positioned within support section 604 in some embodiments of the invention. In such an embodiment, it is believed that storage stresses on device 600 can be reduced due to the flexibility provided by support arm spring elements 614 and/or anchor arm spring elements 618. In some embodiments of the invention, insert 606 is stored dislocated from support section 604, and during deployment insert 606 is forced upwards towards support section 604 with a plunger 626. Continued pressure using plunger 626 towards an opening 628 of the applicator 624 causes device 600 to eventually deploy out of applicator 624, device 600 then assuming the deployed position depicted in FIG. 6B.

Figure 7A:
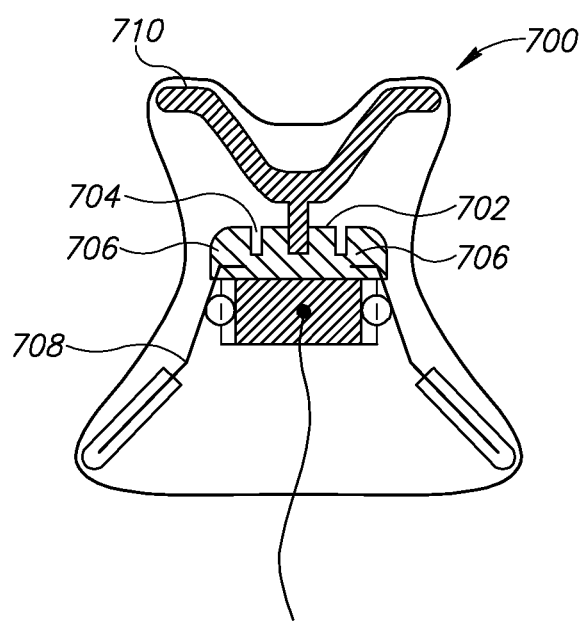
FIGS. 7A-7B are cross-sectional views of an incontinence treating device (A) in a deployed configuration and (B) being removed, in accordance with an embodiment of the invention.
Figure 7B:
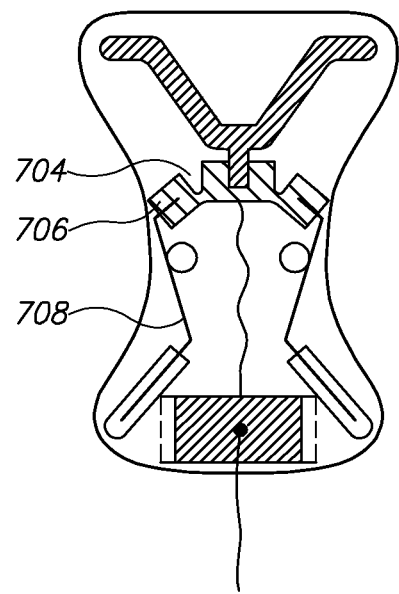

FIG. 7A shows a device 700 which, in place of support arm spring elements 614, has a flexible connection element 702, in accordance with an exemplary embodiment of the invention. Whereas support arm spring elements 614 provides flexibility for device 600, the flexible connection element 702 is provided with notches 704 which enable pivoting ends 706 of device 700 to transition the support arms 708 from a deployed configuration to a removal configuration, shown in more detail in FIG. 7B. Optionally, transitioning is facilitated by a hinge. Optionally, transitioning is achieved by stressing the narrow portion of flexible connection element 702 created by notches 704. In some embodiments of the invention, the anchoring section 710 is not provided with flexible elements, as shown in FIG. 7A. Optionally, anchoring section 710 connects directly to flexible connection element 702, without a node. In some embodiments of the invention, flexible connection element 702 is constructed of metal and/or at least one polymer.

Figure 8A:
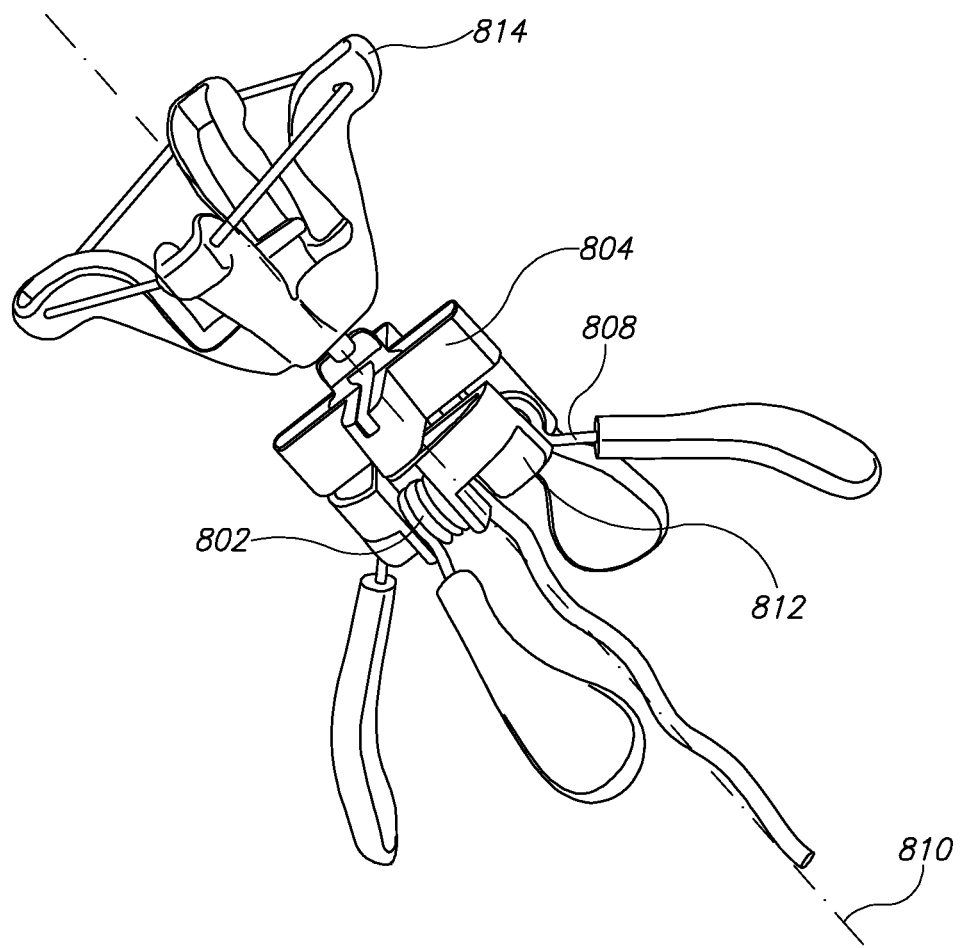
FIGS. 8A-8C: (A) is a perspective view of an incontinence treating device, (B) is an exploded view of the device and (C) is the device in a removal configuration, in accordance with an embodiment of the invention.

Referring to FIG. 8A, a perspective view of an exemplary incontinence treating device 800 is shown in which support arm spring elements 802 are integrated with device 800 in a slightly different manner than that depicted in FIG. 6A. For example, in an embodiment of the invention support arm spring elements 802 are attached to a node 804 using hooked protrusions 806, shown in FIG. 8B, rather than actually forming at least a portion of the node, or not having a node, as with device 600. Support arm spring elements 802 bias support arms 808 towards a central axis 810 of device 800 but are prevented from doing so by an insert 812, in accordance with some embodiments of the invention. The configuration of device 800 depicted in FIG. 8A is that which would be used for rendering incontinence treatment, and optionally would be stored, for example in an applicator, in the same configuration.

Figure 8B:
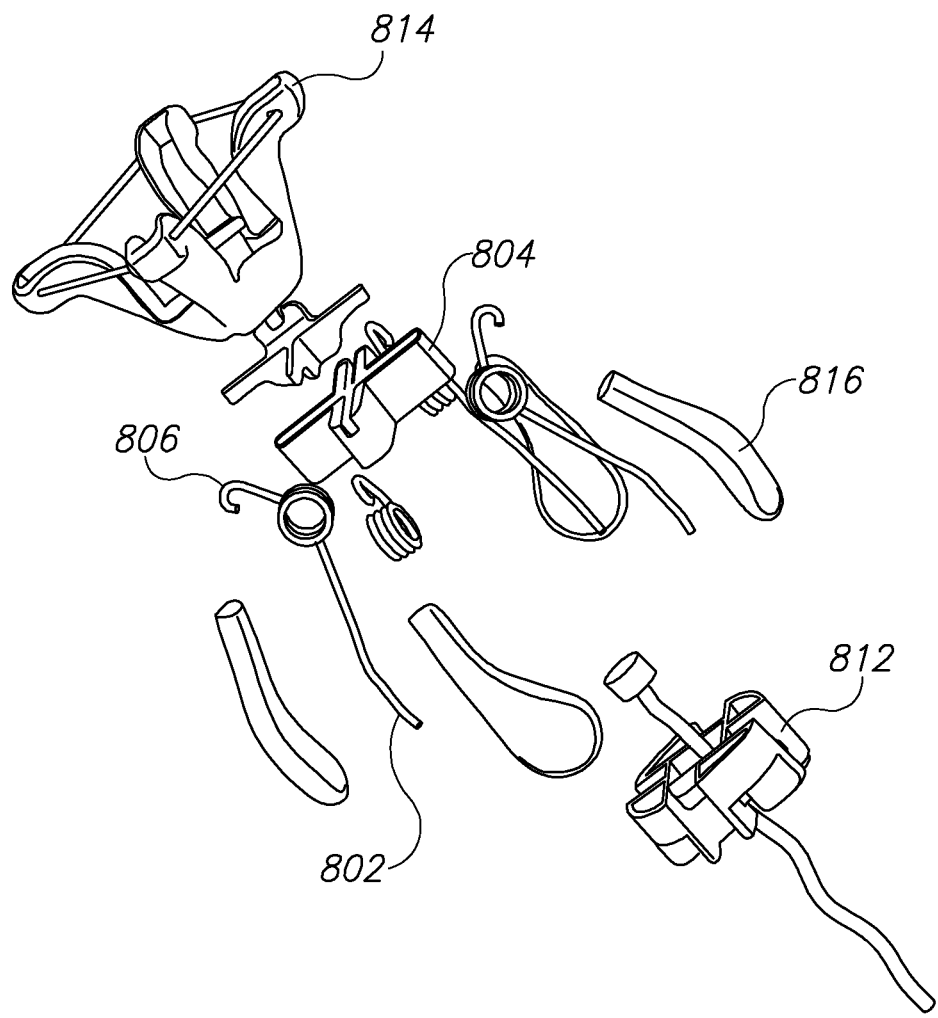

FIG. 8B, is an exploded view of device 800, which more clearly shows an anchoring section 814 which attaches to node 804 to which support arm spring elements 802 are attached. Insert 812 is shown removed from its active position, between the spring elements 802. In some embodiments of the invention, support arm spring elements 802 are provided with an end protector 816 which, among other things, provides enhanced comfort to the wearer and reduces the likelihood of necrosis and/or pressure ulcers In some embodiments of the invention, anchoring section 814, support arm spring elements 802, node 804 and end protectors 816 are constructed of a polymer and/or a metal.

Figure 8C:
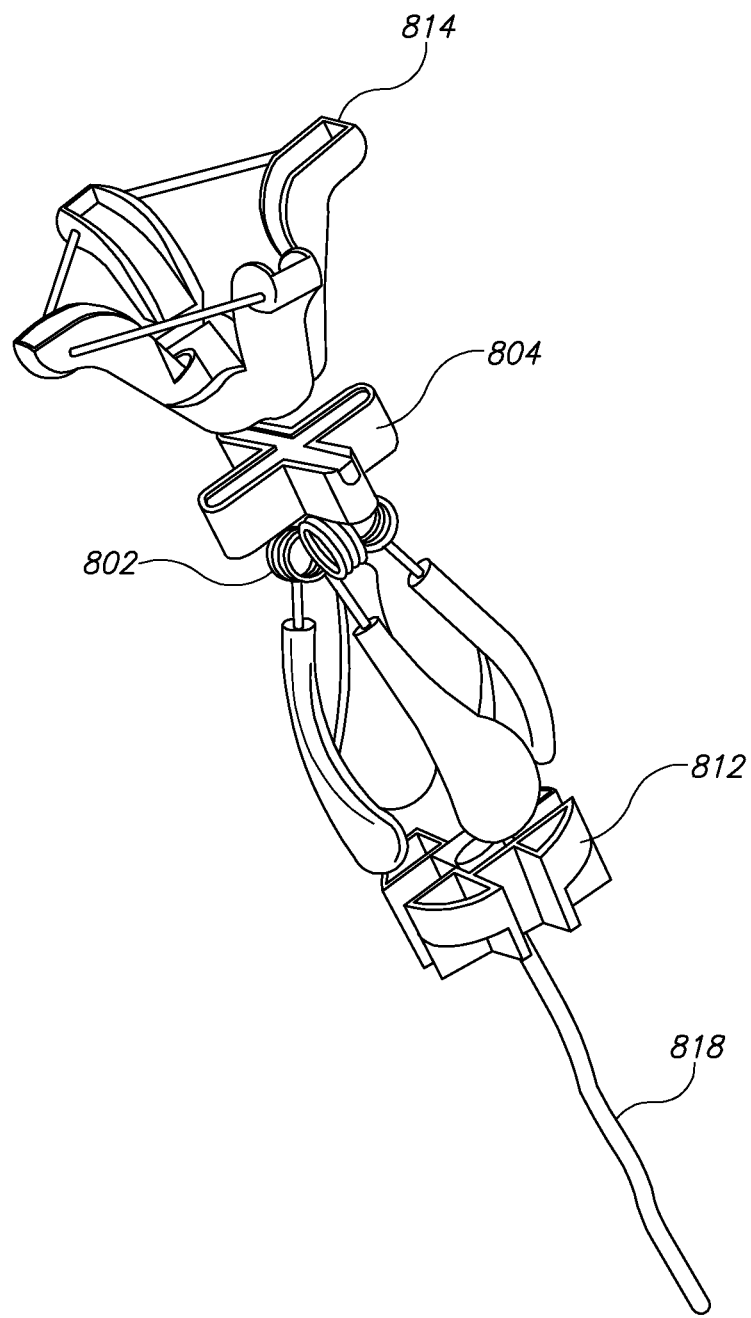

FIG. 8C, shows device 800 in a removal configuration, wherein insert 812 has been removed from its active position within support arm spring elements 802 by the exertion of force on a removal device 818. The removal of insert 812 allows support arm spring elements 802 to exhibit their bias towards central axis 810, reducing the radial diameter of device 800 for easier removal. Optionally, removal device 818 is attached both to insert 812 and to node 804.

Figure 9C:
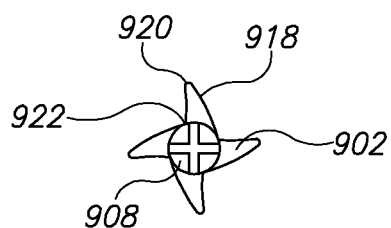

In the exemplary embodiment of the invention depicted in FIG. 9A, an incontinence device 900 is provided with a rotating insert 902 adapted to mate with device 900. Line A-A indicates the point of view of FIG. 9B which shows the top of a plunger 904 which is used, in some embodiments of the invention, to rotate rotating insert 902. In an embodiment of the invention, plunger 904 is provided with an interface 906 which is designed to mate with a counterpart 908 located on rotating insert 902. Rotating insert 902 and counterpart 908 are shown from a bottom view in FIG. 9C. In some embodiments of the invention, rotating insert 902 is optionally provided with a plurality of different diameters, such that in different configurations (e.g. storage and/or deployed), different diameters of insert 902 are used. For example, when in storage the smallest diameter is utilized. Interface 906 and counterpart 908 could be for example similar to a Philips head screw driver, an Allen wrench or a flat head screw driver and a screw adapted to mate with any of those, respectively. In some embodiments of the invention, support arms 910 are manufactured in a biased condition, wherein the bias is towards a central axis of device 900. As with other devices for treating incontinence described herein, device is at least partially flexible.

In some exemplary embodiments of the invention, rotating insert 902 is constructed from any material capable of urging support arms 910 outward. For example, rotating insert 902 is made of plastic materials. Rotating insert 902 is optionally constructed of the same material as device 900, such as silicone, polyurethanes, plastic polymers, ceramic materials and/or metal. Optionally, rotating insert 902 is constructed of a harder and/or stiffer and/or denser material than device 900 to provide enhanced resistance to the counter-pressure of the vaginal wall.

Figure 9E:
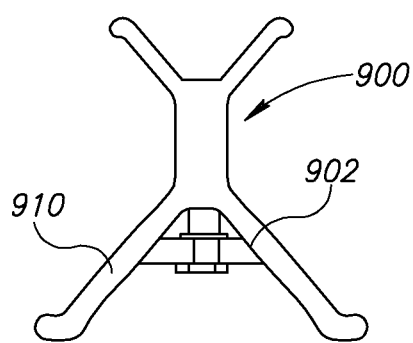
Figure 9D:
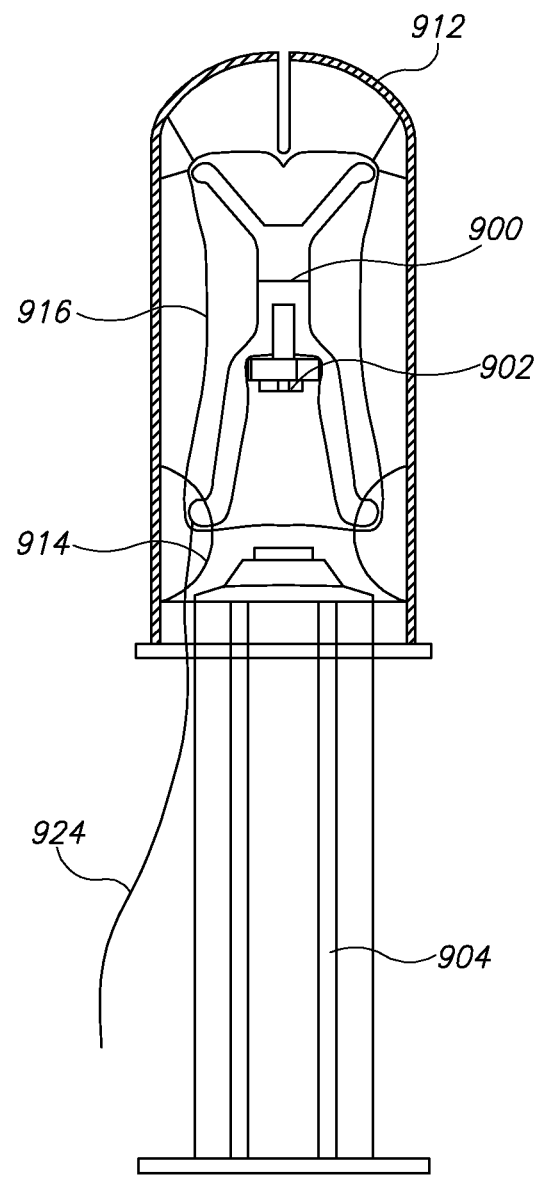

Referring to FIG. 9D, device 900 is shown in a storage and/or pre-deployment configuration within an applicator 912, in accordance with an exemplary embodiment of the invention. In some embodiments of the invention, rotating insert 902 is loosely screwed into device 900 urging support arms 910 with relatively low expansion forces during storage. Optionally, rotating insert 902 is stored mated to interface 906 on plunger 904 and then is added to device 900 just prior to deployment. In an exemplary embodiment of the invention, rotating insert 902 is added to device 900 by pushing plunger 904 towards device 900 and then screwing rotating insert 902 into device 900. Rotating insert 902 is rotated depending on the amount of support arm 910 expansion desired in some embodiments of the invention, for example, as insert 902 is screwed into device 900 and assumes a different relationship to support arms 910 through the screwing, increasing expansion forces can be imparted to support arms 910 by causing urging protrusions 918, shown in FIG. 9C, to outwardly urge support arms 910. In an embodiment of the invention, urging protrusions 918 are sloped to allow for selectable expansion of support arms 910. For example, insert 902 does not have to be turned all the way so that the apex 920 of protrusions 910 is urged against support arms 910; an intermediate level of urging is selectable by rotating insert 902 only partially up the slope. In an embodiment of the invention, maximum urging is accomplished by rotating insert 902 so that apex 920 urges support arms 910 outwardly. In some embodiments of the invention, the storage configuration of device 900 includes having the insert at the least outwardly urging position, wherein storage arms 910 are positioned at a base 922 of protrusions 918. In some embodiments of the invention, applicator 912 is provided with rotation blockers 914 which abut support arms 910 and prevent device 900 from rotating when rotating insert 902 is being screwed into device 900. A cover 916 is optionally provided to device 900 which functions similar to other covers described herein. In an embodiment of the invention, cover 916 is open to permit plunger 904 to push and to screw rotating insert 902 into device 900. Subsequently, cover 916 is closed prior to deployment of device 900 into the user's vagina.

FIG. 9E shows a side view of device 900 in a deployed configuration including support arms 910 (with any other support and anchoring arms removed for improved visibility) being urged outwards by rotating insert 902, in accordance with an embodiment of the invention. Optionally, varying sizes of rotating insert 902 and/or degree of rotation and/or sloping of protrusion 918 are used depending on the spread desired from support arms 910. In some embodiments of the invention, at least one of the principles of operation identified above is used by device 900 to render incontinence treatment. In some embodiments of the invention, a removal device 924, depicted in FIG. 9D, is provided to device 900 for removal of insert 902 and subsequently device 900 from vagina. Optionally, force applied to removal device 924 during removal is sufficient to break threading used to enable rotation/screwing of insert 902 into device 900.

Exemplary Pre-Tensionable Embodiments

It should be noted that although this section is related to "pre-tensionable embodiments" it should be noted that other embodiments described herein are at least optionally pre-tensioned prior to deployment, device 900 as an example. This section is primarily for describing incontinence treating devices that are pre-tensionable by a "cocking" mechanism, in some embodiments of the invention, although some of the concepts described herein are applicable to other incontinence device embodiments. While each of the devices depicted in FIGS. 10A-12B have different features and operate in slightly different manners, in some embodiments of the invention, they share with each other the general operational concept that a pre-tensioning element is at least temporarily, lockably drawn ("cocking") through another piece of the device in order to commence radial expansion of at least the support arms of the device.

Figure 10A:
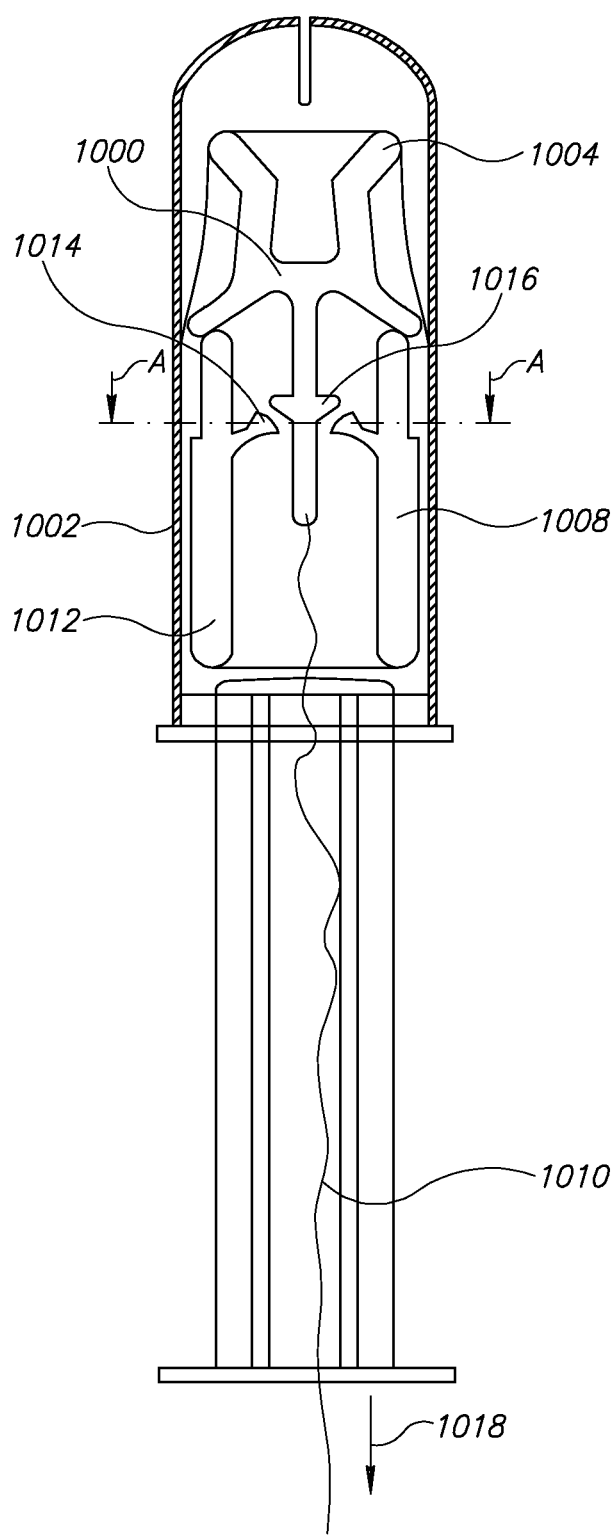
FIGS. 10A-10D are cross-sectional views of an incontinence treatment device (A) in an applicator, (B) in a deployed configuration, (C) of the support section and (D) of the central member and anchoring section, in accordance with an embodiment of the invention.

Referring to FIG. 10A, a cross-section of a sliding pre-tensionable device 1000 for treating incontinence is shown in an applicator 1002, in accordance with an exemplary embodiment of the invention. In some embodiments of the invention, device 1000 is stored in applicator 1002 prior to use. Device 1000 is provided with at least one of an anchoring section 1004, a pre-tensioning spar 1006 and a support section 1008, in some embodiments of the invention. Optionally, a removal device 1010 is provided to sliding pre-tensionable device 1000 for not only pulling out device 1000 after use but for initiating the cocking, as described below. In some embodiments of the invention, anchoring section 1004 is flexible, and is stored in a folded condition, pending deployment. In an embodiment of the invention, support section 1008 is comprised of a plurality of support arms 1012 which while in a storage configuration are substantially vertical. In some embodiments of the invention, device 1000 is provided with a tight cover (not shown), which among other things, keeps support arms 1012 in position for proper deployment (under protrusions 1022, described below). In addition, the cover can be used for any of the other applications described herein.

It should be noted that in some embodiments each support arm 1012 is provided with a notch 1014 which when all the notches 1014 are taken together create an orifice which prevents pre-tensioning spar 1006 from passing downwards through it without sufficient force exerted on removal device 1010. Cross-sectional view A-A, shown in FIG. 10C, shows support section 1008 from a top down view in accordance with an exemplary embodiment of the invention. It can be seen from FIG. 10C that in some embodiments of the invention, support section 1008 is substantially one piece and notches 1014 extend around the circumference of an orifice designed to permit passage of pre-tensioning spar 1006 in at least one direction. In addition, once pre-tensioning spar 1006 has been pulled past the notches 1014, the flared barb 1016 of pre-tensioning spar 1006 at least temporarily prevents notches 1014 from sliding past the flared barb 1016 and down spar 1006.

Sliding pre-tensionable device 1000 is placed into a tensioned deployment configuration by pulling downwards 1018 on removal device 1010 and forcing flared barb 1016 past notches 1014. in some embodiments of the invention, nubs are provided on the inside surface of applicator 1002 which abut support arms 1012 to counter the forces applied on incontinence device 1000 and to prevent it from moving downwards in applicator 1002. The tips 1020, shown in detail in FIG. 10B, of support arms 1012 are positioned such that when support arms 1012 transition from a storage configuration to a deployed configuration tips 1020 travel along the underside of a central member 1022 sized and adapted to position support arms 1012 in a position to render treatment for incontinence. Optionally, grooves 1024 are provided to the underside of central member 1022 in which tips 1020 can travel during the transition, as shown in FIG. 10D. In an embodiment of the invention, various considerations such as: the distance of flared barb 1016 from central member 1022; the size and/or shape of flared barb 1016; the size and/or shape of notches 1014; and the flexibility of device 1000 as a whole, and/or notches 1014 in particular are weighed in order to provide a device 1000 which when deployed, renders effective incontinence treatment. For example, the distance of flared barb 1016 from central member 1022 could be reduced (and the notches 1014 to match) in order to provide a wider angle of deployment of support arms 1012. As another example, the size of flared barb 1016 could be reduced to enable pre-tensioning with less force and/or to provide a less secure tensioned state. In some embodiments of the invention, device 1000 is cocked while it is still in applicator 1002 and prior to deployment. In such an embodiment, support arms 1012 do not realize their full expanded radius until device 1000 is expelled from applicator 1002.

Figure 10B:
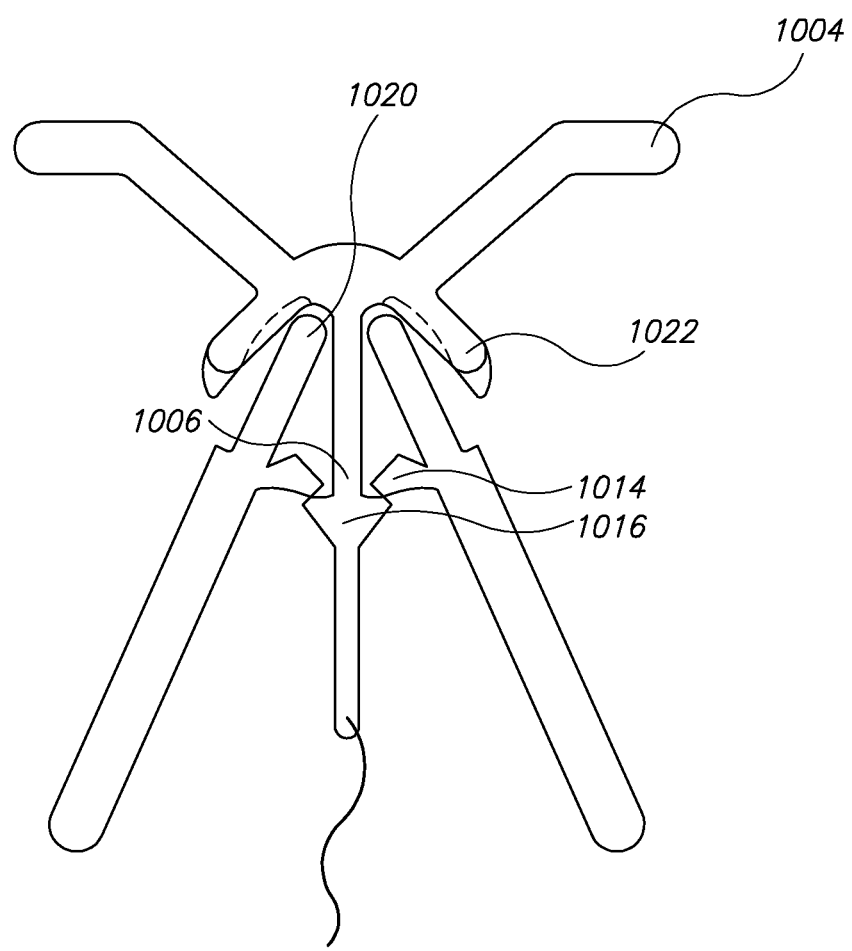
Figure 10C:
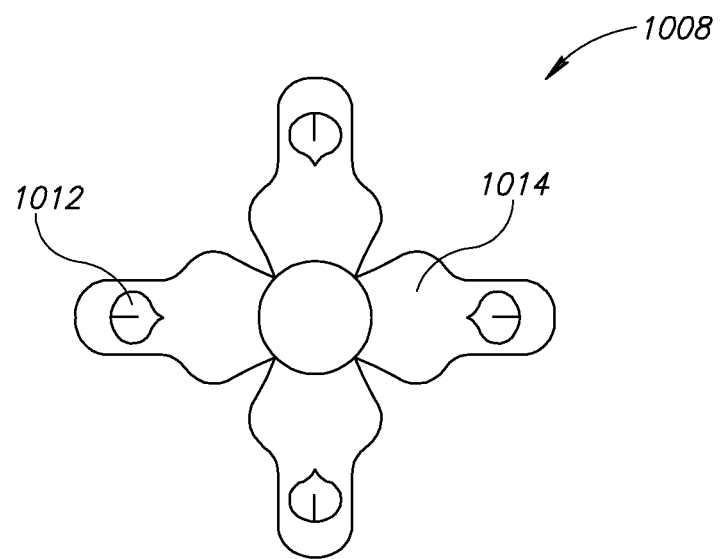
Figure 10D:
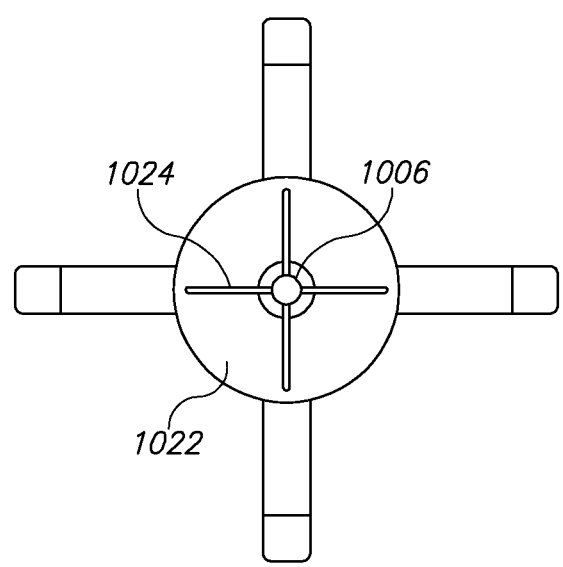

FIG. 10B shows device 1000 is a deployed configuration already expelled from applicator 1002, in accordance with some embodiments of the invention. It can be seen that support arms 1012 have transitioned from a vertical storage configuration to an angled deployed configuration. In some embodiments, this is caused by tips 1020 sliding towards spar 1006 along central member 1022 as a result of the interaction between flared barb 1016 and notches 1014. In a deployed configuration, device 1000 provides incontinence treatment using at least one of the principles of operation described above. Anchoring section 1004 is also shown in a deployed configuration, although the specific configuration of the embodiment shown is by way of example only. In some embodiments of the invention, removal device 1010 is provided for removal of incontinence treating device 1000 from vagina. Optionally, a cover is provided to device 1000.

FIG. 11A shows an adjustable, pre-tensionable device 1100 for treating incontinence in an applicator 1102, in accordance with an exemplary embodiment of the invention. Device 1100 is provided with an anchoring section 1104, a support section 1106 and a pre-tensioning spar 1108, in some embodiments of the invention. In an embodiment of the invention, at least support section 1106 is provided with a plurality of support arms 1112. Pre-tensioning spar 1108 differs from pre-tensioning spar 1006 in that pre-tensioning spar 1108 has a plurality of flared barbs 1110 instead of just one. In an embodiment of the invention, each of flared barbs 1110 is slightly larger in diameter than the one preceding it, in the deployment direction. Pre-tensioning spar 1108 is adapted to fit through an orifice in support section 1106, in an embodiment of the invention. In addition, pre-tensioning spar 1108 is provided with connectors 1114 which connect spar 1108 to support arms 1112 such then when spar 1108 is advanced through the orifice, connectors 1114 urge support arms 1112 outwards. In some embodiments of the invention, device 1100 is provided with a cover.

In a storage configuration, such as depicted in FIG. 11A, device 1100 is optionally not pre-tensioned, wherein none of flared barbs 1110 of pre-tensioning spar 1108 are drawn through the support section orifice. However, just prior to deployment, device 1100 is transitioned into a deployment configuration similarly to device 1000, by "cocking" it with a removal/activating device 1116, with the additional possibility of selecting the tensioning of support arms 1112 depending on which of flared barbs 1110 is ultimately advanced through the orifice. As can be seen in FIG. 11B, support arms 1112 can be spread wider as each flared barb 1110 passes through orifice, in accordance with an exemplary embodiment of the invention. Removal of device 1100 from the vagina is optionally achieved by applying force on removal device 1116 in a direction towards the vaginal introitus. In an embodiment of the invention, the user pulls pre-tensioning spar 1108 to a position where no flared barbs 1110 are urging support arms 1112 outward (thereby allowing support arms 1112 to converge towards a central axis of device 1100), for example past the last flared barb 1110 on spar 1108, in the deployment direction.

Figures 12A, 12B, 12C:
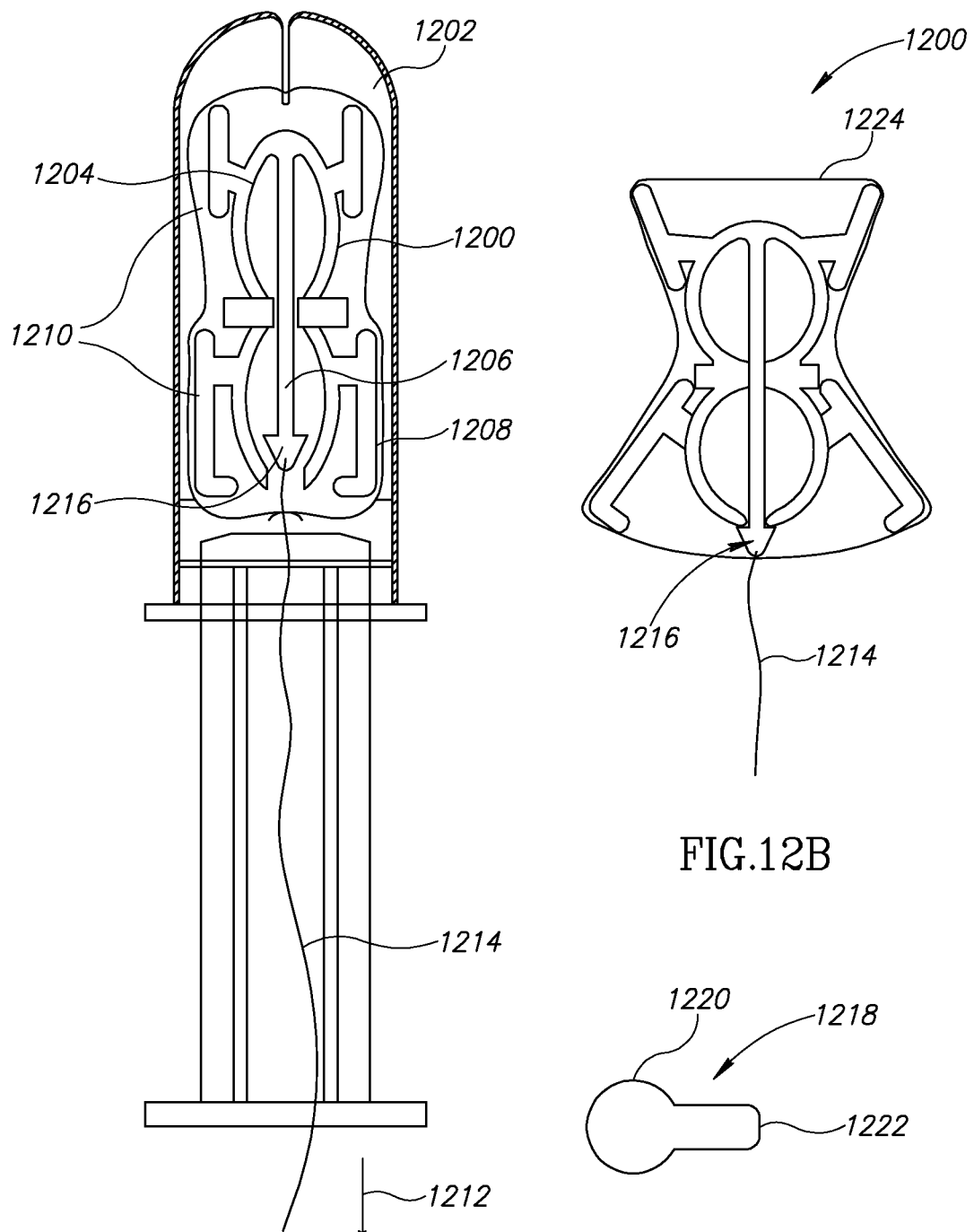
FIGS. 12A-12C are cross-sectional views of an incontinence treatment device (A) in an applicator, (B) in a deployed configuration and of (C) a slotted opening of device, in accordance with an embodiment of the invention.

Referring to FIG. 12A, a pre-tensionable device 1200 which utilizes at least its structural flexibility to provide pre-tensioning is shown in an applicator 1202, in accordance with an exemplary embodiment of the invention. Device 1200 is provided with an anchoring section 1204, a pre-tensioning spar 1206, and a support section 1208, in some embodiments of the invention. Generally, anchoring section 1204 and/or support section 1208 are comprised of circular or ovoid shaped flexible sections. Device 1200 is optionally constructed from a polymer and/or a metal material. In an embodiment of the invention, these sections are provided with extensions 1210 which function to provide anchoring and/or support. At least one of the principles of operation described above is used by device 1200 to render treatment for incontinence, in some embodiments of the invention.

In some embodiments of the invention, device 1200 is pre-tensioned in applicator 1202 prior to deployment by pulling down 1212 on a removal device 1214 which also doubles as the pre-tensioning actuator, in accordance with an embodiment of the invention. Downward force on removal device 1214 causes flexible sections 1204, 1208 to compress in a direction towards removal device 1214, eventually permitting a flared barb 1216 of pre-tensioning spar 1206 to pass through slotted opening 1218, shown in more detail in FIG. 12C. Slotted opening 1218 is comprised of an orifice 1220 adapted to accommodate flared barb 1216 to enable its passage and a slot 1222 which is adapted to accommodate removal device 1214, in an embodiment of the invention. In operation, as removal device 1214 pulls flared barb 1216 past orifice 1220, removal device 1214 can be moved to the side and into slot 1222 which at least temporarily secures flared barb 1216, and thus device 1200, in a tensioned configuration, for example as shown in FIG. 12B. For use, device 1200 is then expelled from applicator 1202 into a deployed position in the vagina. For removal of device 1200 after use, removal device 1214 is moved in a direction opposite of slot 1222, enabling flared barb 1214 to pass back through orifice 1220 thereby releasing the tensioning on device 1200, in an embodiment of the invention. In some embodiments, device 1200 is provided with a cover 1224.

An Exemplary Customizable Bi-Polar Incontinence Treatment Device

Figure 13A:
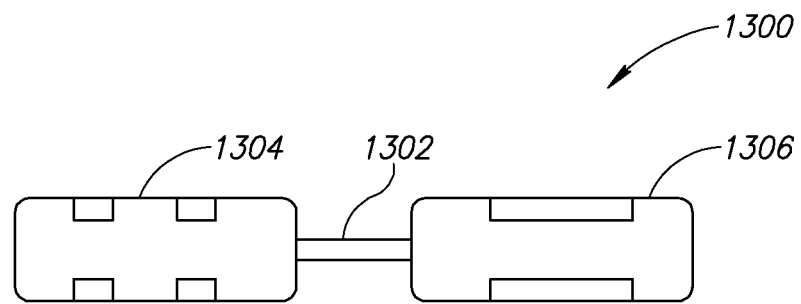
FIGS. 13A-13C: (A) is a schematic of an incontinence treatment device, (B) is a perspective view of a band, and (C) is a schematic view of an assembled device, in accordance with an embodiment of the invention.

FIG. 13A shows a customizable bi-polar incontinence treatment device 1300, in accordance with an exemplary embodiment of the invention. Device 1300 is provided with a node 1302 which connects two poles 1304, 1306, in some embodiments of the invention Optionally, node 1302 and/or poles 1304, 1306 are flexible. In some embodiments of the invention, at least one pole is used for anchoring device 1300. In some embodiments of the invention, at least one pole is used for providing support for the treatment of incontinence. Poles are optionally variably sized and/or shaped to provide different dimensional options for device 1300 to users. Optionally, poles 1304, 1306 are the same or different size and/or shape. In some embodiments of the invention, at least one of poles 1304, 1306 is provided with at least one groove adapted to mate with a band, bands being described in more detail in FIG. 13B. In some embodiments of the invention, bands are provided which render both anchoring and support functions, enabling the insertion of device 1300 from either end without a loss of performance.

Figure 13B:
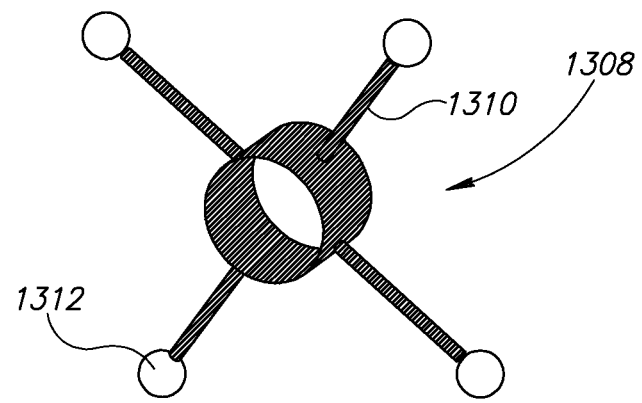

Referring to FIG. 13B, an exemplary band 1308 is shown which is adapted to mate to at least one of poles 1304, 1306, optionally mating to at least one groove located thereon. In some embodiments of the invention, more than one band is mated to a pole 1304, 1306. In some embodiments of the invention, band 1308 is rotatable on at least one of poles 1304, 1306. In an exemplary embodiment of the invention, band 1308 is provided with a plurality of protrusions 1310 which radiate outwards from band 1308, optionally at various angles to band 1308. Protrusions 1310 optionally function similarly to support and/or anchor arms which are described elsewhere herein. For example, protrusions 1310 provided to a band used for providing support could treat incontinence using at least one of the principles of operation described above. Optionally, at least some of protrusions 1310 are flexible. In some embodiments of the invention, protrusions 1310 can be arranged in any fashion on band 1308 as long as they perform their intended anchoring and/or support function, for example, protrusions 1310 can be arranged an equal distance from one another around the circumference of band 1308. In some embodiments of the invention, protrusions 1310 are not arranged equally around the circumference of band 1308. Optionally, protrusions 1310 are aligned in more than one row around the circumference of band 1308. Optionally, protrusions 1310 are not all the same size, length, diameter, shape and/or height. In some embodiments of the invention, protrusions 1310 are provided with an end protector 1312 which increases comfort to the user and/or reduces the chance of necrosis and/or pressure ulcers.

Figure 13C:
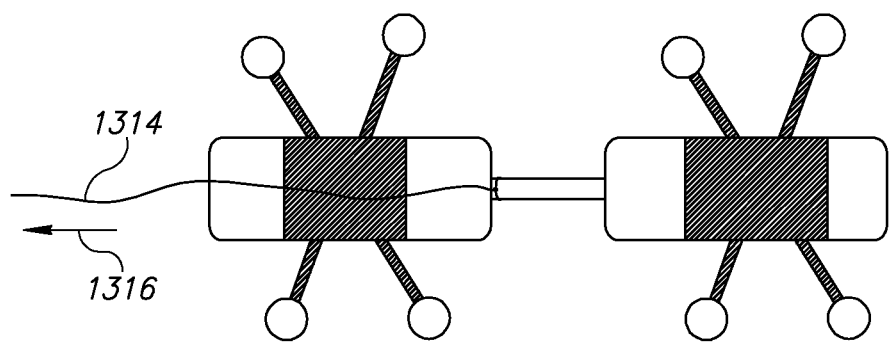

FIG. 13C shows an assembled device 1300, in accordance with an exemplary embodiment of the invention. It can be seen that in this embodiment two bands 1308 have been mated to device 1300, one to each pole 1304, 1306. While in FIG. 13C the configuration of the bands is the same, they can vary in some embodiments of the invention as described above. Optionally, device 1300 is provided with a cover. Poles 1304, 1306 may be made of any plastic or elastic material, such as polyurethane, silicone, polypropylene, foam polyurethane, or the like. Protrusions 1310 and optionally end protectors may be made of elastomers, polymers and/or plastics. In some embodiments of the invention, a removal device 1314 is provided for removal of incontinence treating device 1300 from the user's vagina after use. Force 1316 applied towards the vaginal introitus using removal device 1314 causes device 1300 to displace, in accordance with an embodiment of the invention. Band 1308 is optionally situated directly on poles 1304, 1306 or may be "cushioned" underneath with a compressible material, such as a foam polyurethane. In some embodiments of the invention, cushioning band 1308 on poles 1304, 1306 supplies better flexibility to the protrusions 1310.

In an exemplary embodiment of the invention, flexibility provided by cushioning band 1308 and/or protrusions 1310 contributes to ease of insertion and/or removal of the device. Optionally, distal ends of protrusions 1310 move backwards during insertion and/or forward during removal. Motion of this type can be achieved by providing protrusions 1310 with a suitable degree of flexibility. Alternatively, or additionally, poles 1304 and/or 1306 are provided with a suitable degree of flexibility to contribute to motion of this type. A suitable degree of flexibility can be provided by, for example, by embedding rigid metal pins in a spongy material. Optionally, the rigid metal pins change directions during movement due to cushioning provided by the spongy material.

An Exemplary Orientationally Neutral Incontinence Treating Device

Figure 14A:
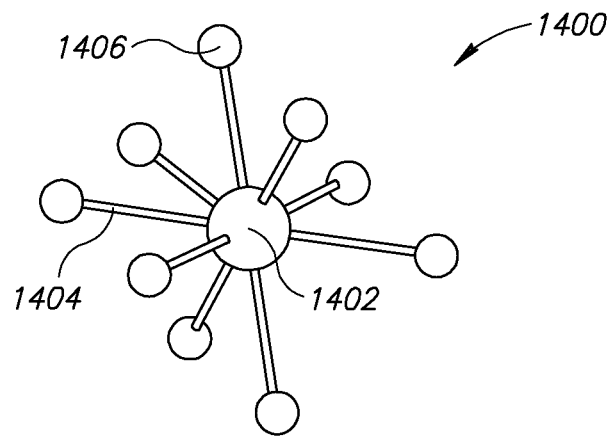
FIGS. 14A-14C: (A) is a perspective view of an incontinence treating device, (B) is the device in an applicator, and (C) is an alternative device wherein the core is comprised of connectors, in accordance with an embodiment of the invention.

In an exemplary embodiment of the invention, an incontinence treating device 1400 is provided which can be inserted into the vagina in any orientation with respect to the vagina and still be effective. FIG. 14A shows a perspective view of device 1400 which is generally formed from a core 1402 located centrally and a plurality of protrusions 1404 radiating outwardly from core 1402, in accordance with an embodiment of the invention. Optionally, at least protrusions 1404 are flexible. Optionally, at least core 1402 is flexible. In an embodiment of the invention, core 1402 is comprised of a shape memory material whereby in a storage configuration core 1402 is compressed but upon deployment in situ expands to its functional size. Optionally, rigidity of core 1402 is controlled by using air or liquid or a combination of an air and liquid filling to control its internal pressure. In some embodiments of the invention, protrusions 1404 are equally spaced from one another around core 1402. Optionally, they are not equally spaced from one another around core 1402. In some embodiments of the invention, protrusions 1404 are identical in size, shape, diameter, length and/or flexibility. Optionally, at least one protrusion exhibits a different size, shape, diameter, length and/or flexibility from the other protrusions 1404. In some embodiments of the invention, protrusions are provided with an end protector 1406 which increases comfort to the user and/or reduces the chance of necrosis and/or pressure ulcers. Protrusions 1404 provide anchoring and/or support functions in order to render treatment for incontinence to a user, in an embodiment of the invention. In some embodiments, incontinence treatment is provided by using one of the principles of operation described above. Protrusions 1404 and optionally end protectors may be made of elastomers such as silicone, foam materials such as polyurethane and/or polystyrene, and/or air or liquid filled sacks, and the like. In an alternative embodiment of the invention, in which the incontinence treating device is bi-polar such as the one depicted in FIG. 13C, two devices 1400 are connected together with a central node.

In an exemplary embodiment of the invention, flexibility provided by core 1402 and/or end protectors 1406 contributes to ease of insertion and/or removal of device 1400. Optionally, protrusions 1404 move in one direction during insertion and/or in a second direction during removal. Motion of this type can be achieved by providing protrusions 1404 with a suitable degree of flexibility. A suitable degree of flexibility can be provided by, for example, by embedding rigid protrusions 1404 in a spongy material at core 1402 and/or end protectors 1406. Optionally, the rigid protrusions 1404 change directions during movement due to cushioning provided by the spongy material.

Figure 14B:
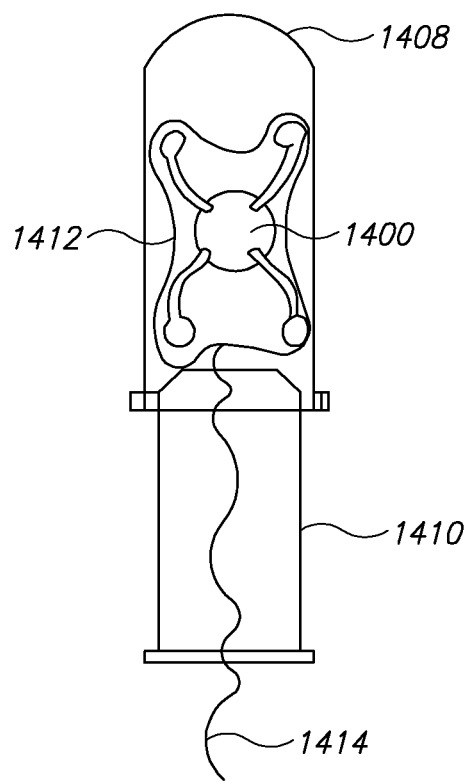

FIG. 14B shows device 1400 in a storage configuration in an applicator 1408, according to an embodiment of the invention. In embodiments where protrusions 1404 cannot extend fully because the lumen of applicator 1408 is limiting, protrusions 1404 flex to allow storage of device 1400 within applicator 1400. In an embodiment of the invention, protrusions 1404 remained flexed for storage until deployment of device out of applicator 1408 by urging device 1400 out with a plunger 1410. Optionally, device 1400 is provided with a cover 1412. In some embodiments of the invention, a removal device 1414 is provided to incontinence device 1400 for removing device 1400 from the vagina at the conclusion use.

In some embodiments of the invention, device 1400 is provided with longer and/or thicker protrusions to adapt device 1400 for rendering prolapse treatment. In some embodiments of the invention, device 1400 is provided with at least one of an absorbent core, absorbent protrusions or absorbent end protectors to provide menstrual tampon functionality.

Figure 14C:
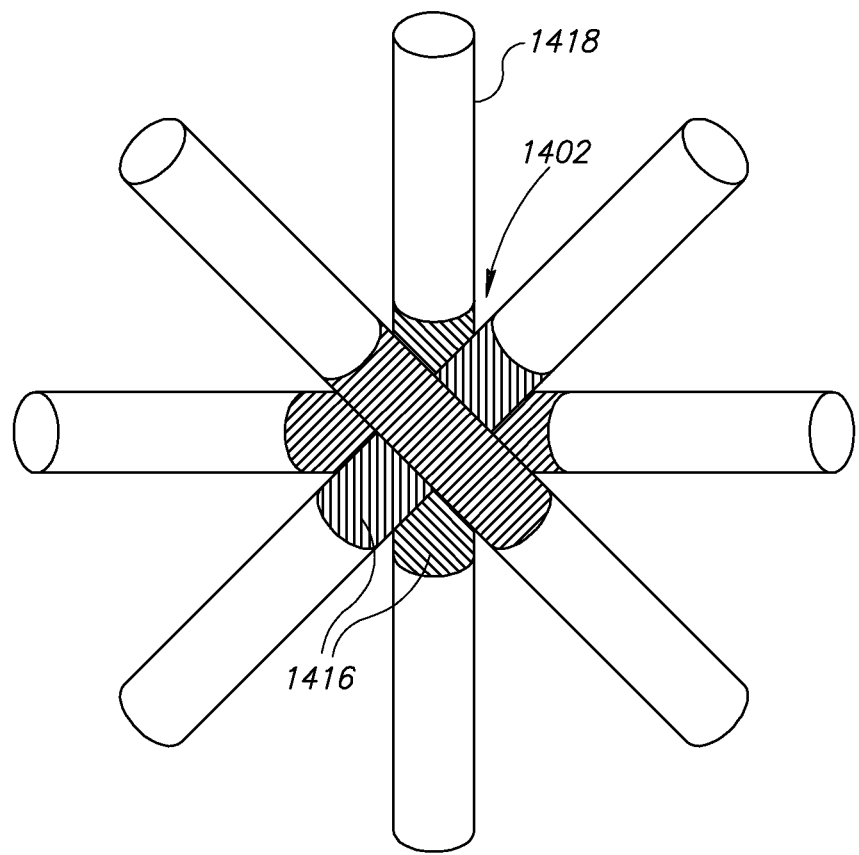

In an exemplary embodiment of the invention, core 1402 is comprised of a plurality of connectors 1416 which are used for attaching arms 1418 to core 1402. Shown in FIG. 14C is a core which uses a plurality of connectors 1416 in this fashion. In an embodiment of the invention, each connector is provided with an interface at each end wherein arms 1418 can be attached. Optionally, the angles at which arms 1418 extend from core 1402 are controlled by angling the plurality of connectors 1416 according to the angles desired. In an embodiment of the invention, arms 1418 are comprised of a flexible material, such as silicon or polyurethane, or from foamy materials such as foam polyurethane. Optionally, arms 1418 are moisture absorbent. In some embodiments of the invention, arms 1418 screw into core 1402 prior to insertion into applicator 1408. Optionally, arms 1418 fit within the interface using a compression fit, the diameter of the arms 1418 slightly reducing when inserted into the interface as a result of compression exerted on arms 1418 by core 1402.

In some embodiments of the invention, arms 1418 are comprised of at least one spring element, which acts to provide support and/or anchoring functions, but which also provides a dynamically adjusting, cushioned fit to the vaginal wall of the user. An alternative to the embodiment depicted in FIG. 14C is to eliminate core 1402 and have each of arms 1418 extend from one side of the device to the other, with the same arm contacting a first portion of the vaginal wall and a second portion of the vaginal wall opposite the first portion.

In an embodiment of the invention, removal of any of the devices depicted in FIGS. 14A-C is facilitated by pre-weakened segments of at least some arms 1418 which when force is applied to a removal device causes the pre-weakened segments of arms 1418 to break. In some embodiments of the invention, the pre-weakened segments react to forces directed towards the vaginal introitus, but not to forces applied during nominal usage within the vagina. Optionally, the pre-weakened segments are located near a base of the arms 1418 proximal to core 1402. In some embodiments of the invention, when the pre-weakened segments cause arms 1418 to break, arms 1418 still remain attached to the main body of the incontinence treating device, for example, if the pre-weakened part of the segment does not extend all the way through the diameter of arms 1418.

In some exemplary embodiments of the invention these pre-weakened segments do not break but bend in one direction when inserted into the vagina and in an opposite direction when removed from the vagina. Optionally, bending during removal imparts a smaller diameter to the device during removal. In an exemplary embodiment of the invention, two pre-weakened segments, one at each side of connector 1416. In another embodiment, core 1402 is more flexible than arms 1418. Optionally, flexibility of core 1402 and/or the pre-weakened segments contribute to comfort during removal.

Exemplary Balancing Device for Treating Incontinence

Figure 15A:
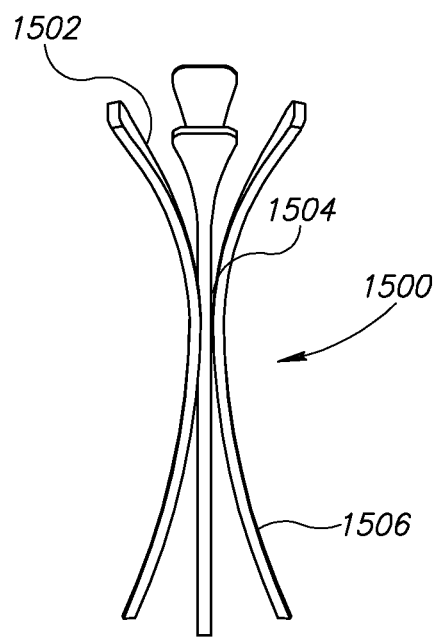
FIGS. 15A-15B: (A) is a perspective view of an incontinence treating device, (B) is a cross-section of the device, in accordance with an embodiment of the invention.

Referring to FIG. 15A, a perspective view of a balancing device 1500 for treating incontinence is sown, in accordance with an exemplary embodiment of the invention. In some embodiments, device 1500 has four lever units 1502 which provide anchoring and/or support functions. Each lever unit 1502 is provided with a pivot point 1504, shown in FIG. 15B, whereby on one side of pivot point 1504, lever unit 1502 can be termed support section 1506 and on the other side of pivot point 1504, lever unit 1502 can be called anchoring section 1508. However, it should be noted that "support section" and "anchoring section" are for ease of reference only, and that each side of lever unit 1502 from pivot point 1404 can perform anchoring and/or support functions in conjunction.

Figure 15B:
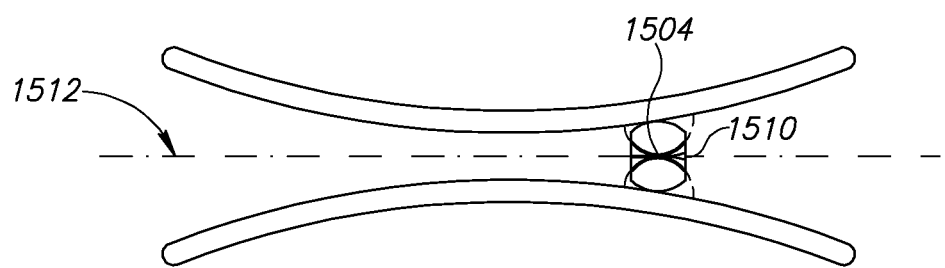

In an embodiment of the invention, each pivot point 1504 of the lever units are individually, rockably connected at a node 1510, shown in more detail in FIG. 15B. In this manner, each lever unit 1502 operates independently and is free to move separately from the other lever units. Similar to a seesaw, lever unit 1502 rocks on pivot point 1504 depending on forces applied to lever unit 1502 while in situ. For example, when a stressful event occurs proximal to anchoring section 1508 pushing anchoring section 1508 downwards towards a central axis 1512 of the device, support section 1506 rises away from central axis 1512. In this embodiment of the invention, support section 1506 provides additional, affirmative support during a stressful event. In some embodiments of the invention, at least one of the principles of operation, in addition to the one described herein, are used to provide treatment for incontinence. During non-stressful event times within the vagina, the rockable balancing feature of lever units 1502 provides a comfortable fit within the vagina.

In an embodiment of the invention, lever units 1502 are mounted asymmetrically such that node 1510 is not centered along the length of lever units 1502 (also shown in FIG. 15B). Optionally, node 1510 is positioned anywhere along the length of lever units, including at a different place for at least one of lever units 1502 in relation to the others. In some embodiments of the invention, lever units 1502 are not symmetrically oriented around node 1510 and/or central axis 1512. Optionally, more or less than four lever units 1502 are provided to device 1500. In some embodiments of the invention, lever units 1502 are slightly curved. Optionally, lever units 1502 are substantially straight. In an embodiment of the invention, lever units 1502 are at least slightly flexible, allowing for anchoring and support functions but also allowing for slight flexing of device 1500 as the user's vaginal wall moves during daily activity. Optionally, lever units 1502 are substantially rigid, being providing with movement and/or adaptability to the user by node 1510. Lever units 1502 may be produced from any kind of a plastic and/or elastic material. Optionally, device 1500 is provided with a cover. In an embodiment of the invention, device 1500 is stored in an applicator (not shown) and is deployed from the applicator by the user in order to deploy device 1500.

An Exemplary Device without a Discrete Anchoring Section

Referring to FIG. 16A, an incontinence treating device 1600 is shown which does not need a discrete anchoring section in order to provide treatment, in an embodiment of the invention. Device 1600 is provided with a central structure 1602 which in some embodiments of the invention functions as both a support section and an anchoring section. In some embodiments of the invention, central structure 1602 is provided with a plurality of protrusions 1604 which enable device 1600 to provide support in accordance with at least one of the principles of operation described above. A flexible membrane 1606 is also provided to central structure 1602, in some embodiments of the invention. Optionally, a removal device 1608 is attached to flexible membrane 1606. In some embodiments of the invention, no separate anchoring section is provided but central structure 1602 is has a slightly extended structure towards cervix to assist with anchoring.

FIG. 16B shows exemplary device 1600 from the perspective of Line A-A shown in FIG. 16A. From this view, it can be seen that central structure 1602 is circular in an embodiment of the invention. However, in other embodiments of the invention, central structure 1602 can have a different shape, for example oblong, ovoid, or with sides (quadrilateral, octagonal, etc.). Protrusions 1604 are shown, numbering four and arranged equally spaced around the circumference of central structure 1602. It should be noted that more or less protrusions 1604 are provided to central structure 1602 depending on the needs of the user or the intended function of device 1600. In some embodiments, protrusions 1604 are optionally varied in size, shape, diameter, length, material and/or flexibility. Exemplary flexible membrane 1606 is also shown in FIG. 16B. In some embodiments of the invention, flexible membrane 1606 does not completely seal the open area framed by central structure 1602. For example, flexible membrane 1606 is frusto-conical in shape. Optionally, flexible membrane 1606 permits the transmission of moisture therethrough and/or is porous.

Figure 16D:
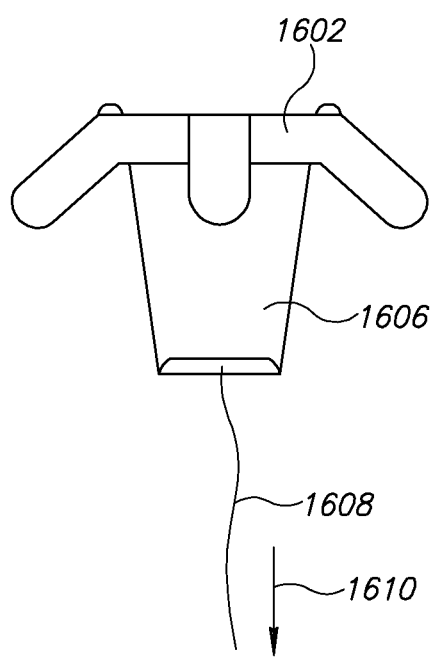

FIGS. 16C-D show progressive device 1600 configurations during removal, in accordance with an exemplary embodiment of the invention. A partially collapsed flexible membrane 1606 is shown in FIG. 16C, as downward force 1610 on removal device 1608 causes flexible membrane 1606 to pass through the open area framed by central structure 1602. FIG. 16D shows flexible membrane 1606 in a removal configuration whereby continued downward force 1610 on removal device 1608 causes device 1600 to dislodge and to exit from the vagina.

Figure 16E:
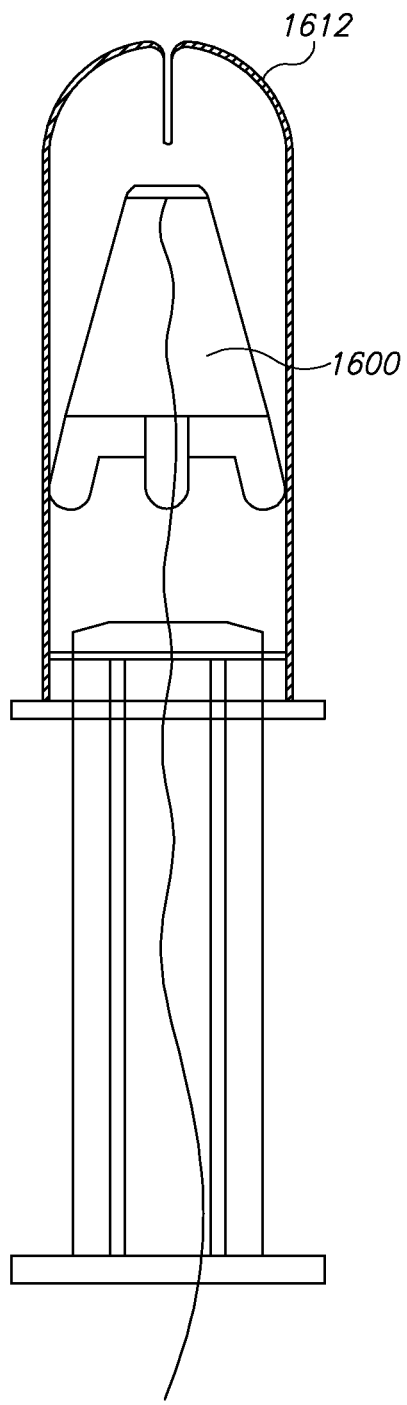

Referring to FIG. 16E, device 1600 is shown in an applicator 1612 prior to deployment into a user's vagina. In some embodiments of the invention, central structure 1602 is at least slightly flexed while in applicator 1612. A plunger 1614 is optionally used to expel device 1600 from applicator 1612 during deployment.

In some exemplary embodiments of the invention, membrane 1606 is not flexible, but is instead substantially rigid, and/or is at least more rigid than the flexible membrane described above. Optionally, the rigid membrane is constructed of the same material as device 1600. In an embodiment of the invention, the rigid membrane is in the same general configuration as membrane 1606 shown in FIG. 16A, protruding into the user's vagina towards the cervix. The rigid membrane acts to prevent rotation of device 1600 towards cervix and/or introitus when device 1600 is deployed, in an embodiment of the invention.

Additional Exemplary Materials and Manufacturing Considerations

In some embodiments of the invention, materials are used for the construction of the devices described herein, which haven't been yet discussed. In some embodiments of the invention, these materials alter a material characteristic upon deployment into a user's vagina. For example, compressed materials, such as viscose or paper pulp, are optionally used for building incontinence devices. Optionally, these compressed materials are laminates. In some embodiments of the invention, the compressed material is liquid absorbent, for example, the device uses the woman's natural vaginal secretions to become more rigid and/or to assume an incontinence rendering shape. Optionally, the material is non-absorbent, for example, in the case of materials which are not activated by moisture, but by heat. In an embodiment of the invention, a compressed material device is pre-worked in such a way that upon introduction to the vagina, the device assumes a desired shape for rendering incontinence treatment. For example, the compressed material may be sutured or welded in order to form a device. In some embodiments of the invention, materials such as a cardboard, linen, paper pulp, seaweed, starches, organic polymers, (bio)degradable polymers, and/or the like are used for constructed an incontinence device. In some embodiments of the invention, a compressed material is reinforced with an integrated material, such as metal wire.

Another example of a material from which incontinence treating devices are optionally comprised, are solid absorbents. Similar to the compressed materials embodiments described above, devices may be manufactured from solid absorbents which exhibit first material properties outside the vagina and second material properties after deployment inside the vagina. In an embodiment of the invention, solid absorbents are used to provide a device that will supply intravaginal support after absorbing liquids. Liquids needed for this may be from vaginal secretions, or by using a small sack of liquid that is punctured inside the applicator during the process of deployment. In some embodiments of the invention, the solid absorbent is a Super Absorbent Polymer, for example polyacrylamide. Some advantages for using solid absorbents are longer shelf life and their ability to have a smooth surface, easing removal of the device.

In some embodiments of the invention, incontinence treating devices are manufactured in different sizes in order to accommodate individual needs of users.

Exemplary Applicator

While any of the applicators described in PCT/IL2005/000304, U.S. Application Ser. No. 60/719,422, U.S. Application Ser. No. 60/762,059 and PCT/IL2006/000346 are optionally used with the incontinence treating devices described herein, an applicator designed to transition its enclosure from a storage configuration to a deployment configuration could also optionally be used. Referring to FIG. 17A, such an applicator 1700 is shown in a cross-sectional view. In an embodiment of the invention, applicator 1700 assumes a storage configuration in order to preserve the shelf life of an incontinence treating device 1704 stored therein, for example, by not compressing, or only partially compressing, portions of device 1704 prior to deployment. Applicator 1700 is provided with an enclosure 1702 which is adjustable in diameter to accommodate device 1704 positioned therein. Optionally, enclosure 1702 is adjustable in more than one location, for example in a location proximal to a support section 1706 of device 1704 and in a location proximal to an anchoring section 1708 of device 1704. In an embodiment of the invention, adjustable areas of enclosure 1702 are implemented in a bellows or accordion-like configuration, wherein the adjustable area is roughly triangular in shape with its apex at the most remote location of the adjustable area from enclosure 1702. In some embodiments of the invention, applicator 1700 is provided with a removable grip 1710 located near an exit 1712 of enclosure 1702 and/or a grip 1714 located on enclosure 1702 opposite exit 1712. Optionally, one or less grips are provided to applicator 1700. In an embodiment of the invention, applicator 1700 is constructed from a plastic material. In some embodiments of the invention, an incontinence treating device is not inserted into an applicator until just prior to the intended deployment, thereby sparing the device the storage stresses normally associated with storage in an applicator.

FIG. 17B shows applicator 1700 in a deployment configuration, in accordance with an exemplary embodiment of the invention. Transition from the exemplary storage configuration depicted in FIG. 17A to the exemplary deployment configuration depicted in FIG. 17B is accomplished by pulling in opposite directions on grips 1710, 1714, in an embodiment of the invention. Optionally, one grip is held steady while the other grip is pulled in order to activate the transition. In an embodiment of the invention, the adjustable areas straighten after grips 1710, 1714 are pulled forming a substantially straight applicator 1700. Removable grip 1710 is removed from applicator 1700 in order to allow device 1704 to be deployed out of exit 1712. A plunger (not shown) is used to expel device 1704 from enclosure 1702 out exit 1712 and into the user's vagina. In an embodiment of the invention, exit 1712 is formed from a plurality of triangular shaped segments which when closed seal enclosure 1702. Optionally, the triangular shaped segments are not made of the same material as the applicator. Optionally, the triangle shaped elements are flexible and/or soft. Optionally, the triangle shaped elements are coated with a soft material, such as polypropylene, polyethylene, compressed seaweed, compressed cellulose, cardboard, and the like. In some embodiments of the invention, applicator 1700 is lubricated, for example as described in PCT/IL2005/000304, U.S. Application Ser. No. 60/719,422, U.S. Application Ser. No. 60/762,059 and PCT/IL2006/000346. In some embodiments of the invention, the applicator is provided with a depth of insertion indicator, which indicates the proper depth to insert applicator 1700 into the vagina in order to deploy device 1704 in a position that will be effective for rendering incontinence treatment.

Exemplary Device Constructed from Tubing

FIGS. 18a, 18b, 18c and 18d depict an exemplary embodiment of the invention in which an expansion mechanism 1810 and anchor base 1811 are provided as separate pieces to be assembled with pieces of standard tubing 1860 (e.g. silicone or other flexible plastic) to form another additional exemplary device 1800. In an exemplary embodiment of the invention, tubing 1860 is separate from mechanism 1810. Optionally, tubing 1860 defines both an anchor and a support. Optionally, use of flexible tubing 1860 reduces manufacturing costs of device 1800 and/or contributes to an ability to use different combination of expansion mechanism 1810 and/or anchor base 1811 and or tubing to create devices 1800 with different dimensions and/or properties.

In an exemplary embodiment of the invention, use of tubing of different lengths and/or diameters with a single expansion mechanism 1810 and/or anchor bases 1811 of different sizes/configurations produce a series of different devices 1800 characterized by different sizes and/or configurations and/or degrees of flexibility. Optionally, device 1800 is tailored to a specific patient at time of manufacture. In an exemplary embodiment of the invention, tailoring can be by selection of diameter and/or length and/or wall thickness of tubing 1860.

Figure 18A:
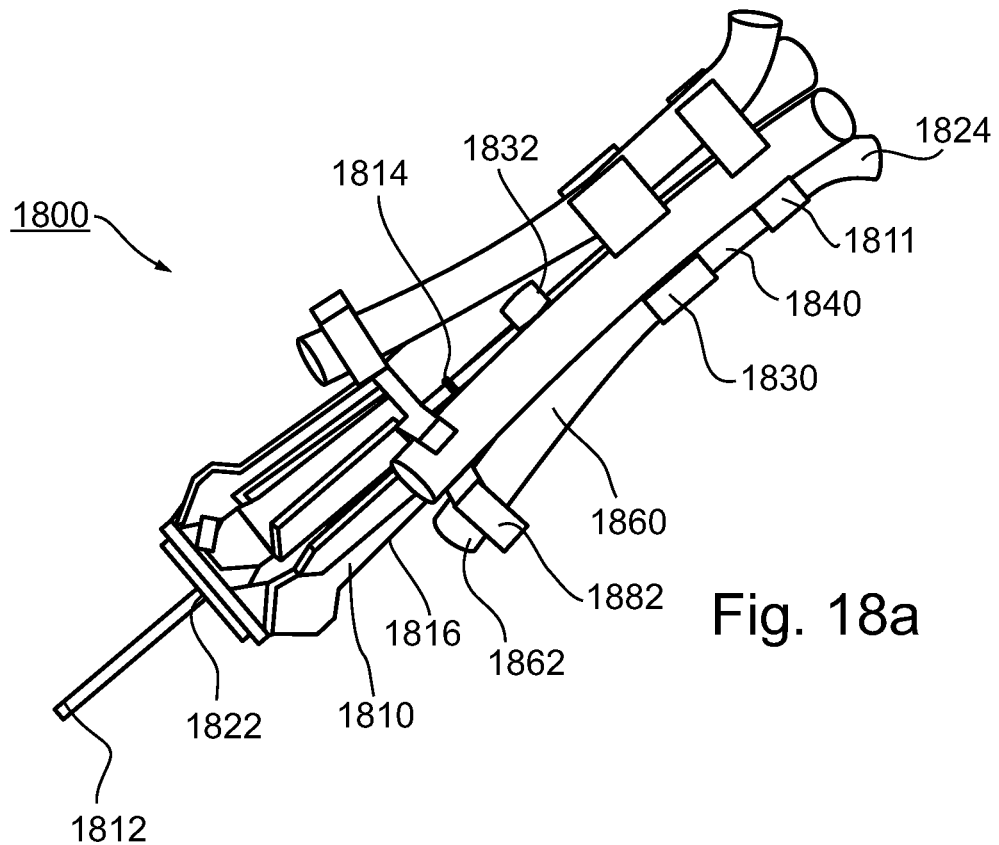
FIG. 18A is a perspective view of an exemplary device according to another exemplary embodiment of the invention in a collapsed state achieved by application of an external force.

FIG. 18a is a side view of device 1800 in its closed operational state (e.g. when loaded in an applicator). Device 1800 is similar to exemplary embodiments described hereinabove in that is normally open.

The anchor section of exemplary device 1800 comprises four flexible plastic tubes 1860 held together by anchor base 1811 and support base 1830. Portions of tubing 1860 between anchor base 1811 and support base 1830 comprise anchor legs 1840. Portions of tubing 1860 extending beyond anchor base 1811 comprise feet 1824 of anchor legs 1840. In some exemplary embodiments of the invention, feet 1824 are deflected outwards by pre-shaping of tubing 1860. In other exemplary embodiments of the invention, feet 1824 are deflected outwards by support base 1830. The support section of exemplary device 1800 comprises four support arms (tubing 1860) terminating in hands 1862. Depicted exemplary expansion mechanism 1810 comprises four plastic bars 1816 (e.g. a rigid plastic such as polyethylene) which converge at a central hub 1819 where they are attached to hub plate 1822. Optionally, hub 1819 is provided as a round plate and/or doers not engage any of tubing 1860 directly. The structures depicted in FIG. 18 are exemplary only and do not limit the invention.

Figure 18B:
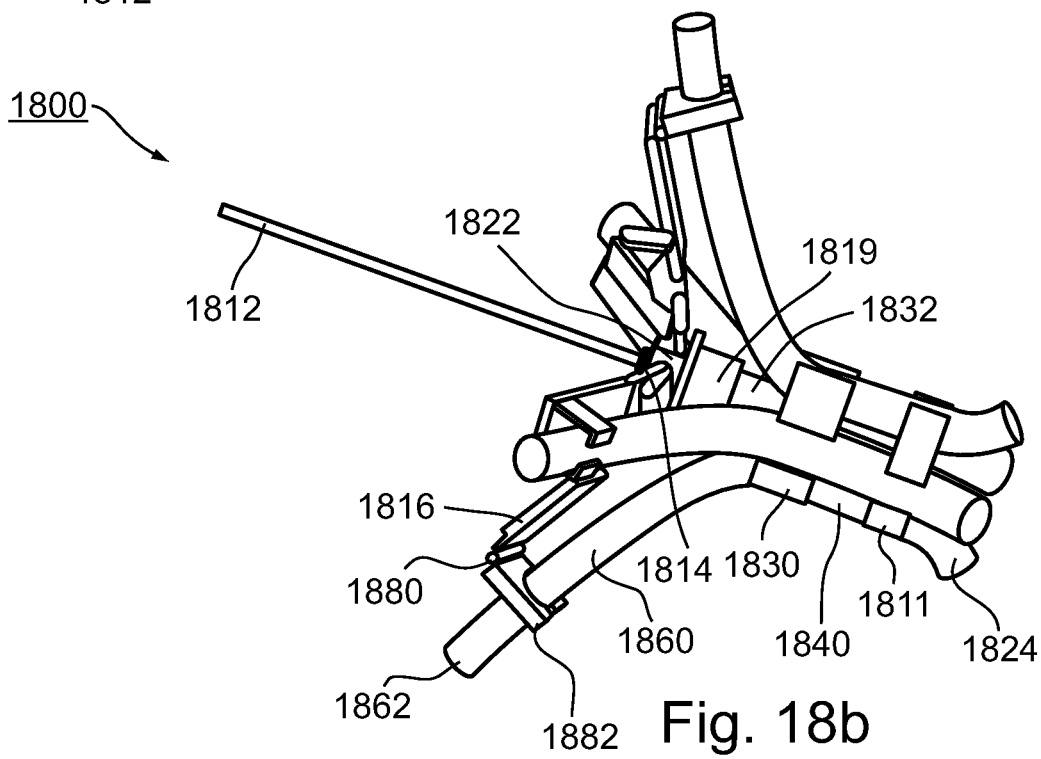
FIG. 18B is a side view of the device of FIG. 18A in its normally open position.
Figure 18C:
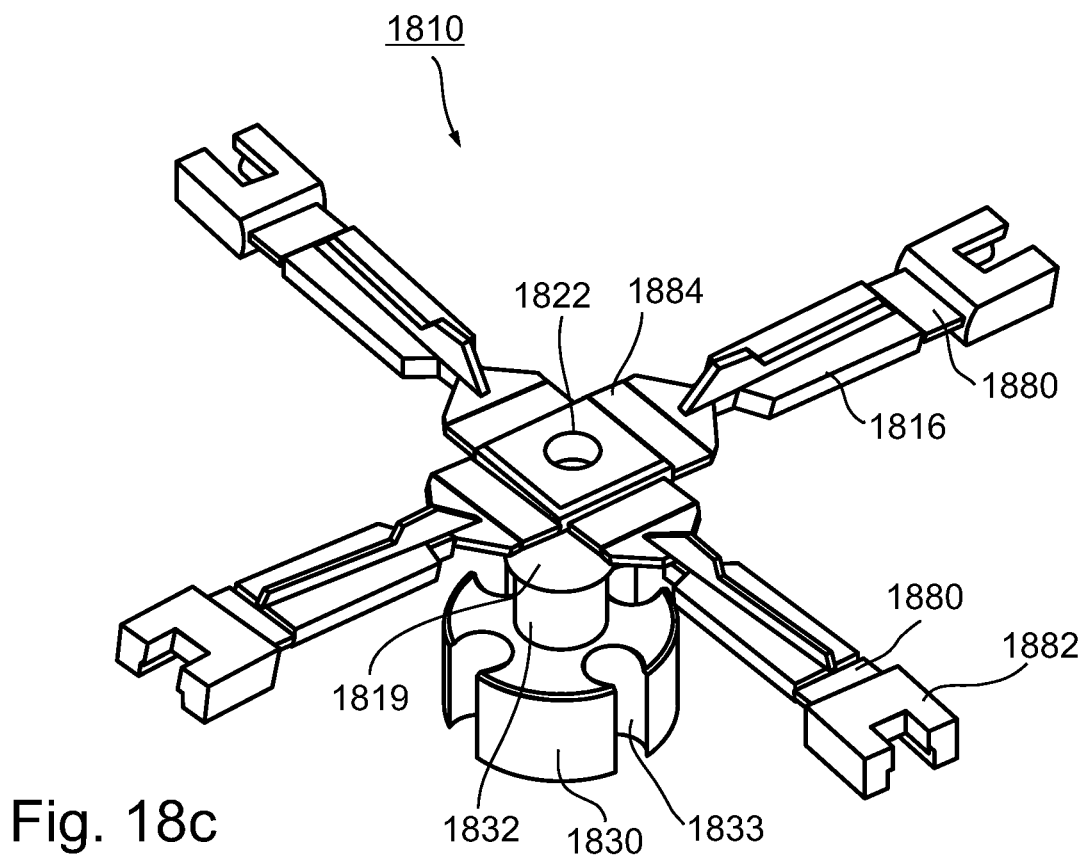
FIG. 18C is a perspective view of the expansion element of a device as depicted in FIG. 18A removed from the device.

FIG. 18c depicts expansion mechanism 1810 removed from device 1810 so that its component parts are not obscured by tubing 1860. When spoke-bars 1816 are straightened, tubular hub 1819 is brought into contact with, and optionally engages, neck 1832 of support base 1830. Optionally, each bar 1816 is aligned with a groove 1834 in support base 1830 as pictured. Grooves 1834 are adapted to engage tubing 1860 (not pictured in this view).

Figure 18D:
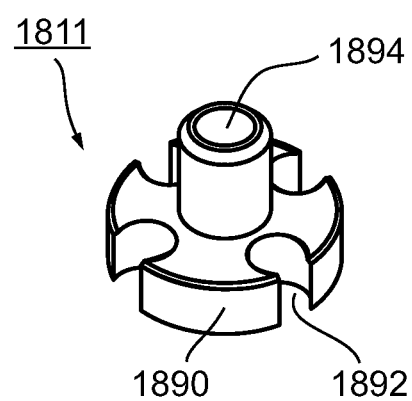
FIG. 18D is a perspective view of the anchor base of a device as depicted in FIG. 18A removed from the device.

In an exemplary embodiment of the invention, each bar 1816 comprises two or more hinges, optionally integral hinges. In the depicted embodiment, a first bar hinge 1884 is proximal to plate 1822 of hub 1819 and a second bar hinge 1880 is located near a distal end of bar 1816. In an exemplary embodiment of the invention, a distal end 1882 of each bar 1816 is adapted to engage tubing 1860. Adaptation for engagement can include, for example, a bifurcation as pictured. Optionally, one or more additional hinges are provided along the length of bar 1816. FIG. 18D shows anchor base 1811 separate from device 1800. Depicted exemplary anchor base 1811 comprises a disc-like body 1890 with grooves 1892 adapted to engage tubing 1860 (not pictured in this view). Optionally, a connector 1894 is attached to body 1890. In an exemplary embodiment of the invention, connector 1894 engages neck 1832 and/or support base 1830 of expansion mechanism 1810. Optionally, engagement of connector 1894 contributes to axial rigidity of the anchor section of device 1800.

In an exemplary embodiment of the invention, anchor base 1811 deflects anchor legs 1840 radially outwards and/or holds several pieces of tubing in a desired orientation one to another. Optionally, base 1811 engages other plastic parts.

Referring again to FIG. 18a, folding of bar hinges 1880 and 1884 while distal ends 1882 of bars 1816 engage hands 1862 of support arm tubing 1860 brings device 1800 into its closed operational state. In the depicted closed operational state, expansion mechanism 1810 is "outside" or "beyond" hands 1862. Hub 1819 is disengaged from neck 1832 of support base 1830 in this position. Optionally, hub 1819 is attached to neck 1832 by string 1812.

In an exemplary embodiment of the invention, a handle 1812 (e.g. a string), anchored in support base 1830 extends through neck 1832 and plate 1822 of hub 1819. Handle 1812 comprises at least an elastic portion. In an exemplary embodiment of the invention, a protrusion 1814 (e.g. a knot) is provided on handle 1812. Optionally, the elastic portion of handle 1812 is located between protrusion 1814 and neck 1832.

In an exemplary embodiment of the invention, a short time prior to use, the user prepares device 1800 for opening by pulling string 1812 with sufficient force to lengthen the elastic portion thereof. This pulling causes protrusion 1814 to move towards plate 1822 of hub 1819. In an exemplary embodiment of the invention, plate 1822 engages and retains protrusion 1814. When the user releases string 1812, the elastic portion of the string pulls hub 1819 towards neck 1832 of support base 1830 and expansion mechanism 1810 is activated.

FIG. 18b depicts device 1800 in its normally open operational state. Hub 1819 has approached neck 1832 of support base 1830 and support arm tubing 1860 has been flexed outward so that hands 1862 contact vaginal walls with a desired degree of force. Optionally, hub 1819 is held in proximity to neck 1832 by string 1812 or locks to neck 1832.

In an exemplary embodiment of the invention, use of tubes 1860 in conjunction with separately manufactured expansion mechanism 1810 and support base 1811 contribute to a reduction in cost of device 1800. Optionally, tubing 1860 is extruded in a continuous process and cut to desired lengths.

In an exemplary embodiment of the invention, feet 1824 of anchor legs 1840 are curved and/or thickened. Optionally, curving and/or thickening can be achieved by thermal and/or chemical treatment and/or by use of pre-shaped inserts within the tubing.

In an exemplary embodiment of the invention, grooves 1833 and/or 1892 and/or bifurcations 1882 engage tubing 1860 with sufficient force that tubing 1860 neither falls out nor slips axially with respect to these parts. Optionally, sufficient force is provided by a width of these parts relative to tubing diameter. Optionally, insertion of tubing 1860 into grooves 1833 and/or 1892 and/or bifurcations 1882 produces an audible and/or tactile click.

In an exemplary embodiment of the invention, device 1800 is inserted in an applicator (not pictured) while in the closed operational state of FIG. 18a.

Optionally, tensioning or "loading" of device 1800 is done by a pull of the string 1812 so that knot 1814 is pulled out of notch 1822, at the same time of insertion of the device into a vagina.

In an exemplary embodiment of the invention, removal of device 1800 is performed by pulling string 1812 so that hands 1862 move radially inwards. Optionally, inward radial motion of hands 1862 decreases an overall diameter of device 1800 and contributes to ease of removal.

Exemplary Covers

In an exemplary embodiment of the invention, a cover for an exemplary device according to an embodiment of the invention is fashioned with braid-able tails and placed over the device. Braiding of the tails serves to produce a removal device from a piece of material which is unitary with the cover. Optionally, the cover is fashioned from a non-woven material.

In an exemplary embodiment of the invention, a predetermined shape conforming to a particular exemplary device is cut out of a sheet (e.g. non-woven material), the cut-out is folded and the edges of the material are welded or sealed. Welding or sealing can be, for example, by heating, ultrasonic energy or gluing. The welding/sealing produces a sack which may have weld lines on an outer surface. Optionally, the sack is inverted so that the weld lines are inside. In an exemplary embodiment of the invention, placing the weld lines inside the sack contributes to a reduction in vaginal irritation. Once the device is inside the sack, The braid-able tails are braided and/or welded into a removal device (e.g. a string or cord). In an exemplary embodiment of the invention, the cover and/or braid-able tails are constructed from a non woven material characterized by a directional elasticity. Optionally, elasticity in the cross direction (Y axis) is larger than elasticity in the axial direction (X axis).

In an exemplary embodiment of the invention, cut outs to form the cover are placed at 45 degrees to allow superposition of the two vectors of elasticity and allow equal elasticity in both direction of the cover.

FIGS. 19a-19f, 20a-20c and 21a-21c depict exemplary embodiments of covers with braid-able tails adapted to form removal devices.

Figure 22A:
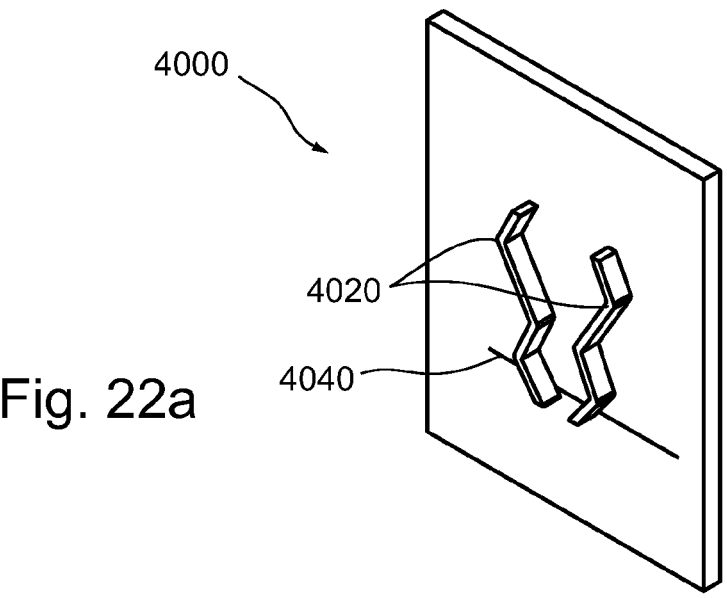
FIGS. 22A-22B are isometric and top views respectively of an exemplary welding plate for formation of a cover according to one embodiment of the invention.
Figure 22B:
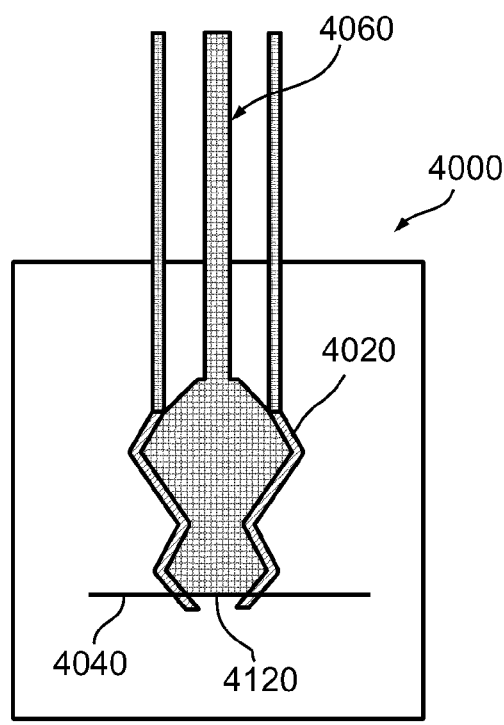
Figure 22C:
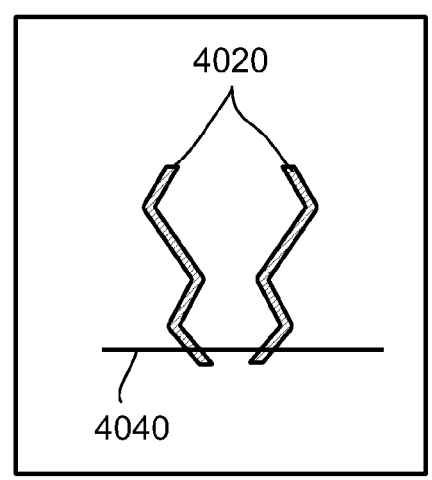
FIG. 22C is a top view as in FIG. 22B with a non-woven cover placed on the welding plate.

FIGS. 22a-22c depict an exemplary welding plate and its use in tooling of a cover according to one embodiment of the invention.

Optionally, non woven material is cut by scissors, knife, by a predetermined shaped punch, or any other cutting device or instrument known in the art. According to various embodiments of the invention, cutting occurs prior to welding, or subsequent thereto.

FIGS. 19a, 19b and 19c are plan views of a cover for an apparatus according to an exemplary embodiment of the invention. FIGS. 19a and 19b depict two halves of an exemplary cover 1900 cover with complementary weld line 1904 and a common fold line 1902. In the depicted embodiment, each half of cover 1900 comprises three braid-able tails 1906 which are not welded to one another. In tails 1906, fibers of the non woven material are optionally parallel to an axis of the tail (1908). Optionally, in the body of the cover, direction of the fiber 1910 is rotated 45 degrees to the XY axis—to allow equal elasticity of the cover in both directions.

FIG. 19*c* depicts the two halves of the cover 1900 welded and inverted to form cover 1920. In this view three pairs 1926 of tails 1906 are visible.

FIG. 19*d* depicts cover 1900 placed over an exemplary device according to the invention in perspective.

FIG. 19*e* is a cutaway view depicting cover 1900 with apparatus 1950 installed therein.

Figure 19F:
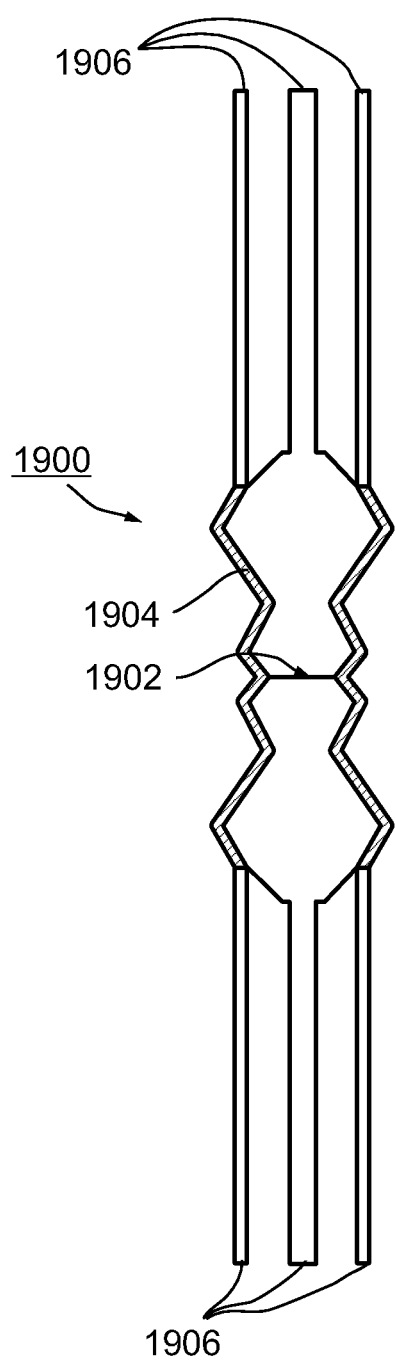
FIG. 19F is a plan view of a cover formed from a single piece of material for an apparatus according to an exemplary embodiment of the invention.

FIG. 19*f* is a plan view of a cover formed from a single piece of material by folding along a single fold line 1902.

Optionally, braiding of tails 1906 seals device 1950 inside cover 1900 and/or forms a string removal device in the form of a string or cord.

FIG. 20*a* is a plan view of a cover 2000 formed from a single piece of material for an apparatus according to another exemplary embodiment of the invention. Cover 2000 is formed by folding along fold lines 2020 and welding/sealing edges 2004 to produce 4 braid-able tails 2006.

FIGS. 20*b* and 20*c* are perspective and cutaway views respectively of cover 2000 applied to apparatus 2050 (visible in FIG. 20*c*) according to an exemplary embodiment of the invention. In the depicted embodiments, seams 2014 formed by welding of edges 2004 are non-aligned with support arms of device 2050 within cover 2000. Optionally, this non alignment contributes to a reduction in stress on seams 2004 as device 2050 expands within cover 2000.

FIG. 21*a* is a plan view of a cover 3000 formed from a single piece of material for an apparatus according to another exemplary embodiment of the invention. Cover 3000 is formed by folding along fold lines 3020 and welding/sealing edges 3040 to produce 4 braid-able tails 3060. The orientation of fold lines 3020 with respect to edges 3040 is different than in cover 2000. Optionally, this difference contributes to a change in orientation of fibers in different portions of the cover.

FIGS. 21*b* and 21*c* are perspective and cutaway views respectively of cover 3000 applied to apparatus 3150 (visible in FIG. 21*c*) according to an exemplary embodiment of the invention. In the depicted embodiments, seams 3140 formed by welding of edges 3040 are aligned with support arms of device 2050 within cover 2000. Optionally, this alignment contributes to an increase in friction between seams 3140 and support arms of device 3150 as the device expands within cover 3000. Optionally, this increase in friction contributes to a reduction in changes in rotational alignment between device 3150 and cover 3000.

Optionally, a degree of alignment of welding seams with support arms can be controlled by adjusting orientation of fold lines (2020 or 3020) with respect to welding lines (2004 or 3040).

Exemplary Production of a Cover

FIGS. 22*a* and 22*b* are isometric and top views respectively of an exemplary welding plate 4000 for formation of a cover according to one embodiment of the invention. Welding plate 4000 comprises welding areas 4020 adapted to conform to relevant welding lines. In the depicted embodiment bottom line 4040 indicates where to place a fold line (e.g. 1902 or 2020 or 3020).

FIG. 22*c* is a top view as in FIG. 22*b* with non-woven material for formation of a cover placed on welding plate 4000. In the depicted embodiment, fold line 4120 is aligned with bottom line 4040 and braidable tails 4060 protrude beyond welding plate 4000 so that heating of welding areas 4020 does not weld tails 4060.

In an exemplary embodiment of the invention, a desired shape of welding plate 4000 is made of aluminum or any other metal with good heat conductivity. Optionally, plate 4000 is larger then the material cut out to form the cover. Optionally, this size disparity contributes to a tight seal at a corner near the fold line. In order to produce the cover, the heated plate 4000 is pressed against a resistive surface (e.g. a soft anvil, for example one constructed of silicone rubber) with the non woven material is between plate 4000 and the resistive surface.

Exemplary Methods of Use

In some embodiments of the invention, any of the incontinence devices and/or applicators described herein is used for delivering drugs into the vaginal area. For example, antimicrobial agents can be delivered to the vagina. In some embodiments of the invention, the drug is released over time.

In some embodiments of the invention, some of the incontinence devices described herein, possibly with some slight modification, are used for treating prolapse.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art.

A variety of numerical indicators have been utilized to describe various components of the apparatus and/or relationships between the apparatus and a vagina and/or urethra. It should be understood that these numerical indicators could vary even further based upon a variety of engineering principles, materials, intended use and designs incorporated into the invention. Additionally, components and/or actions ascribed to exemplary embodiments of the invention and depicted as a single unit may be divided into subunits. Conversely, components and/or actions ascribed to exemplary embodiments of the invention and depicted as sub-units may be combined into a single unit with the described/depicted function.

Alternatively, or additionally, features used to describe a method can be used to characterize an apparatus and features used to describe an apparatus can be used to characterize a method.

It should be further understood that the individual features described hereinabove can be combined in all possible combinations and sub-combinations to produce exemplary embodiments of the invention. The examples given above are illustrative in nature and are not intended to limit the scope of the invention which is defined solely by the following claims.

When used in the following claims, the terms "comprises", "includes", "have" and their conjugates mean "including but not limited to". The scope of the invention is limited only by the following claims.

The invention claimed is:

1. An apparatus for treating urinary incontinence, comprising:
    a device configured for interconnecting a plurality of pieces of tubing together at a midsection of each of the pieces of tubing;

a plurality of interconnected pieces of tubing, wherein the midsection of each of the pieces of tubing are connected to the device, arranged rotationally symmetrical around a central axis of the apparatus, each piece of tubing configured to provide both anchoring for the apparatus in a vagina and support of a urethra;

wherein each piece of tubing is further characterized by a proximal section and a distal section; and, the device for interconnecting is comprised of an anchor base and a support base, the anchor base and the support base adapted with a plurality of grooves to engage and retain each piece of tubing at the proximal section and the midsection of each piece of tubing respectively.

2. An apparatus according to claim 1, wherein support of the urethra is provided according to at least one of: SUTFS, colpo-elevation or colpo-distension.

3. An apparatus according to claim 1, wherein the plurality of pieces of tubing are connected at an anchoring section of each of the pieces of tubing.

4. An apparatus according to claim 1, wherein the plurality of pieces of tubing are connected at a support section of each of the pieces of tubing.

5. An apparatus according to claim 1, wherein at least a portion of at least one of the pieces of tubing is curved.

6. An apparatus according to claim 1, wherein the pieces of tubing are flexible.

7. An apparatus according to claim 1, wherein the pieces of tubing are moisture absorbent.

8. An apparatus according to claim 1, wherein the pieces of tubing are provided with end protectors.

9. An apparatus according to claim 1, further comprising a cover enclosing the pieces of tubing and the device for interconnecting.

10. An apparatus according to claim 9, wherein the cover further comprises a removal device and is constructed of a single piece of material.

11. An apparatus according to claim 10, wherein the removal device is comprised of braided tails of the single piece of material.

* * * * *